US008859754B2

(12) United States Patent
Srivastava et al.

(10) Patent No.: US 8,859,754 B2
(45) Date of Patent: Oct. 14, 2014

(54) SYNTHESIS OF DEUTERATED RIBO NUCLEOSIDES, N-PROTECTED PHOSPHORAMIDITES, AND OLIGONUCLEOTIDES

(75) Inventors: Suresh C. Srivastava, Burlington, MA (US); Amy Yasko, Bethel, ME (US)

(73) Assignee: Ased, LLC, Bethel, ME (US)

( * ) Notice: Subject to any disclaimer, the term of this patent is extended or adjusted under 35 U.S.C. 154(b) by 0 days.

(21) Appl. No.: 13/563,343

(22) Filed: Jul. 31, 2012

(65) Prior Publication Data

US 2014/0039175 A1 Feb. 6, 2014

(51) Int. Cl.
*C07H 21/00* (2006.01)
*C07H 21/02* (2006.01)
*C07H 1/00* (2006.01)

(52) U.S. Cl.
CPC .............. *C07H 21/02* (2013.01); *C07D 59/005* (2013.01); *C07H 1/00* (2013.01)
USPC ...... 536/25.32; 536/23.1; 536/24.3; 536/25.3

(58) Field of Classification Search
None
See application file for complete search history.

(56) References Cited

PUBLICATIONS

Chirakul et al. Org. Lett. (2003), vol. 5, pp. 917-919.*
Chen et al. Tetrahedron Letters (1998), vol. 39, pp. 1103-1106.*
Foldesi et al. Tetrahedron (1998), vol. 54, pp. 14487-14514.*
Kinoshita et al. Journal of Labelled Compounds and Radiopharmaceuticals (1981), vol. 9, pp. 525-534.*
Eckstein Ann. Rev. Biochem. (1985), vol. 54, pp. 367-402.*
Glenmarec, C. et al, "The NMR structure of 31mer RNA domain of *Escherichia coli* RNase P RNA using its non-uniformly deuterium labelled counterpart [the 'NMR-window' concept]", Nucleic Acids Research, 24:11:2022-2035, (1996).
Hammond, S., "MicroRNA therapeutics: a new niche for antisense nucleic acids", 12:3:99-101, (Mar. 2006).
Sinhababu, A. et al, "Mechanism of action of S-adenosyl-L-homocysteine hydrolase. Measurement of kinetic isotope effects using adenosine-3'-d and S-adenosyl-L-homocysteine-3'd as substrates", J. Am. Chem. Soc., 107:7628-7632, (1985).
Moriarity, R. et al, "The specifically 2-monodeuterated 2-deoxy-D-riboses (2(S)- and 2(R)-Deuterio-2-deoxy-D-erthropentoses)", J. Am. Chem. Soc., 93:12:3/86/3087, (Jun. 16, 1971).
Wong, M. et al, 2-Deoxypentoses. Stereoselective reduction of ketene dithioacetals, J. Am. Chem. Soc., 100:11:3548-3553, (May 24, 1978).
Dupre, M. et al, "Synthese D'adenosine monodeuteriee stereospecifiquement En C—5'", Tetrahedron Letters, 31:2783-2786, (Jun. 5, 1978).
Roy, S. et al, "New enzymatic synthesis of 2'-deoxynucleoside-2',2'-d2 and the determination of sugar ring flexibility by solid-state deuterium NMR", J. Am. Chem. Soc., 108:1675-1678, (1986).

Pathak, T. et al, "Synthesis of 2'-deoxy-2'(S)-deuterio and 2'-deoxy-2'(R)-deuterio-β-D-nucleosides", Tetrahedron, 42:19:5427-5441, (1986).
Wu, J. et al, "Regiospecific synthesis of 2'-deoxy-2',2' '-dideuterio nucleosides", Tetrahedron, 43:10:2355-2368, (1987).
Hiyama, Y. et al, "Solid-state 2H NMR study of thymidine. Base rigidity and ribose ring flexibility in deoxynucleosides", J. Am. Chem. Soc., 111:8609-8613, (Feb. 9, 1989).
Reed, M. et al, "Acridine- and cholesterol-derivatized solid supports for improved synthesis of 3'-mofdified oligonucleotides", Bioconjugate Chem. 2:217-225, (Mar. 22, 1991).
Saison-Behmoaras, T. et al, "Short modified antisense oligonucleotides directed against Ha-ras point mutation induce selective cleavage of the mRNA and inhibit T24 cells proliferation", The EMBO Jrnl., 10:5:1111-1118, (1991).
Lagos-Quintana, M. et al, "Identification of novel genes coding for small expressed RNAs", Science, 294:26:853-858, (Oct. 26, 2001).
Foldesi, A. et al, "Synthesis of partially-deuterated 2'-deoxyribonucleoside blocks and their incorporation into an Oligo-DNA for simplification of overcrowding and selective enhancement of resolution and sensitivity in the 1H-NMR spectra", Tetrahedron, 54:14487-14514, (Sep. 30, 1998).
Chirakul, P. et al, "Stereospecific syntheses of 3'-deuterated pyrimidine nucleosides and their site-specific incorporation into DNA", American Chemical Society, Organic Letters, 5:6:917-919, (Feb. 21, 2003).
Chen, T. et al, "Synthesis of 3'-deuterated pyrimidine nucleosides via stereoselective reduction of protected 3- oxoribose", Tetrahedron Letters, 39:1103-1106, (Nov. 17, 1997).
Kinoshita, t. et al, "Preparation of deuterium-labeled nucleosides by platinum-catalyzed exchange and reduction", Journal of Labelled Compounds and Radiopharmaceuticals, 9:4:525-534, (Aug. 17, 1981).
De Paula, D. et al, "Hydrophobization and bioconjugation for enhanced siRNA delivery and targeting", RNA 2007, 13:431-456, (Feb. 28, 2007), most recent version at doi.10.1261/ma.459807.
Kraynack, B. et al, "Small interfering RNAs containing full 2'-0-methylribonuleotide-modified sense strands display Argonaute2/eIF2C2-dependent activity", RNA 2006, 12:163-176, most recent version at doi.10.1261/ma.2150806.
Chiu, Y. et al, "siRNA function in RNAi: A chemical modification analysis", RNA 2003, 9:1034-1048, most recent version at doi: 10.126/ma.5103703.
Harborth, J. et al, "Sequence, chemical, and structural variation of small interfering RNAs and short hairpin RNAs and the effect on mammalian gene silencing", Antisense and Nucleic Acid Drug Development, 13:83-105, (2003).
Manoharan, M., "RNA interference and chemically modified small interfering RNAs", Current Opinion in Chemical Biology, 8:570-579, retrieved from Internet article: http://www.sciencedirect.com (2004).
Sui, G. et al, "A DNA vector-based RNAi technology to surpress gene expression in mammalian cells", PNAS, 99:8:5515-5520, Internet article: http://www.pnas.org/cgi/doi/10.1073/pnas.082117599, (Apr. 16, 2002).

(Continued)

*Primary Examiner* — Patrick Lewis
(74) *Attorney, Agent, or Firm* — McHale & Slavin, P.A.

(57) ABSTRACT

The present invention is directed towards the synthesis of high purity deuterated sugars, deuterated phosphoramidites, deuterated nucleobases, deuterated nucleosides, deuterated oligonucleotides, and deuterated RNA's of defined sequences which can exhibit biochemically useful and biologically valuable properties, thus having potential for therapeutic uses.

25 Claims, 71 Drawing Sheets

(56) References Cited

PUBLICATIONS

Donze', O. et al, "RNA interference in mammalian cels using siRNAs synthesized with T7 RNA ploymerase", Nucleic Acids Research, 30:10:e46, Oxford Univ Press, (2002).

Mittal, V., "Improving the efficiency of RNA interference in mammals", Nature Reviews, v5, p. 355, (May 2004).

Tuschl, T., "Expanding small RNA interference", Nature Biotechnology, v20, p. 446, URL:http://biotech.nature.com, (May 2002).

Nykanen, A. et al, "ATP requirements and small interfering RNA structure in the RNA interference pathway", Cell, 107:307-321, (Nov. 2, 2001).

Nishikura, K., "A short primer on RNAi: RNA-directed RNA polymerase acts as a key catalyst", Cell, 107:415-418, (Nov. 16, 2001).

Doench, J. et al, "siRNAs can function as miRNAs", Genes Dev, 17:438-442, Retrieved from genesdev.cshlp.org, Apr. 18, 2013, most recent version at doi: 10.1101/gad.1064703.

Paddison, P. et al, "Short hairpin RNAs (shRNAs) induce sequence-specific silencing in mammalian cells", Genes Dev. 16:948-958, (2002), most recent version at doi: 10.1101/gad.981002.

Elbashir, S. et al, "RNA interference is mediated by 21- and 22-nucleotide RNAs", Genes Dev., 15:188-200, (2001), most recent version at doi: 10.1101.gad.862301.

Lim, L. et al, "Microarray analysis shows that some microRNAs downregulate large numbers of target mRNAs", Nature, v433, p. 769, (Feb. 17, 2005).

Soutschek, J. et al, "Therapeutic silencing of an endogenous gene by systemic administration of modified siRNAs", Nature, v432, p. 173, (Nov. 11, 2004).

Fire, A. et al, "Potent and scientific genetic interference by double-stranded RNA in Caenorhabditis elegans", Nature, v.391, pp. 806-811, (Feb. 19, 1998).

Oishi, M. et al, "Lactosylated poly(ethylene glycol)-siRNA conjugate through acid-labile B-thiopropionate linkage to construct pH-sensitive polyion complex micelles achieving enhanced gene silencing in hepatoma cells", J. Am. Chem. Soc., 127:1624-1625, (Aug. 20, 2004) most recent version at doi: 10.1021/ja044941d.

Li, Z. et al, "The effects of thiophosphate substitution on native siRNA gene silencing", Science Direct, Biochemical and Biophysical Research Communications 329:1-26-1030, (2005), most recent version at doi: 10.1016/j.bbrc.2005.02.071.

Layzer, J. et al, "In vivo activity of nuclease-resistant siRNAs", RNA 2004, 10:766-771, most recent version at doi: 10.1261/ma.5239604.

Huang, X. et al, "An efficient and economic site-specific deuteration strategy for NMR stdies homologous oligonucleotide repeat sequences", Nucleic Acids Research, 25:23:4758-4763, Oxford Univ Press, (1997).

Foldesi, A. et al., "The use of non-uniform deuterium labelling ['NMR-window'] to study the NMR structure of a 21mer RNA hairpin", Nucleic Acids Research, 24:7:1187-1194, Oxford Univ Press, (1996).

Oberhauser, B. et al., "Effective incorporation of 2'-O-methyl-oligorbonnucleotides into liposomes and enhanced cell association through modification with thiocholesterol", Nucleic Acids Research, 20:3:533-538, Oxford Univ Press, (1992).

Hall, A. et al, "RNA interference using boranophosphate siRNAs: structure-activity relationships", Nucleic Acids Research, 32:20:5991-6000, Oxford Univ Press, (2004).

Fisher, M. et al, "Inhibition of MDR1 expression with atriol-modified siRNAs", Nucleic Acids Research, 35:4:1064-1074, (Jan. 30, 2007) most recent version at doi: 10.1093/nar/gkl1126.

Ezra, F. et al, "Conformational properties of purine-pyrimidine and pyrimidine-purine dinucleoside monophosphates", Biochemistry, 16:9:1977, (Nov. 9, 1977).

Lee, C. et al, "Conformational properties of dinucleoside monophosphates in solution: dipurines and dipyrimidines", Biochemistry, 15:16:3627, (1976).

Alam, T. et al, "Deuterium NMR investigation of backbone dynamics in the synthetic oligonucleotide [d (CGCGAATTCGCG)]2", Biochemistry, v30, p. 9229-9237, (1991).

Alam, T. et al, "A solid-state deuterium NMR investigation of conformation and order in magnetically oriented [d (CGCGAATTCGCG)]2", Biochemistry, v29, p. 9610-9617, (1990).

Alam, T. et al, "Dynamics in synthetic oligonucleotides. A solid-state deuterium NMR study", Biochemistry, 29:4 (Apr. 10, 1990).

Brush, C. et al, "Selective reversible deuteriation of oligodeoxynucleotides: Simplification of two-dimensional nuclear Overhauser effect NMR spectral assignment of a non-self-complementary dodecamer duplex", Biochemistry, v27, p. 115-122, (1988).

Braasch, D. et al, "RNA interference in mammalian cells by chemically-modified RNA", v42, p. 7967-7975, (2003), most recent version at doi: 10.1012/bi0343774.

Kondo, N. et al, "Synthesis and proton magnetic resonance spectrum of a selectively deuterated dinucleoside monophosphate, Adenylyl-(3'-5')-adenosine", Jrnl Amer Chem Soc, 94:14:5121-5122, (Jul. 12, 1972).

Koch, H. et al, "A novel method for specific labelling of carbohydrates with deuterium by catalytic exchange", Carbohydrate Research, v.59, C1-C6, (1977).

Balza, F. et al, "Applications of catalytic, hydrogen-deuterium exchange in 13C-n.m.r spectroscopy", Carbohydrate Research v.59, C7-11, (1977).

Koch, H. et al, "The synthesis of per-c-deuterated d-glucose", Carbohydrate Research, v.64, pp. 127-134, (1978).

Balza, F. et al, "Some stereochemical characteristics of C-1H-C-2H exchange-reactions with Raney nickel catalyst in deuterium oxide", Carbohydrate Research, v.107, pp. 270-278, (1982).

Angyal, S. et al, "Selective deuteration, the rate of protium-deuterium exchange in inositols with Raney-Nickel catalyst, and the effect thereon of 0-methylation", Carbohydrate Research, v.123, pp. 13-22, (1983).

Robins, M. et al, "Nucleic acid related compounds. 42. A general procedure for the efficient deoxygenation of secondary alcohols. Regiospecific and stereoselective conversion of ribonucleoside to 2'-deoxynucleosides1", Jrnl Amer Chem Soc, v.105, pp. 4059-4065, (1983).

Wu, G. et al, "Stereoselective deuterium exchange of methylene protons in methyl tetrofuranosides: Hydroxymethyl group conformations in methyl pentofuranosides", Jrnl Org Chem, v.48, pp. 1750-1757, (1983).

Angyal, S. et al, "Selective deuteration over Raney nickel in deuterium oxide: Methyl glycosides", Carbohydrate Research, v.157, pp. 83-94, (1986).

Pathak. T., et al, "a regio and stereoselective synthesis of 2', 2'', 3', 4'-tetradeuterio-2'-deoxy nucleosides", Tetrahedron, 43:18:4227-4234, (1987).

Huang, W. et al, A solid-state deuterium NMR study of furanose ring dynamics in [d(CGCGAATTCGCG)]2, Jrnl Amer Chem Soc, v.112, pp. 9059-9068, (1990).

Robins, M. et al, "Periodinane oxidation, selective primary deprotection, and remarkably stereoselective reduction of tert-Butyldimethylsily1-Proected ribonucleoside. Synthesis of 9-(β-D-Xylofuranosyl)adenine or 3'-deuteriodenosine from adenosine", Jrnl Org Chem, v.55, pp. 410-412, (1990).

Foldesi, A. et al, Partially-deuterated nucleotide residues in large DNA duplex simplify the spectral overlap and provide both the J-coupling and nOe informations by the "NRM-window: approach", Tetrahedron, 51:36:10065-10092, (1995).

Chirakul, P. et al, "Preparation of base-deuterated 2'-deoxyasenosine nucleosides and their site-specific incorporation into DNA", Nucleosides, Nucleotides & Nucleic Acids, 20:12:1903-1913, (2001).

Marasco, C. et al, "A simplified synthesis of acridine and/or li[id containing oligodeoxynucleotides", Tetrahedron Letters, 35:19:3029-3032, (1994).

Manoharan, M. et al, "Lipidic nucleic acids", Tetrahedron Letters, 36:21:3651-3654, (1995).

\* cited by examiner

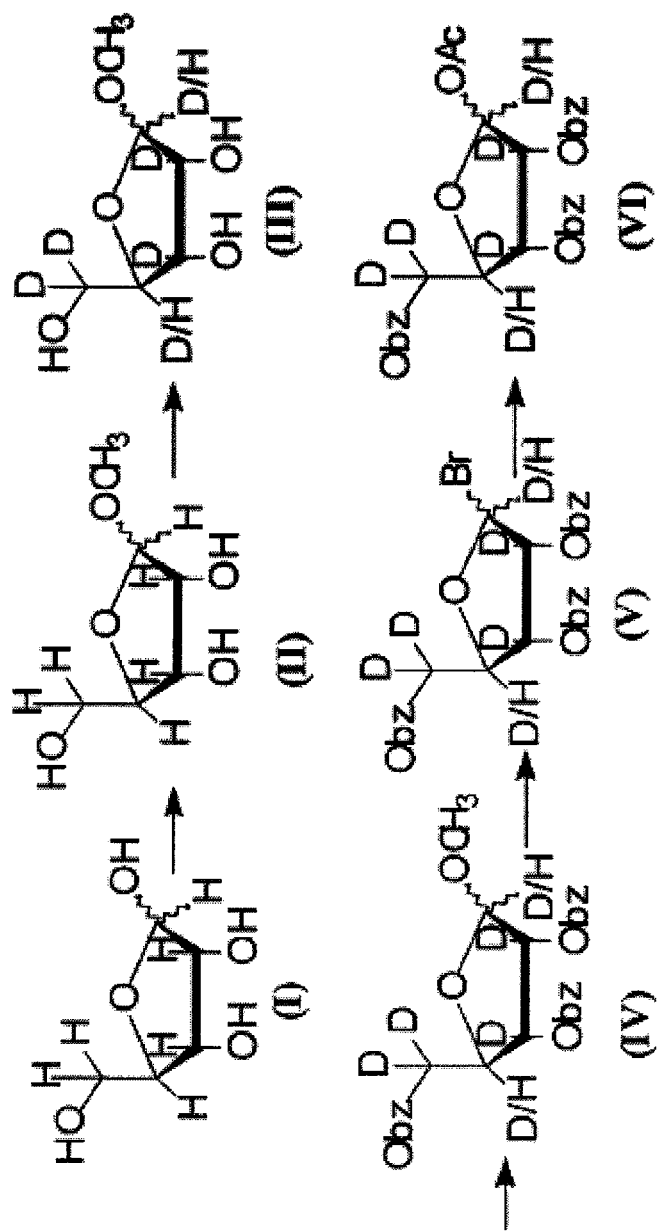
Figure 2: Scheme 1

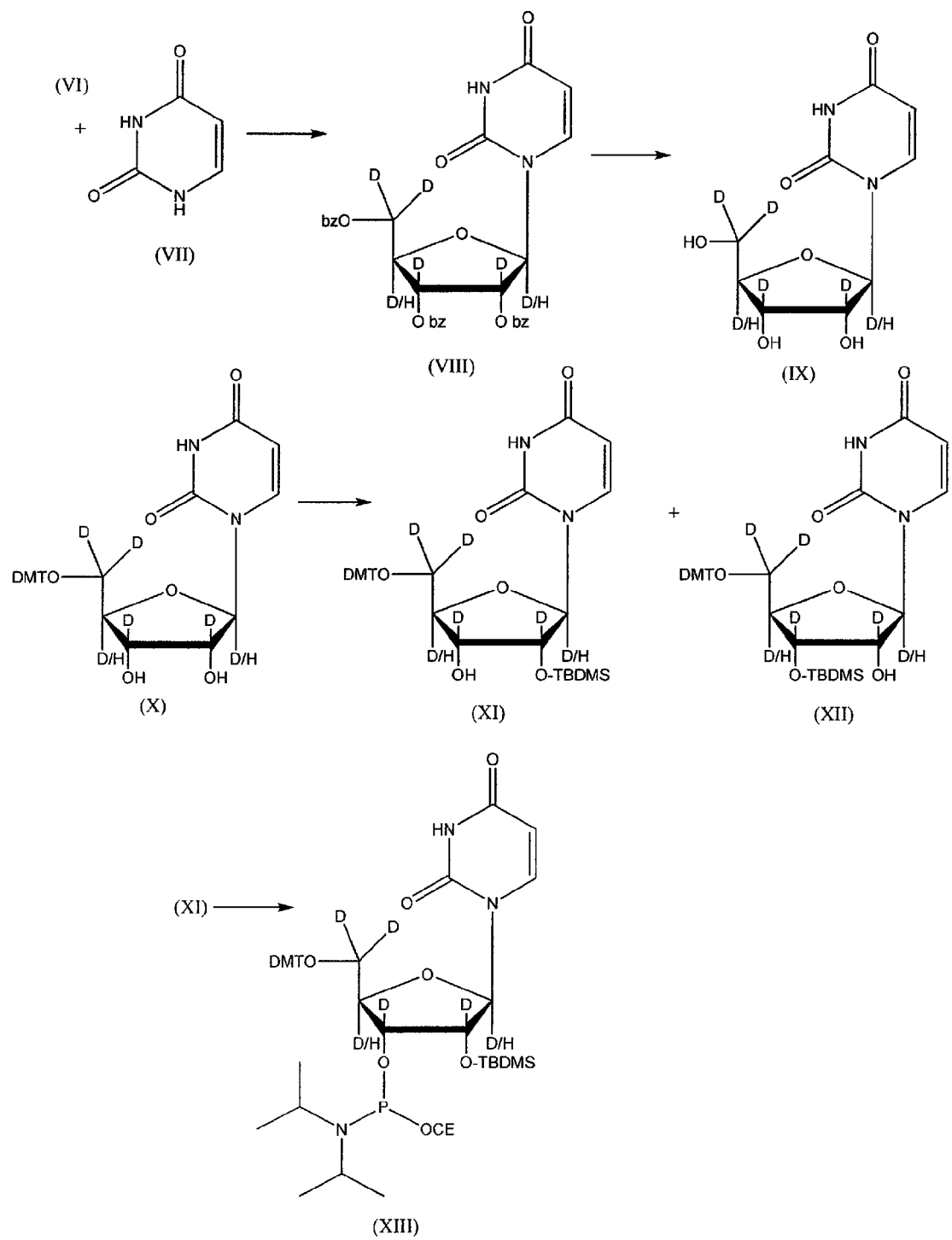
Figure 3: Scheme 2

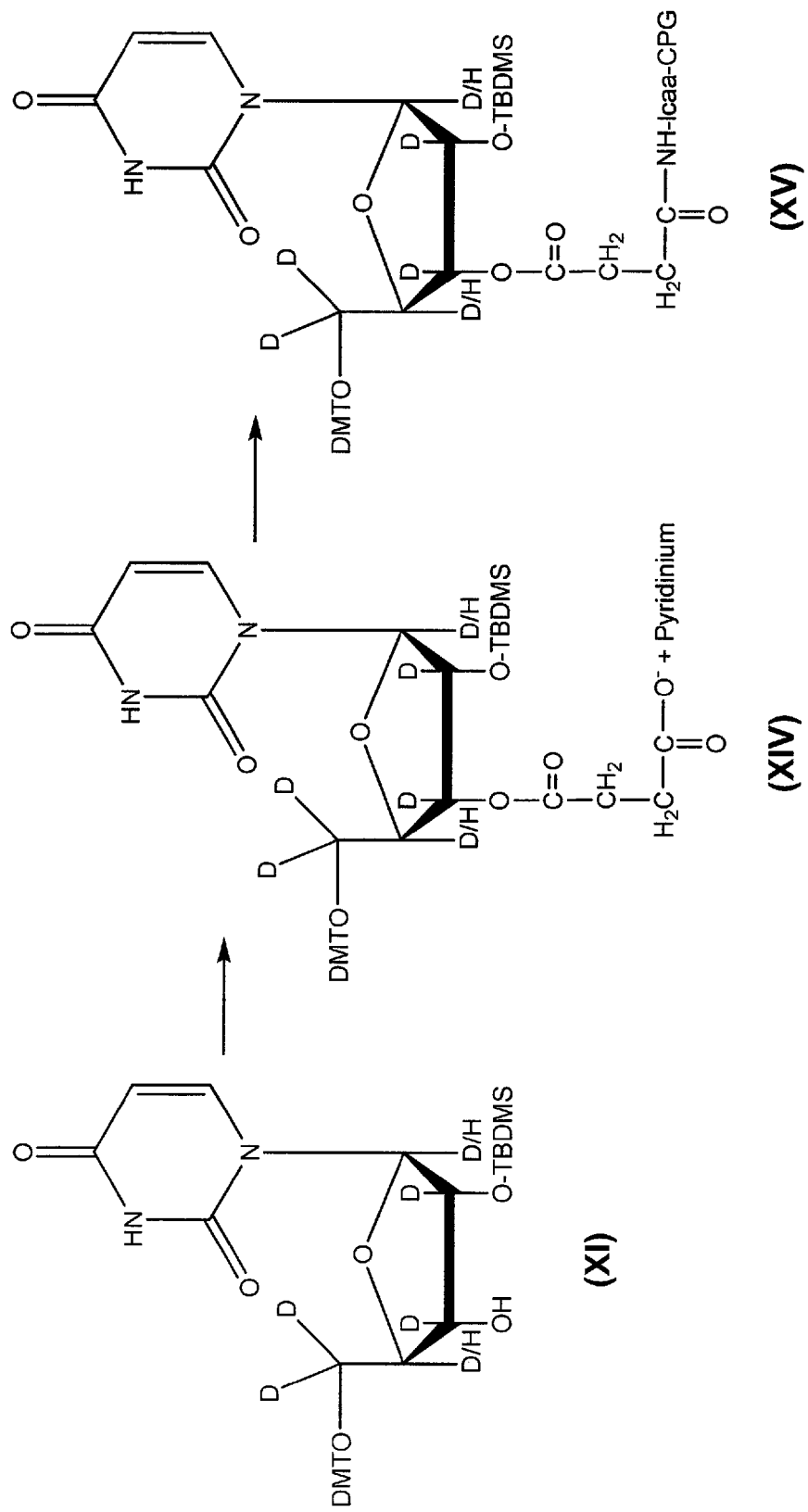
Figure 4: Scheme 3

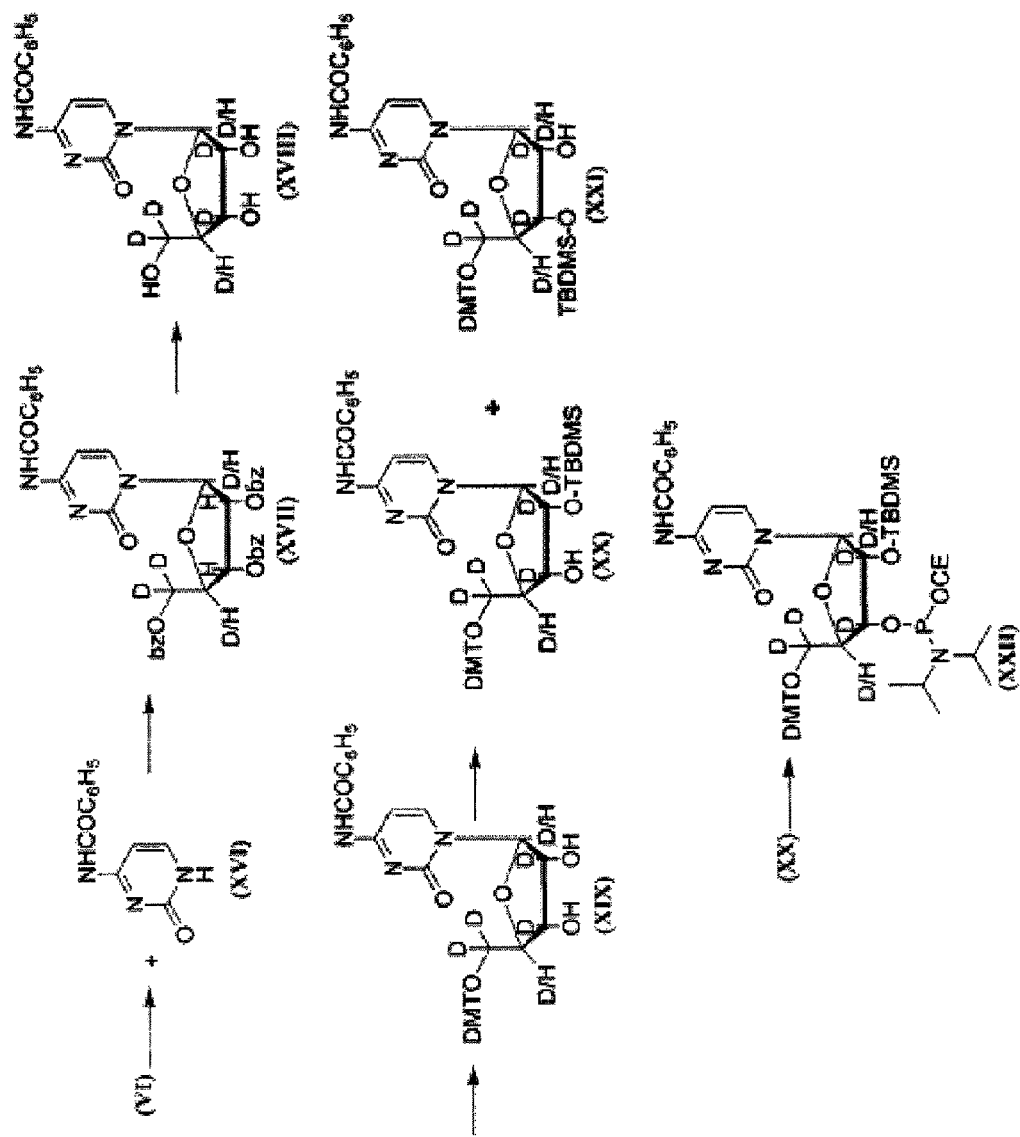
Figure 5: Scheme 4

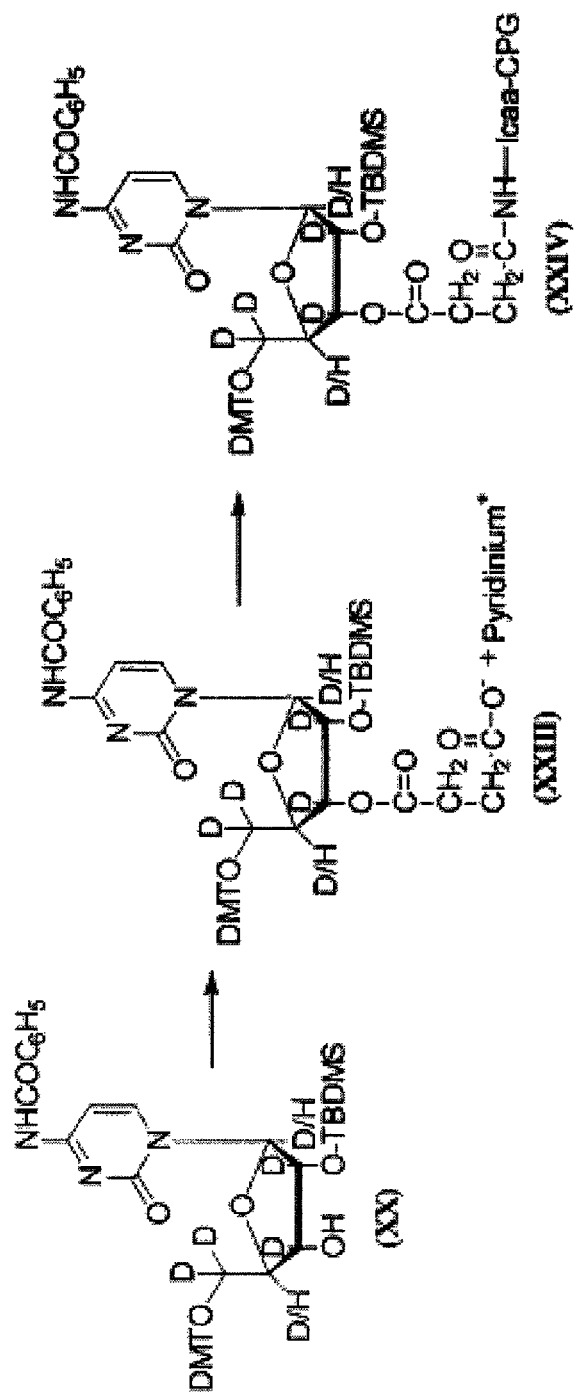
Figure 6: Scheme 5

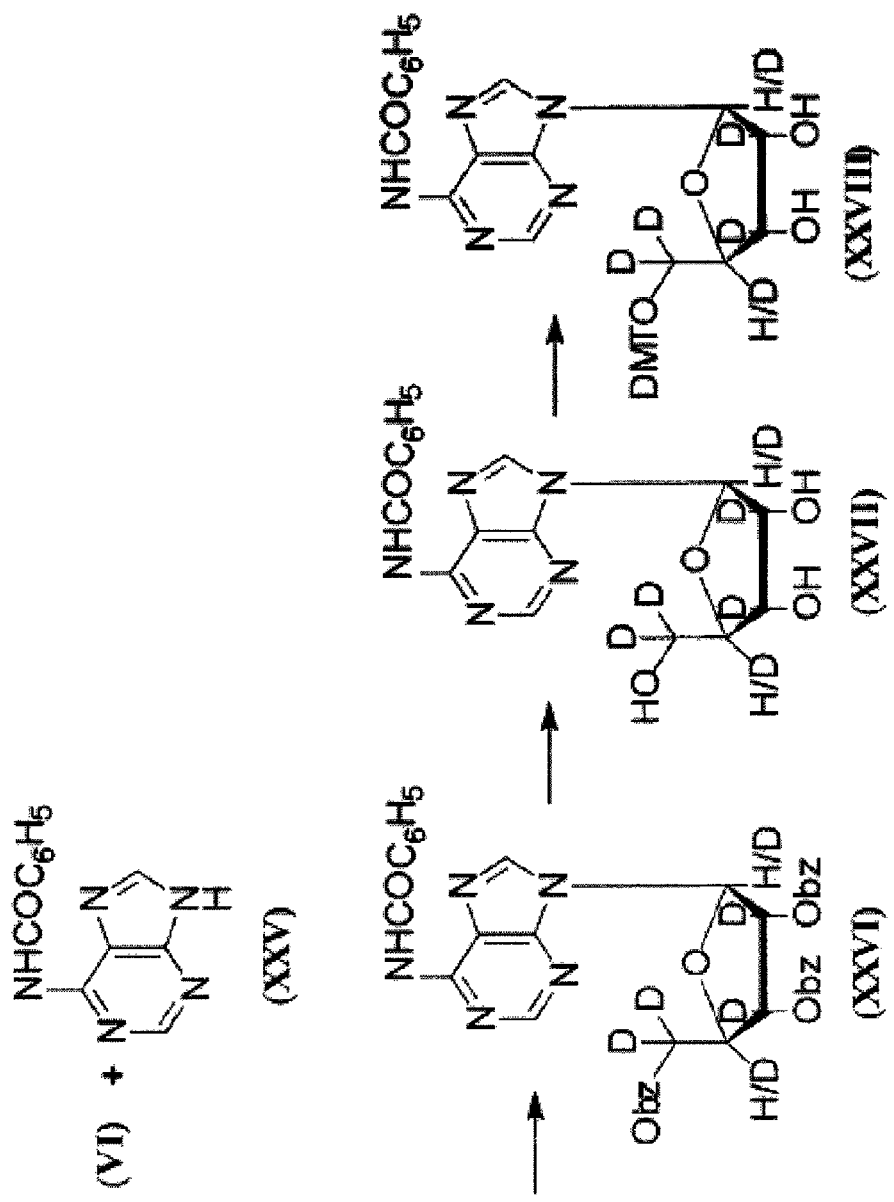
Figure 7: Scheme

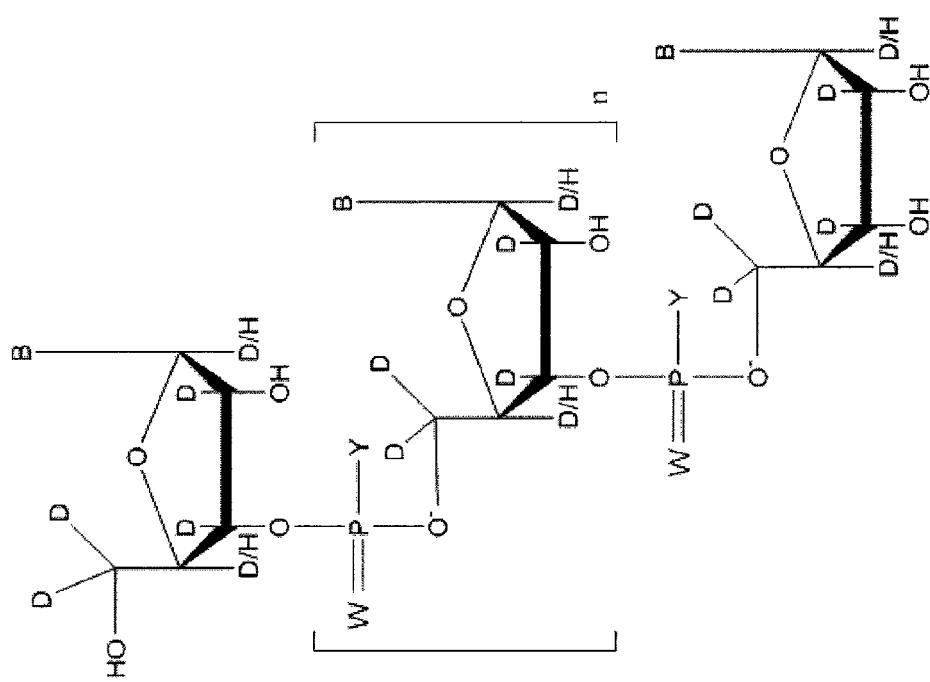
Figure 8 (Structure C-1)

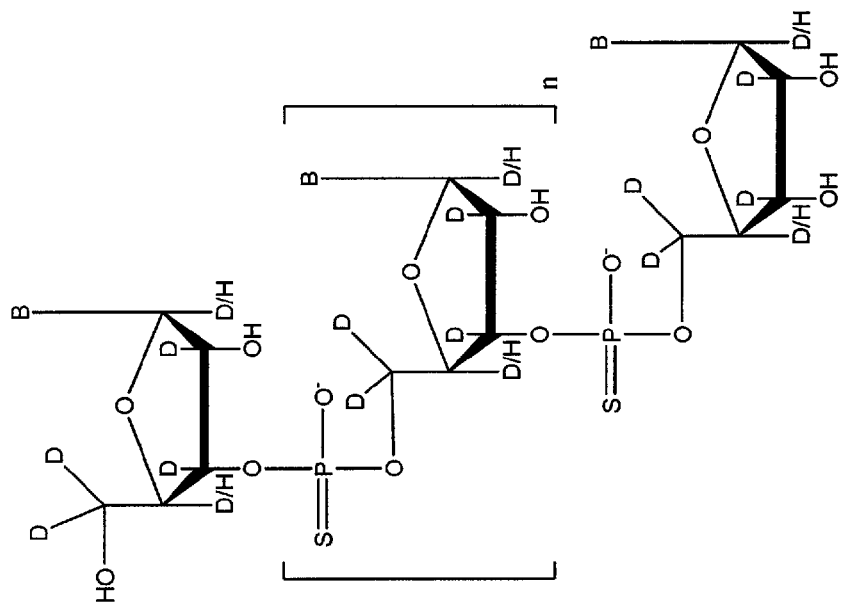
Figure 9B (Structure D-2)
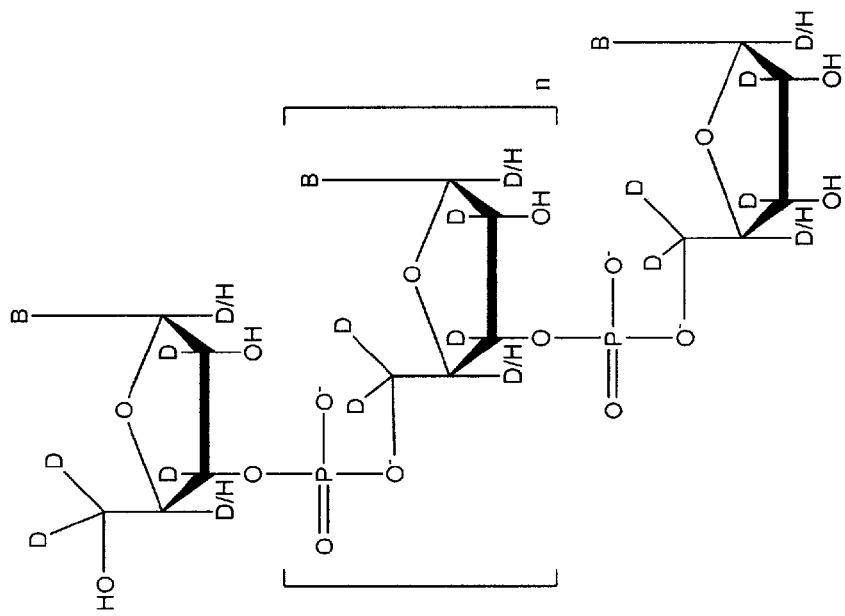
Figure 9A (Structure D-1)

| Compound structure | Solvent System | Flow Rate | Retention time | Purity at 254nm | Purity at 270nm |
|---|---|---|---|---|---|
| VIII | 0.1MTEAA: 5% ACN In 0.1MTEAA | 1.5ml/min | 7.867 | 93.43 | 94.3 |
| IX | 0.1MTEAA: ACN( 45-98%) | 1.5ml/min | 7.200 | 93.53 | 94.03 |
| X | 80%ACN : 90% ACN in 0.1M TEAA | 1.5 ml/min | 6.942 | 99.09 | 98.73 |
| XII | 0.1MTEAA: ACN (15-70%) | 1.5 ml/min | 7.708 | 96.96 | 98.02 |
| XIII | 0.1MTEAA: ACN (55-98%) Grad. | 1.5ml/min | 8.233 | 98.14 | 98.09 |
| XIV | 85% ACN: 90% ACN In 0.1M TEAA | 1.5ml/min | 7.825 | 99.16 | 99.09 |

Figure 10

Detector A - 1 (254nm)

| Pk # | Retention Time | Area | Area Percent |
|---|---|---|---|
| 1 | 3.900 | 157950 | 0.96 |
| 2 | 5.217 | 63823 | 0.39 |
| 3 | 6.517 | 211321 | 1.28 |
| 4 | 6.867 | 328661 | 1.99 |
| 5 | 7.275 | 110710 | 0.67 |
| 6 | 7.867 | 15399742 | 93.43 |
| 7 | 8.575 | 116647 | 0.71 |
| 8 | 9.200 | 64218 | 0.39 |
| 9 | 14.425 | 7670 | 0.05 |
| 10 | 15.208 | 19232 | 0.12 |
| 11 | 17.200 | 3415 | 0.02 |
| Totals | | 16483389 | 100.00 |

Figure 13B

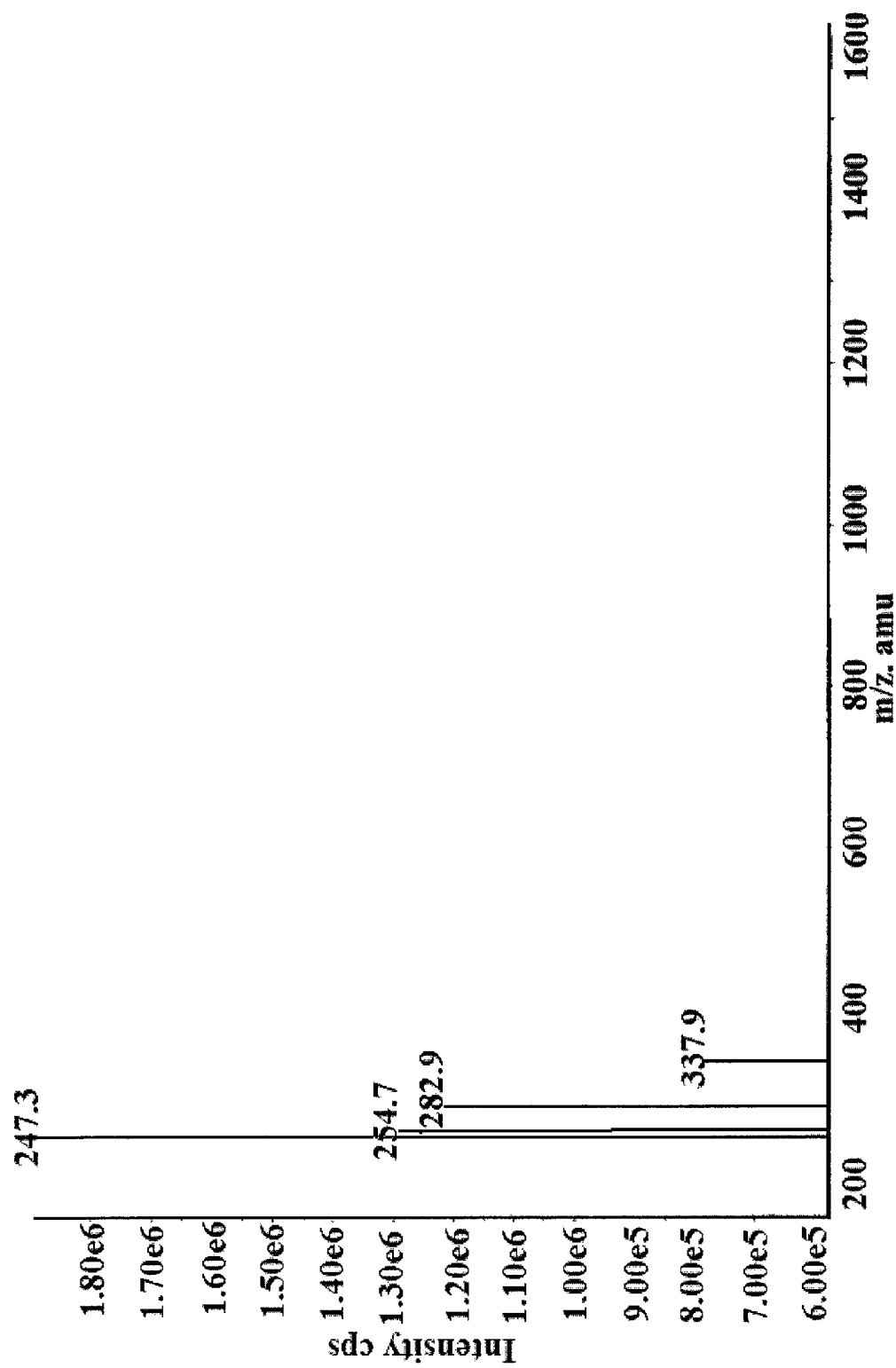

Detector A - 1 (254nm)

| Pk # | Retention Time | Area | Area Percent |
|---|---|---|---|
| 1 | 1.550 | 10041 | 0.05 |
| 2 | 3.733 | 10035 | 0.05 |
| 3 | 4.600 | 15027 | 0.08 |
| 4 | 5.283 | 138312 | 0.70 |
| 5 | 6.442 | 6917 | 0.03 |
| 6 | 7.200 | 18589379 | 93.53 |
| 7 | 7.783 | 247164 | 1.24 |
| 8 | 10.033 | 27204 | 0.14 |
| 9 | 11.175 | 122897 | 0.62 |
| 10 | 11.758 | 22479 | 0.11 |
| 11 | 12.208 | 6581 | 0.03 |
| 12 | 12.908 | 5645 | 0.03 |
| 13 | 16.983 | 31277 | 0.16 |
| 14 | 17.975 | 157062 | 0.79 |
| 15 | 18.333 | 12710 | 0.06 |
| 16 | 18.808 | 110000 | 0.55 |
| 17 | 27.142 | 246003 | 1.24 |
| 18 | 27.583 | 116821 | 0.59 |
| Totals | | 19875554 | 100.00 |

Figure 14B

| Peak No | Peak Name | Ret Time (min) | Peak Area (counts) | Result (Area %) |
|---|---|---|---|---|
| 1 | | 1.952 | 924032 | 1.03 |
| 2 | | 2.089 | 159972 | 0.18 |
| 3 | | 2.269 | 26807 | 0.03 |
| 4 | | 4.911 | 56365 | 0.06 |
| 5 | *5'-DMT-2'-TBDMS Uridine | 5.919 | 87948952 | 98.40 |
| 6 | | 7.074 | 244702 | 0.27 |
| 7 | | 7.421 | 20164 | 0.02 |
| | Totals | | 89380992 | 99.99 |

Method Notes
Column: ChromSep SS (4.6 x 250mm) with ChromSep Guard Column OmniSpher 5 C18.
Detection: UV @ 254 nm
Solvent System:
Eluent A- 80% ACN in 0.1M TEAA [pH 7.5]
Eluent B- 90% ACN in 0.1M TEAA
Gradient: Increase B (0-50%) in 20 min
Dissolved in: ACN
Flow Rate: 1.5 ml/min

Figure 15B

| Peak No | Peak Name | Ret Time (min) | Peak Area (counts) | Result (Area %) |
|---|---|---|---|---|
| 1 | | 2.018 | 23242 | 0.03 |
| 2 | | 2.649 | 24684 | 0.03 |
| 3 | | 2.866 | 1242462 | 1.35 |
| 4 | | 3.232 | 111571 | 0.12 |
| 5 | | 3.567 | 189358 | 0.21 |
| 6 | | 3.775 | 947520 | 1.03 |
| 7 | | 4.023 | 95945 | 0.10 |
| 8 | | 4.307 | 24229 | 0.03 |
| 9 | | 4.633 | 40813 | 0.04 |
| 10 | | 4.789 | 24316 | 0.03 |
| 11 | | 5.196 | 79886 | 0.09 |
| 12 | *2'-TBDMS Uridine CEP | 5.900 | 49490284 | 53.96 |
| 13 | *2'-TBDMS Uridine CEP | 6.105 | 39217584 | 42.76 |
| 14 | | 10.579 | 198721 | 0.22 |
| | Totals | | 91710616 | 100.00 |

Method Notes
Column: ChromSep SS (4.6 x 250mm) with ChromSep Guard Column OmniSpher 5 C18.
Detection: UV @ 254 nm
Solvent System:
Eluent A- 95% ACN in 0.1M TEAA [pH 7.5]
Eluent B- ACN
Gradient: Increase B (0-50%) in 20 min
Dissolved in: ACN
Flow Rate: 1.5 ml/min

Figure 16B

Absorbance Results

| Lambda(nm) | Run 1 | Run 2 | Run 3 |
|---|---|---|---|
| 250.0 | 0.4557 | 0.4552 | 0.4554 |
| 260.0 | 0.4287 | 0.4285 | 0.4284 |
| 280.0 | 0.2620 | 0.2612 | 0.2616 |

Ratio Results

| Ratio Lambdas | Run 1 | Run 2 | Run 3 | Ratio Average |
|---|---|---|---|---|
| 250/260 | 1.0630 | 1.0622 | 1.0630 | 1.0627 |
| 260/280 | 1.6359 | 1.6403 | 1.6375 | 1.6379 |

E max Results

| Scan # | E max (nm) | E maximum |
|---|---|---|
| 1 | 265.0 | 12155.6 |
| 2 | 266.0 | 12045.9 |
| 3 | 265.0 | 12144.4 |

Average Emax = 12115.3

Figure 16D

| Peak No | Peak Name | Ret Time (min) | Peak Area (counts) | Result (Area %) |
|---|---|---|---|---|
| 1 | | 1.874 | 119438 | 0.10 |
| 2 | | 2.096 | 32329 | 0.03 |
| 3 | | 2.161 | 33349 | 0.03 |
| 4 | | 2.471 | 17797 | 0.02 |
| 5 | | 3.179 | 20317 | 0.02 |
| 6 | | 3.500 | 49322 | 0.04 |
| 7 | | 3.662 | 116304 | 0.10 |
| 8 | | 3.877 | 33101 | 0.03 |
| 9 | | 4.979 | 258710 | 0.22 |
| 10 | | 5.698 | 42870 | 0.04 |
| 11 | | 6.045 | 30419 | 0.03 |
| 12 | | 6.811 | 24024 | 0.02 |
| 13 | | 7.130 | 28891 | 0.02 |
| 14 | | 7.345 | 21318 | 0.02 |
| 15 | *5'-DMT-2'-TBDMS Cytidine (n-bz) | 8.203 | 114759104 | 98.80 |
| 16 | | 9.816 | 459247 | 0.40 |
| 17 | | 10.335 | 44986 | 0.04 |
| 18 | | 14.571 | 55834 | 0.05 |
| | Totals | | 116147360 | 100.01 |

Method Notes
Column: ChromSep SS (4.6 x 250mm) with ChromSep Guard Column OmniSpher 5 C18.
Detection: UV @ 254 nm
Solvent System:
Eluent A- 85% ACN in 0.1M TEAA [pH 7.5]
Eluent B- 90% ACN in 0.1M TEAA
Gradient: Increase B (0-50%) in 20 min
Dissolved in: ACN
Flow Rate: 1.5 ml/min

Figure 17B

Detector A - 1 (254nm)

| Pk # | Retention Time | Area | Area Percent |
|---|---|---|---|
| 1 | 5.958 | 9690 | 0.51 |
| 2 | 7.708 | 1839731 | 96.96 |
| 3 | 8.208 | 11662 | 0.61 |
| 4 | 12.842 | 2488 | 0.13 |
| 5 | 15.950 | 11106 | 0.59 |
| 6 | 17.842 | 15573 | 0.82 |
| 7 | 18.333 | 7094 | 0.37 |
| Totals | | 1897344 | 100.00 |

Figure 18B

Detector A - 1 (254nm)

| Pk # | Retention Time | Area | Area Percent |
|---|---|---|---|
| 1 | 1.433 | 4847 | 0.05 |
| 2 | 1.750 | 12857 | 0.14 |
| 3 | 2.575 | 17242 | 0.19 |
| 4 | 4.092 | 7395 | 0.08 |
| 5 | 6.500 | 2966 | 0.03 |
| 6 | 7.483 | 11637 | 0.13 |
| 7 | 8.233 | 8711735 | 98.14 |
| 8 | 8.767 | 26783 | 0.30 |
| 9 | 15.517 | 32041 | 0.36 |
| 10 | 19.158 | 49456 | 0.56 |
| Totals | | 8876959 | 100.00 |

Figure 19B

| Peak No | Peak Name | Ret Time (min) | Peak Area (counts) | Result (Area %) |
|---|---|---|---|---|
| 1 | | 1.999 | 24493 | 0.02 |
| 2 | | 2.212 | 84281 | 0.06 |
| 3 | | 2.620 | 32860 | 0.02 |
| 4 | | 3.813 | 19788874 | 13.00 |
| 5 | | 4.023 | 2348548 | 1.54 |
| 6 | | 4.490 | 26322 | 0.02 |
| 7 | | 4.689 | 724144 | 0.48 |
| 8 | | 4.917 | 367174 | 0.24 |
| 9 | | 5.301 | 27622 | 0.02 |
| 10 | | 5.967 | 5308517 | 3.49 |
| 11 | | 6.618 | 337003 | 0.22 |
| 12 | | 6.969 | 334602 | 0.22 |
| 13 | | 7.440 | 2649380 | 1.74 |
| 14 | *2'-TBDMS Cytidine (n-bz) CEP | 8.622 | 88521960 | 58.17 |
| 15 | *2'-TBDMS Cytidine (n-bz) CEP | 9.185 | 31519258 | 20.71 |
| 16 | | 14.348 | 72394 | 0.05 |
| | Totals | | 152167440 | 100.00 |

Method Notes
Column: ChromSep SS (4.6 x 250mm) with ChromSep Guard Column OmniSpher 5 C18.
Detection: UV @ 254 nm
Solvent System:
Eluent A- 95% ACN in 0.1M TEAA [pH 7.5]
Eluent B- ACN
Gradient: Increase B (0-50%) in 30 min
Dissolved in: ACN
Flow Rate: 1.5 ml/min

Figure 20B

Absorbance Results

| Lambda (nm) | Run 1 | Run 2 | Run 3 |
|---|---|---|---|
| 250.0 | 0.6991 | 0.6988 | 0.6987 |
| 260.0 | 0.7442 | 0.7441 | 0.7440 |
| 280.0 | 0.3656 | 0.3652 | 0.3654 |

Ratio Results

| Ratio Lambdas | Run 1 | Run 2 | Run 3 | Ratio Average |
|---|---|---|---|---|
| 250/260 | 0.9394 | 0.9392 | 0.9391 | 0.9392 |
| 260/280 | 2.0357 | 2.0374 | 2.0363 | 2.0365 |

E max Results

| Scan # | E max (nm) | E maximum |
|---|---|---|
| 1 | 260.9 | 31795.4 |
| 2 | 260.9 | 31795.6 |
| 3 | 260.9 | 31792.1 |

Average Emax = 31794.3

Figure 20D

Detector A - 1 (254nm)

| Pk # | Retention Time | Area | Area Percent |
|---|---|---|---|
| 1 | 1.567 | 14148 | 0.13 |
| 2 | 2.375 | 354694 | 3.35 |
| 3 | 3.267 | 554757 | 5.25 |
| 4 | 8.092 | 8967780 | 84.81 |
| 5 | 8.608 | 56137 | 0.53 |
| 6 | 8.975 | 59665 | 0.56 |
| 7 | 10.258 | 359666 | 3.40 |
| 8 | 15.283 | 35596 | 0.34 |
| 9 | 16.975 | 7639 | 0.07 |
| 10 | 17.208 | 33354 | 0.32 |
| 11 | 18.383 | 130207 | 1.23 |
| Totals | | 10573643 | 100.00 |

Figure 22B

UV - 200nm
Results

| Time | Height | Area | Area % |
|---|---|---|---|
| 16.333 | 30047 | 343332 | 100.00 |
| Totals | 30047 | 343332 | 100.00 |

Figure 23B

UV - 200nm
Results

| Time | Height | Area | Area % |
|---|---|---|---|
| 18.208 | 1909 | 17861 | 3.34 |
| 18.396 | 161 | 9992 | 1.87 |
| 18.729 | 41456 | 506787 | 94.79 |
| Totals | 43526 | 534640 | 100.00 |

Figure 24B

UV - 200nm
Results

| Time | Height | Area | Area % |
|---|---|---|---|
| 16.921 | 530 | 4337 | 0.92 |
| 17.333 | 39008 | 468900 | 99.08 |
| Totals | 39538 | 473237 | 100.00 |

Figure 25B

UV - 200nm
Results

| Time | Height | Area | Area % |
|---|---|---|---|
| 16.967 | 753 | 10212 | 0.26 |
| 17.379 | 1754 | 23439 | 0.60 |
| 19.000 | 135328 | 3888424 | 99.14 |

| Totals | 137835 | 3922075 | 100.00 |
|---|---|---|---|

Figure 26B

UV - 200nm
Results

| Time | Height | Area | Area % |
|------|--------|------|--------|
| 16.479 | 1964 | 60428 | 1.17 |
| 17.492 | 20 | 14502 | 0.28 |
| 18.467 | 158100 | 5082094 | 98.55 |

| | | | |
|---|---|---|---|
| Totals | 160084 | 5157024 | 100.00 |

Figure 27B

SYNTHESIS OF DEUTERATED RIBO NUCLEOSIDES, N-PROTECTED PHOSPHORAMIDITES, AND OLIGONUCLEOTIDES

CROSS REFERENCE TO RELATED APPLICATIONS

This application is related to U.S. patent application Ser. No. 13/563,263, filed Jul. 31, 2012, entitled, "Synthesis of Deuterated Ribo Nucleosides, N-Protected Phosphoramidites, and Oligonucleotides".

FIELD OF THE INVENTION

The present invention relates to oligonucleotides and oligonucleotide synthesis; and more particularly, to modified RNA, phosphoramidites, and RNA oligonucleotides, and processes for synthesizing RNA containing partially or fully saturated deuterated sugar and/or nucleobases and deuterated phosphoramidites for synthesis of the modified oligonucleotides.

BACKGROUND OF THE INVENTION

The present invention is directed towards the synthesis of high purity deuterated sugars, deuterated nucleobases, deuterated nucleosides and deuterated RNA's of defined sequences which can exhibit biochemically useful and biologically valuable properties, thus having potential for therapeutic uses. The past several decades have seen the development of many RNA and DNA sequences for use in therapeutics, diagnostics, drug design, selective inhibition of an RNA sequence within cellular environments, and blocking a function of different types of RNA present inside the cell. One approach has been the use of antisense technology. Antisense oligonucleotides are useful for specifically inhibiting unwanted gene expression in mammalian cells. Antisense oligonucleotides can be used to hybridize to and inhibit the function of an RNA, typically a messenger RNA, by activating RNase H. Primarily, the oligonucleotides affect the level of the target RNA by activation of RNase H, which cleaves the RNA strand of DNA/RNA hybrids. As a result, antisense oligonucleotides have been proposed for the treatment of diseases. While such technology has the potential to be a powerful tool for all diseases, several issues, including molecule stability, have prevented the technology from being a major disease fighting therapy.

Another approach focuses on silencing gene expression at the mRNA level with nucleic acid-based molecules. RNA interference (RNAi) offers great potential for selective gene inhibition and provides great promise for control and management of various biochemical and pharmacological processes. Early studies illustrated that RNA interference in *C. elegans* is mediated by 21 and 22 nucleotide RNA sequences, see Fire et al., Nature, 391, 806-811, 1998. This was further confirmed by studies illustrating the general phenomenon of specific inhibition of gene expression by small double stranded RNA's mediated by 21 and 22 nucleotide RNA's, Genes Dev., 15, 188-200, 2001. Simultaneous studies confirmed such phenomenon of specific gene expression by small double stranded (dS) RNAs in invertebrates and vertebrates alike. Various studies have also illustrated the use of RNAi as a powerful tool for selective and specific gene inhibition and regulation, see Nishikura, K., Cell, 107, 415-418, 2001; Nykanen, et al., Cell, 107, 309-321, 2001; Tuschl, T., Nat. Biotechnol., 20, 446-448, 2002; Mittal, V., Nature Rev., 5, 355-365, 2004; Proc. Natl. Acad. Sci. USA, 99, 6047-6052, 2002; Donze, O. & Picard, D., Nucl. Acids. Res., 30, e46, 2002; Sui, G et al., Natl. Acad. Sci. USA, 99, 5515-5520, 2002; Paddison, et al., Genes Dev., 16, 948-959, 2002.

In addition to the use of natural double stranded (ds) RNA sequences, chemically modified RNA have been shown to cause similar or enhanced RNA interference in mammalian cells using 2'-deoxy-2'-fluoro-beta-D-arabinonucleic acid (FANA) into sequences for siRNA activities, see Dowler, et al., Nucl. Acids Res., 34, 1669-1675, 2006. Various other modifications to improve SiRNA properties have been pursued, including alterations in backbone chemistry, 2'-sugar modifications, nucleobase modifications, see reviews Nawrot, B et al., Med. Chem., 6,913-925, 2006 and Manoharan, M. Curr. Opin. Chem. Biol., 8, 570-579, 2004. While modifications of SiRNA have been tolerated, several studies indicate an increased toxicity and reduced efficacy see Harborth, et al., Antisense Nucleic Acid Drug Dev., 13, 83-105, 2003. Chiu et al. demonstrated that the 2'-O-methyl modification, although maintaining an A form RNA-like helix, does retain SiRNA activity, or in some cases, reduces SiRNA activity depending on the number of such modifications within a sequence, see RNA, 9, 1034-1048, 2003. It has also been shown that extensive 2'-O methyl modification of a sequence can be made in the sense strand without loss of SiRNA activity, see Kraynack, B. A., Baker, B. F., RNA, 12, 163-176, 2006. Bicyclic locked nucleic acids (LNA's) that confer high binding affinity have been introduced in SiRNA sequences, especially when the central region of SiRNA sequence is avoided, see Braash, et al., Biochemistry, 42, 7967-7995, 2003. Similarly, altritol sugar modified oligonucleotides (ANA), which contain rigid conformations, and has been shown to form degradable duplexes with RNA in a sequence specific manner. In addition, ANAs have been shown to stay in A (RNA type) conformation. Fisher, M., et al., Nucl. Acids Res., 35, 1064-1074, 2007 demonstrated that ANA modified siRNAs targeting MDR1 gene exhibited improved efficacy as compared to unmodified controls, specifically effective when modification was near the 3'-end of sense or anti-sense strand.

Several studies have indicated the potential for siRNA uptake by various delivery systems. Such delivery systems can then be exploited in the development of therapeutics. Cholesterol-conjugated siRNA can achieve delivery into cells and silence gene expression. In addition, lipid conjugated siRNA, bile acids, and long chain fatty acids can mediate siRNA uptake into cells and silence gene expression in vivo. Efficient and selective uptake of siRNA conjugates in tissues is dependent on the maximum association with lipoprotein particles, lipoprotein/receptor interactions and transmembrane protein mediated uptake. High density lipoproteins direct the delivery of siRNA into the liver, gut, kidney and steroidal containing organs. Moreover, LDL directs siRNA primarily to the liver. Studies have indicated that the LDL receptor is involved in the delivery of siRNA. Therefore, it has been proposed that siRNA can be designed with chemical modifications to protect against nuclease degradation, abrogate inflammation, reduce off target gene silencing, and thereby improve effectiveness for target genes. Delivery vehicles or conjugates of lipids and other lipophilic molecules which allow enhanced cellular uptake are essential for therapeutic developments. Such siRNAs are presently being developed for human target validation and interfering with diseases pathways and developing new frontier for drug development.

The 3'-end of sense strand of siRNA can be modified and attachment of ligands is most suited at this end, see for example, Ya-Lin Chiu and Tariq Rana, RNA, 9, 1034-1048, 2003; M. Manoharan, Curr. Opin. Chem. Biol, 6, 570-579, 2004; Nawrot, B. and Sipa, K., Curr. Top. Med. Chem., 6, 913-925, 2006; Scaringe, S., et al. Biotechnol., 22, 326-30, 2004. The introduction of lipophilic or hydrophobic groups and enhancement of siRNA delivery and optimization of targets has been addressed and achieved through bioconjugation. Generally the attachment is performed at the 3'-end of the sense strand, but can be performed on the 3'-end of the anti-sense strand. The design of nuclease resistant siRNA has been the subject of intense research and development in attempts to develop effective therapeutics. Thus base modifications such as 2-thiouridine, pseudouridine, and dihydrouridine have illustrated the effect on conformations of RNA molecules and the associated biological activity, see Sipa et al., RNA, 13, 1301-1316, 2007. Layzer, et al., RNA, 10, 766-771, 2004, illustrated that 2'-modified RNA, especially 2'-fluoro, have great resistance towards nuclease and are biological active in-vivo. Dande et al., Med. Chem., 49, 1624-1634, 2006 used 4'-thio modified sugar nucleosides in combination of 2'-0 alkyl modification for improving siRNA properties and RNAi enhancement. Li et al., Biochem. Biophys. Res. Comm., 329, 1026-1030, 2005 and Hall et al., Nucl. Acids Res., 32, 5991-6000, 2004 illustrated the replacement of internucleotide phosphate with phosphorothioate and boranophosphates of siRNAs in vivo.

In addition to in vivo stability and appropriate modification of nucleosides, bioconjugation of siRNA molecules, RNA molecules, aptamers and synthetic DNA molecules require key features for cell membrane permeability. Insufficient cross-membrane cellular uptake limits the utility of siRNAs, other single stranded RNAs, or even various DNA molecules. Thus cholesterol attached at the 3'-end of siRNA has been shown to improve in vivo cell trafficking and therapeutic silencing of the gene, see Soutschek et al., Nature, 432, 173-0178, 2004. In addition to cholesterol, various conjugations have been developed, including natural and synthetic protein transduction domains (PTDs), also called cell permeating peptides (CPPs) or membrane permanent peptides (MPPs). PTDs are short amino acid sequences that are able to interact with the plasma membrane. The uptake of MPP-siRNA conjugates takes place rapidly. Such peptides can be conjugated preferably to the 3'-end of the strand. PEG (polyethylene glycols-oligonucleotide) conjugates have been used in various conjugate complexes and possess significant gene silencing effect after uptake in target cells, see Oishi et al., Am. Chem. Soc., 127, 1624-1625, 2005. Aptamers have been used for site specific delivery of siRNAs. Given that aptamers have high affinity for their targets, conjugates with siRNA act as an excellent delivery system and results in efficient inhibition of the target gene expression, see Chu et al., Nucl. Acids Res., 34(10), e73, 2006. These molecules can be conjugated at the 3'-end of siRNA or other biologically active oligonucleotides. Various lipid conjugations at the 3'-end can be attached to oligonucleotides synthesized by the process described by the invention and can be utilized for efficient internalization of oligonucleotides. The lipophilic moiety consists of a hydroxyl function to synthesize a phosphoramidite. Similarly the lipophilic moiety can have carboxylic function at the terminus. The latter can be coupled to a 3'-amino group having a spacer, synthesized by last addition of amino linkers such as C-6 amino linker amidite, of the reverse synthesized oligonucleotide, to the carboxylic moiety using DCC (dicyclohexyl cabodiimide) or similar coupling reagent, see Paula et al., RNA, 13, 431-456, 2007.

Micro-RNA (miRNA) is a large class of non coding RNAs which have been shown to play a role in gene regulation, see Bartel, D. P. Cell, 116, 281-297, He et al. Nat. Rev. Genet, 5:522-531, 2004; Lagos-Quintana et al., Science, 204:853-858, 2001. It is estimated that there are at least 1000 miRNA scattered across the entire human genome. Many of these miRNAs have been shown to down regulate large numbers of target mRNAs, see Lim et al., Nature, 433:769-773, 2005. Different combinations of miRNAs may be involved in regulation of target gene in mammalian cell. siRNA has been shown to function as miRNAs, see Krek et al., Nat. Genet., 37: 495-500, 2005; Doench et al., Genes Dev., 17:438-442, 2003. Micro-RNAs have great potential as therapeutics and in gene regulation, Hammond, S. M., Trends Mol. Med. 12:99-101, 2006. A vast amount of effort is currently being devoted towards understanding miRNA pathways, their role in development and diseases, and their role in cancer. Additionally, miRNA targets are being developed for therapeutic and diagnostics development. A great number of miRNA are being identified and their role is being determined through microarrays, PCR and informatics. Synthesis of RNA designed to target miRNA also requires RNA synthesis and similar modification, as required for SiRNAs, for stability of RNA and bioconjugation resulting in better cellular uptakes. The instant invention will greatly accelerate the pace of this research and development.

Synthesis of therapeutic grade RNA and siRNA requires modification or labeling of the 3'-end of an oligonucleotide. In the case of siRNA, generally it is the 3'-end of the sense strand. The synthesis of 3'-end modified RNA requiring lipophilic, long chain ligands or chromophores, using 3' to 5' synthesis methodology is challenging, and requires corresponding solid support. Such synthesis generally results in low coupling efficiency and lower purity of the final oligonucleotide in general because of a large amount of truncated sequences containing desired hydrophobic modification. The authors of the instant invention approached this problem by developing reverse RNA monomer phosphoramidites for RNA synthesis in the 5' to 3'-direction. This approach leads to very clean oligonucleotide synthesis, thus allowing for introduction of various modifications at the 3'-end cleanly and efficiently.

In order to increase stability, oligonucleotides containing lipids have been synthesized. Attachment of the lipids provides for efficient delivery of the RNA and an increase in the cellular concentration of the oligonucleotides. Hydrophobic molecules, such as cholesterol, can bind to LDL particles and lipoproteins to activate a delivery process involving these proteins to transport oligonucleotides. Lipped nucleic acids may also reduce the hydrophilicity of oligonucleotides. It has also been shown that lipidoic nucleic acids improve the efficacy of oligonucleotides, see Shea, et al., Proc. Natl. Acad. Sci. USA 86, 6553, 1989; Oberhauser, B., and Wagner, E., Nucleic Acids Res., 20, 533, 1992; Saison,-Behmoaras, et al., The EMBO Journal, 10, 1111, 1991; Reed et al., Bioconjugate Chem., 2, 217, 1991; Polushin, et al., Nucleosides & Nucleotides, 12, 853, 1993; Marasco et al., Tetrahedron Lett., 35, 3029, 1994. A series of hydrophobic groups such as adamantane, eicosenoic acid, cholesterol, and dihexadecyl glycerol were attached to oligodeoxy nucleotide sequences at the 3'-end and were hybridized to complementary RNA sequences. The Tm was found to be unaffected indicating that such groups do not interfere with oligo hybridization properties see Manoharan et al., Tetrahedron Lett., 36, 1995; Manoharan, et al., Tetrahedron Lett., 36, 3651-3654, 1995; Gerlt, J. A. Nucleases, 2nd Edition, Linn, S. M., Lloyd, R. S., Roberts, R. J., Eds. Cold Spring Harbor Laboratory Press, p- 10, 1993.

For efficient delivery of synthetic RNA molecules, PEG attachment to various oligonucleotides has shown favorable properties. PEG-oligomers have shown enzymatic stability by preventing fast digestion. The thermal melting behavior was not affected, thereby retaining properties of double strand formation. Srivastava et al., Nucleic Acids Symposium Series, 2008, 52, 103-104 recently developed a reverse RNA synthesis process for clean attachment of lipophilic and large molecules to synthetic RNA.

DESCRIPTION OF THE PRIOR ART

Deuterium labeling studies & NMR analysis have been carried out for many nucleosides and oligonucleotides. The structure and dynamics of DNA and RNA is vital to understanding their biological functions. This has been investigated by a variety of physico-chemical techniques. Amongst these techniques, Nuclear Magnetic Resonance (NMR) spectroscopy have been utilized extensively as a powerful tool because it provides conformational information on the implication of variation of local structures and the dynamics under a biological condition. This has been refined using powerful computers and high resonance energy instruments. With increasing magnetic field, the higher sensitivity reduces the amount of an oligomer needed to obtain a good quality spectrum, and increases the dispersion of resonance signals reducing the spectral complexity due to resonance overlap which results from second order J couplings to first order.

Most of the studies describing incorporation of deuterium at specific positions of deoxynucleosides, ribonucleosides, and modified nucleosides were carried out in an effort to determine the structure of oligonucleosides and conformational details by proton Nuclear Magnetic Resonance (NMR). Proton NMR spectrum of oligonucleotides are generally quite complex and do not reveal conformational & structural information. As a result of oligonucleotides having significant overlapping NMR resonance, structure determination of deuterated oligonucleotides has been used for NMR structure determination of biologically functional DNA or RNA molecules. In order to overcome problems associated with resonance, investigators developed non-uniform deuterium labeling techniques, see Foldesi et al., J. Tetrahedron, 1992, 48, 9033; Foldesi et al., J., Biochem. Biophys. Methods, 1993, 26. Deuterium labeled oligonucleotides simplifies NMR spectras, allowing determination of both J couplings and NOE volumes in an unambiguous manner from a small domain of a large molecule see Glemarec et al., J. Nucleic Acids Res., 1996, 24, 2002 and Ludwig, J. Acta Biochem. Biophys Acad. Sci., 1981, 16, 131.

Similarly, site specific deuteration of a large number of oligo-DNAs and RNAs have been used to study NMR structures by the "NMR-window" concept in which only a small segment of the oligonucleotide is NMR visible. This approach was used to solve the NMR structure of a 21-mer RNA hairpin loop, see Nucleic Acids Research 1996 24:1187 and Nucleosides and Nucleotides 1997, 5&6, 743, and a 31-mer stem-internal loop-stem-internal loop-stem-hairpin loop RNA. Diastereospecifically C-2' (deuterium labeled nucleoside block in oligo-DNA (Journal Tetrahedron, 1995, 51, 10065) was successfully utilized in NMR interpretation the collection of reduced spin-diffusion as well as the extraction of $^{3}$/H1', H2" and $^{3}$/H1', H2" coupling constants.

Huang et al., Acids Research, 1997, 25, 4758-4763 showed that in two dimensional (2D) NOESY spectra of oligonucleotides, if H-8 of purines and H-6 in pyrimidines are replaced with deuterium then the entire cross peaks correlating the nucleobase with sugar protons disappear. Similarly researchers have been interested in studying the role of dynamics of interaction of proteins with DNA by 2H NMR. Solid state 2D NMR provides valuable information about the movement of various functional groups in an oligonucleotide. Chirukul and coworkers have shown that specific deuteration plays a very significant role in determining such structural features, see Chirakul, et al., Nucleosides, Nucleotides and Nucleic acids, 2001, 20, 1903-1913.

Enzyme recognition with deuterium substitution in place of hydrogen or enzymatic binding is not adversely affected. The enzyme recognition of a particular sequence is the first step in biochemical interaction of oligonucleotides for their specific roles, and deuterium labeling does not change the biochemical process of site recognition. Similarly it is known that hybridization of a double strand is not effected by deuterium labeling, since deuterium and hydrogen atomic radii are very close for any disruption in recognition pattern.

It is expected that multiple covalent labeling of deuterium in place of hydrogen (carbon-hydrogen bonds to carbon-deuterium bond) in the sugar portion of an oligonucleotide slows down the rate of digestion of oligonucleotides which takes place rapidly in cellular environment with exo and endo nucleases. The quick digestion of the oligonucleotide is demonstrated by shorter half life of oligonucleotide and clearance from body. This is much more pronounced in RNA molecules as compared to DNA molecules. The slow digestion of a therapeutic oligonucleotide is expected to add extra advantage to a therapeutic candidate, while other physical or biochemical properties are not affected. Various biochemical effects of deuterated ribo-oligonucleotides is anticipated deuterated oligos are expected to slow digestion of oligonucleotides to smaller fragments, and have no effect with respect to hydrogen bonding, RNAse H editing activity, or recognition by RISC complex. Intracellular hydrolysis or deuterium exchanges my result in liberation of deuterium oxide ($D_2O$).

The enzymatic method of deuterium exchange has been carried out routinely for deuterium labeling. However the exchange method is not complete due to equilibrium which exists in enzymatic reactions. It is anticipated that deuterium labeled oligonucleotides will similarly exchange deuterium with hydrogen within the cellular environment resulting in release of deuterium oxide within the cellular environment. Since deuterium oxide is known as a nutritional agent, oligonucleotides of the instant invention may provide nutritional value.

The use of deuterium exchange for the spectral assignment of nucleosides and oligonucleotides has been carried out quite extensively. Deuteration of the nucleobase residues has been described in exchange of protons at C8-purine and C5-cytosine with deuterioammonium bisulfite at pH 7.8 in deoxyoligomers which gave 90-95% atom $^2$H incorporation. Brush et al. Biochemistry 1988, 27, 115; Brush et al., Am. Chem. Soc. 1998, 110, 4405 described platinum-catalyzed exchange at C5-methyl of thymidine in $^2H_2O$.

A large variety of enzymatic and chemical methods have been developed for deuterium incorporation at both sugar and nucleoside levels to provide high levels of deuterium incorporation (D/H ratio). The enzymatic method of deuterium exchange generally has low levels of incorporation and provides significant levels of stray resonances. Enzymatic incorporation has further complications due to cumbersome isolation techniques which are required for isolation of deuterated mononucleotide blocks. Schmidt et al., Ann. Chem. 1974, 1856; Schmidt et al., Chem. Ber., 1968, 101, 590, describes synthesis of 5',5"-$^2$H2-Adenosine which was prepared from 2',3'-O-isopropylideneadenosine-5'-carboxylic acid or from methyl-2,3-isopropylidene-β-D-ribofuranosiduronic acid, Dupre, M. and Gaudemer, A., Tetrahedron Lett. 1978, 2783. Kintanar, et al., Am. Chem. Soc. 1998, 110, 6367 reported that diastereoisomeric mixtures of 5'-deuterioadenosine and 5'(R/S)-deuteratedthymidine can be obtained with reduction of the appropriate 5'-aldehydes using sodium borodeuteride or lithium aluminum deuteride (98 atom % $^2$H incorporation). Berger et al., Nucleoside & Nucleotides 1987, 6, 395 described the conversion of the 5'-aldehyde derivative of 2' deoxyguanosine to 5' or 4'-deuterio-2'-deoxyguanosine by heating the aldehyde in $^2$H$_2$O/pyridine mixture (1:1) followed by reduction of the aldehyde with NaBD$_4$.

Ajmera et al., Labelled Compd. 1986, 23, 963 described procedures to obtain 4'-Deuterium labeled uridine and thymidine (98 atom % $^2$H). Sinhababu, et al., J. Am. Chem. Soc. 1985, 107, 7628) demonstrated deuterium incorporation at the C3' (97 atom % 2H) of adenosine during sugar synthesis upon stereoselective reduction of 1,2:5,6-di-O-isopropylidene-B-D-hexofuranos-3-ulose to 1,2:5,6-di-O-isopropylidene-3-deuterio-B-D-ribohexofuranose using sodium borodeuteride and subsequently proceeding further to the nucleoside synthesis. Robins, et al., Org. Chem. 1990, 55, 410 reported synthesis of more than 95% atom $^2$H incorporation at C3' of adenosine with virtually complete stereoselectivity upon reduction of the 2'-O-tert-butyldimethylsilyl(TBDMS) 3-ketonucleoside by sodium borodeuteride in acetic acid. David, S. and Eustache, J., Carbohyd. Res. 1971, 16, 46 and David, S, and Eustache, J., Carbohyd. Res. 1971, 20, 319 described syntheses of 2'-deoxy-2'(S)-deuterio-uridine and cytidine. The synthesis was carried out by the use of 1-methyl-2-deoxy-2'-(S)-deuterio ribofuranoside.

Radatus, et al., J. Am. Chem. Soc. 1971, 93, 3086 described chemical procedures for synthesizing 2'-monodeuterated (R or S)-2'-deoxycytidines. These structures were synthesized from selective 2-monodeuterated-2-deoxy-D-riboses, which were obtained upon stereospecific reduction of a 2,3-dehydro-hexopyranose with lithium aluminum deuteride and oxidation of the resulting glycal. Wong et al. J. Am. Chem. Soc. 1978, 100, 3548 reported obtaining -Deoxy-1-deuterio-D-erythro-pentose, 2-deoxy-2(S)-deuterio-D-erythro-pentose and 2-deoxy-1,2(S)-dideuterio-D-erythro-pentose from D-arabinose by a reaction sequence involving the formation and LiAlD$_4$ reduction of ketene dithioacetal derivatives.

Pathak et al. J., Tetrahedron 1986, 42, 5427) reported stereospecific synthesis of all eight 2' or 2"-deuterio-2'-deoxynucleosides by reductive opening of appropriate methyl 2,3-anhydro-β-D-ribo or β-D-lyxofuranosides with LiAlD$_4$ Wu et al. J. Tetrahedron 1987, 43, 2355 described the synthesis of all 2',2"-dideuterio-2'-deoxynucleosides, for both deoxy and ribonucleosides, starting with oxidation of C2' of sugar and subsequent reduction with NaBD$_4$ or LiAlD$_4$ followed by deoxygenation by tributyltin deuteride. Roy et al. J. Am. Chem. Soc. 1986, 108, 1675, reported 2',2"-Dideuterio-2'-deoxyguanosine and thymidine can be prepared from 2-deoxyribose 5-phosphate using 2-deoxyribose 5-phosphate aldolase enzyme in $^2$H$_2$O achieving some 90 atom % deuteration.

Therefore, it is clear that each position of the sugar residue can be selectively labeled. A number of these deuterated nucleosides have been used in solid-state $^2$H-NMR studies on the internal motions of nucleosides and oligonucleotides, see Hiyama et al. J. Am. Chem. Soc. 1989, 111, 8609; Alam, T and Drobny, G. P., Biochemistry, 1990, 29, 3421; Alam et al., Biochemistry, 1990, 29, 9610; Huang et al., J. Am. Chem. Soc. 1990, 112, 9059; Drobny, G. P. et al., Biochemistry, 1991, 30, 9229. In the temperature dependent line shape analysis in solid-state $^2$H-NMR spectroscopy, the stereoselectivity of 2' versus 2" labeling or the level of deuteration does not play a significant role. The use of specifically deuterium labeled nucleotides for the simplification of 1D and 2D $^1$H-NMR spectra in solution studies was not very useful for structural information. However, most extensive use of deuteration in the 1D NMR studies was performed by Danyluk et al. These workers isolated pre-deuterated $^2$H— labeled mononucleotides (~90 atom % $^2$H incorporation) in a tedious manner from RNA digest of blue-green algae grown in $^2$H$_2$O. These pre-deuterated nucleoside blocks were then used to obtain a wide variety of partially deuterated dimers and trimers for the purpose of resonance assignments in 1D $^1$H-NMR spectra (200-300 MHz). Synthesis of 4',5',5"-$^2$H3-adenosine was carried out and this was coupled to appropriately blocked adenosine 3-phosphite to give ApA* (pA* 4',5', 5"-$^2$H3-pA). This dimer allowed the unequivocal measurement of the difference between phosphorus and H-3' (Kondo et l., Am. Cem. Soc. 1972, 94, 5121; Kondo, Labeled Compd. 1973, 9, 497; Ezra, et al., Biochemistry, 1975, 53, 213; Kondo and Danylik., Biochemistry, 1976, 15, 3627; Lee, et al., Biochemistry, 1976, 15, 3627; Ezra, et al., Biochemistry, 1977, 16, 1977. Similarly synthesis of 4',5',5"-$^2$H3-guanosine can be carried out to synthesize guanosine rich oligonucleotides.

A useful alternative method of stereospecific deuteration was developed to synthesize polydeuterated sugars. This method employed exchange of hydrogen with deuterium at the hydroxyl bearing carbon (i.e. methylene and methine protons of hydroxyl bearing carbon) using deuterated Raney nickel catalyst in $^2$H$_2$O. Detailed studies revealed structure dependent difference in exchange rates, high level of epimerization, significantly lower extent of deoxygenation, and difficulties in the reproducibility of the level of deuteration (Balza et al., Res., 1982, 107, 270; Angyal et al. Carbohydr. Res. 1986, 157, 83; Koch et al. Res. 1978, 59, 341; Wu et al. J. Org. Chem. 1983, 48, 1750; and Angyal et al. Res. 1986, 157, 83).

Various techniques are available to synthesize fully deuterated deoxy and ribonucleosides. Thus in one method, exchange reaction of deuterated Raney nickel-$^2$H$_2$O with sugars, a number of deuterated nucleosides specifically labeled at 2,3' and 4' positions were prepared. The procedure consisted of deuteration at 2, 3 and 4 positions of methyl β-D-arabinopyranoside by Raney nickel-$^2$H$_2$O exchange reaction followed by reductive elimination of 2-hydroxyl group by tributyltin deuteride to give methyl β-D-2,2', 3,4-$^2$H$_4$-2-deoxyribopyranoside which was converted to methyl β-D-2,2',3,4-$^2$H4-2-deoxyribofuranoside and glycosylated to give various 2,2',3,4-$^2$H4-nucleosides (>97 atom % $^2$H incorporation for H3' & H4'; ~94 atom % $^2$H incorporation for H2 and H2') (Pathak, T., Chattopadhyaya, J. Tetrahedron 1987, 43, 4227; Koch, H. J., Stuart, R. S., Carbohydr. Res. 1977, 59. C 1; Balza, F., Cyr, N., Hamer, G. K., Perlin, A. S., Koch, H. J., Stuart, R. S., Carbohydr. Res. 1977, 59, C7; Koch, H. J., Stuart, R. S., Carbohydr. Res. 1978, 64, 127; Koch, H. J., Stuart, R. S., Carbohydr. Res. 1978, 59, 341; Balza, F., Perlin, A. S. Carbohydr. Res., 1982, 107, 270; Angyal, S. J., Odier, L. Carbohydr. Res., 1983, 123, 13.; Wu, G. D., Serianni, A. S., Barker, R. J., Org. Chem. 1983, 48, 1750; Angyal, S. J., Stevens, J. D., Odier, L. Carbohydr. Res. 1986, 157, 83; Kline, P. C., Serianni, A. S. Magn. Reson. Chem., 1988, 26, 120; Kline, P. C., Serianni, A. S. Magn. Reson. Chem., 1990, 28, 324; Robins, M. J., Wilson, J. S., Hansske, F., J. Am. Chem. Soc. 1983, 105, 4059.

Methyl β-D-erythrofuranoside, when treated with deuterated Raney Ni, produced methyl β-D-2,3,4(S)-$^2$H3-erythrofuranoside (~75 atom % $^2$H incorporation at C2 and C4(S) positions and 100% atom $^2$H incorporation at C3) (Kline, P. C.; Serianni, A. S. Magn. Reson. Chem., 1988, 26, 120. This sugar was converted to D-3,4,5(S)-$^2$H3-ribose. These nucleosides were subsequently reduced to the corresponding 3',4', 5'(S)-$^2$H3-2'~deoxynucleosides (Koch, H. J.; Stuart, R. S.

Carbohydr. Res. 1978, 64, 127; Kline, P. C., Serianni, A. S., Magn. Reson. Chem., 1990, 28, 324). Similar to compound 3',4',5"(S)-$^2$H3-ribonucleosides, 1',2',3',4',5',5"(S)-$^2$H6-ribonucleosides can be synthesized starting with fully deuterated and appropriately protected ribose.

SUMMARY OF THE INVENTION

Oligonucleotide based therapeutics is a strong component of rational drug design approach and a number of oligonucleotides are currently in the market or at various stages of clinical trials. Previously, deuterium modified nucleosides have been synthesized at specific positions of deoxy-sugars and purine and pyrimidine bases. Deuterated DNA synthons based on phosphotriester technology or phosphoramidite have been synthesized and utilized for synthesis of defined sequence oligonucleotides. These studies have been directed solely for the purpose of conformational studies of DNA and RNA, determination of active site for enzyme assisted catalytic reactions. However deuterated oligonucleotides have not been investigated for therapeutic application in humans or the role which they can elicit as biological and biochemical agents.

The instant invention describes deuterium labeled phosphoamidites, ribose units having solid support caps, oligonucleotides, a process for synthesizing deuterium labeled nucleosides and oligonucleotides, and a process for synthesizing deuterated nucleosides and oligonucleotides which contain deuterium ranging from 0.1% to 98% per position is envisaged. Once a known percentage of deuterium has been incorporated in the nucleoside, such nucleosides can further be modified in subsequent steps until the synthesis of the phosphoramidites or solid support bound nucleosides for solid phase oligonucleotide synthesis occurs. The deuterium ratio of 0.1 to 98% in further steps will be maintained. Such specific and controlled deuteration has not been proposed or carried out in past to the best of our knowledge. The deuterated ribo-oligonucleotides formed provide RNA sequences with enhanced stability.

Deuterium labeling of an oligonucleotide is not expected to present toxic effects. Selective deuterium modified oligonucleotides either in selected positions of sugar, purine, pyrimidine bases or total deuteration of sugar positions and nucleobases will contribute to the improvement of biological properties of oligonucleotides. Oligonucleosides specifically deuterated in various positions of the sugar portion of the ribose are expected to increase enzymatic stabilities and substantially increase stability of a therapeutic oligonucleotide. Deuterium substitution is not known to affect the enzyme recognition or enzymatic binding. Site specific atom transfer has been utilized for structural information of cleavage of a specifically deuterium labeled dodecamer, see Voss, et al., *J. Am. Chem. Soc.*, 1990, 112, 9669-9670. The enzyme recognition of a particular sequence is the first step in biochemical interaction of oligonucleotides for their specific roles, and deuterium labeling does not change the biochemical process of site recognition. Similarly hybridization of a double strand is not affected by deuterium labeling.

It is anticipated that deuterium labeled oligonucleotides will not affect the hydrogen bonding with a complementary strand either by Watson Crick base pairing mechanism, Hoogsten or other hybridization mechanisms applicable to DNA/DNA hybridization, DNA/RNA hybridization, RNA/RNA hybridization. RNAse H cleavage between deuterated DNA with complementary RNA, which is involved in anti-sense based oligo-therapeutic approach, is not expected to be affected by the presence of deuterium covalently attached to the sugar backbone or nucleobases. Thus deuterium labeled oligonucleotides should play a role in the anti-sense mode of therapeutic action. Additionally, it should be possible to develop deuterated siRNAs for therapeutic application. Based on the various schemes presented for synthesis of ribonucleosides and oligonucleotides with one or more deuterium in a nucleoside of an oligo nucleotide chain, it is anticipated that designing aptamers with selective or fully deuterated RNA sequences can be accomplished. The chemical method of synthesis and deuterium labeling in nucleosides will be done in sugar and nucleobases at positions which are stable and non-exchangeable in general, such as at the carbon hydrogen bonds (C—H). However within the cell there is expected to be slow exchange of deuterium with hydrogen with slight basic pH. Due to slow release of deuterium by exchange mechanism in vivo (C-D→C—H), such deuterium labeled oligonucleotides will offer the advantage of nutritionally beneficial effects. Deuterium labeled oligonucleotides, therefore, may have enormous potential to replace therapeutic oligonucleotides which have natural hydrogen atoms in various non-ionizable positions of nucleosides and in oligonucleotides. In order to determine the effect of specific levels of deuteration in nucleosides of an oligonucleotide, a very low level deuteration such as 0.1% all the way up to 98% deuteration of a specific covalent carbon hydrogen bond will be carried out and such oligonucleotides will be studied for its biochemical and biological effects and roles. Such systematic biological study will provide better guidance to development of drugs and therapeutics. Such studies have not been proposed or carried out to the best of our knowledge.

As used herein, the term "oligonucleotides" refers to a plurality of nucleotides joined together in a specific sequence defined by the natural or modified heterocyclic base moieties. Representative heterocyclic base moieties include, but are not limited to, nucleobases such as adenine, guanine, cytosine, uracil, as well as other non-naturally-occurring and natural nucleobases such as xanthine, hypoxanthine, 2-aminoadenine, 2,6-diamino purine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine, 7-deazaadenine, 7-deazaguanine. Modified nucleobases as described herein define synthetic nucleobases or nucleobases that have been changed from their naturally occurring state, such as deuteratedadenine, deuteratedcytosine, deuteratedguanine, and deuterateduracil.

Accordingly, it is a primary objective of the present invention to teach deuterated nucleosides, phosphoramidites and oligonucleotides, a process of synthesizing fully deuterated phosphoramidites and oligonucleotides, and a process of synthesizing deuterated phosphoramidites and oligonucleotides containing 0.1%-98% deuterium at various positions.

It is a further objective of the present invention to teach a process of making derivatized ribo nucleoside and phosphoramidites with deuterium labeled covalently at various positions of nucleosides and products made thereof.

It is a further objective of the present invention to teach ribonucleosides and phosphoramidites with deuterium labeled covalently at various positions of nucleosides.

It is a still further objective of the present invention to teach the process of making deuterium labeled oligoribonucleotides with natural phosphodiester backbone, and products made thereof.

It is a still further objective of the present invention to teach deuterium labeled oligoribonucleotides with natural phosphodiester backbone.

It is yet another objective of the present invention to teach the process of making deuterium labeled oligoribonucleotides with phosphothioate backbone, and products made thereof.

It is a still further objective of the present invention to teach deuterium labeled oligoribonucleotides with variant backbones.

It is yet another objective of the present invention to teach deuterium labeled oligoribonucleotides with phosphothioate backbone.

It is another objective to the present invention to teach oligonucleotides that have stability enhancing deuterated backbones.

It is yet another objective of the present invention to teach deuterated oligonucleotides useful for therapeutic treatments.

It is another objective to the present invention to teach deuterated RNA antisense oligonucleotides useful for therapeutic treatments.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2 illustrates Scheme 1, synthesis of 1-O-Acetate-α/β2,3,5-O-tribenzoyl-1-2,3,4,5,5'pentadeuterium-D ribofuranoside;

FIG. 3 illustrates Scheme 2,5'-O-dimethoxytrityl-2'-O-tert-Butyldimethylsilyl-2',3',4',5',5"penta deuterium 3'-Cyanoethyl n,n-diisopropyl phosphoramidite-β-D ribofuranosyl-Uridine;

FIG. 4 illustrates Scheme 3, synthesis of 5'-O-dimethoxytrityl-2'-O-tert-Butyldimethylsilyl-3'-succinyl Icaa-CPG-2',3',4',5',5"penta deuterium β-D ribofuranosyl) Uridine;

FIG. 5 illustrates Scheme 4, synthesis of 5'-O-dimetoxytrityl-2'-O-terbutyldimethyl Silyl-3'-N,N-diisopropyl cyanoethyl phosphoramidite-2',3',4',5',5"penta deuterium β-D ribofuranosyl-N⁴ benzoyl Cytidine;

FIG. 6 illustrates Scheme 5, synthesis of 5'-O-dimethoxytrityl-2'-O-tert-Butyldimethylsilyl-3'-succinyl Icaa-CPG-2',3',4',5',5"penta deuterium β-D ribofuranosyl-N⁴ benzoyl Cytidine;

FIG. 7 illustrates Scheme 6, synthesis of an alternative embodiment of a modified phosphoramidite in accordance with the instant invention, illustrated as 5'-O-dimethoxytrityl-2',3',4',5',5"penta deuterium-β-D ribofuranosyl-N⁶ benzoyl adenosine;

FIG. 8 illustrates Structure C1, a representative illustration of a particular embodiment of a deuterated oligonucleotide in accordance with the instant invention;

FIG. 9A illustrates Structure D1, an alternative embodiment of the deuterated oligonucleotide having a phosphodiester internucleotide linkage;

FIG. 9B illustrates Structure D2, an alternative embodiment of the deuterated oligonucleotide having a phosphate backbone variant, illustrated as phosphorothioate internucleotide linkage;

FIG. 10 is a summary chart of an HPLC analysis of the deuterated nucleosides and phosphoramidites, using a Shimazdu, Model, HPLC Column: Chromsep SS (4.6×250 mm) with Chrosep Guard column Omnisphere 5 C18;

FIG. 13B is a HPLC report of 2',3',5'-tri-hydroxy-2',3',4',5',5"penta deuterium β-D ribofuranosyl-Uridine (structure IX);

FIG. 13C is a mass spectrum of 2',3',5'-tri-hydroxy-2',3',4',5',5"penta deuterium β-D ribofuranosyl-Uridine (structure IX); Calculated mass: 249.10; Observed Mass: 247.30;

FIG. 14B is ¹H-NMR spectrum of 5'-O-dimethoxy trityl-2',3',4',5',5"penta deuterium β-D ribofuranosyl-Uridine (Structure X);

FIG. 15B is a HPLC chromatogram of 5'-O-dimethoxytrityl-2'-O-tert-Butyldimethylsilyl-2',3',4',5',5"penta deuterium β-D ribofuranosyl-Uridine; (structure XI);

FIG. 16B is HPLC report of 5'-O-dimethoxytrityl-2'-O-tert-Butyldimethylsilyl-3'-N,N-diisopropyl cyanoethyl phosphoramidite-2',3',4',5',5"penta deuterium β-D ribofuranosyl Uridine (structure XIII); Purity: 96.72%;

FIG. 16D is a UV analysis report of 5'-O-dimethoxytrityl-2'-O-tert-Butyldimethylsilyl-3'-N,N-diisopropyl cyanoethyl phosphoramidite-2',3',4',5',5"penta deuterium β-D ribofuranosyl Uridine (structure XIII);

FIG. 17B is a HPLC report of 5'-O-dimetoxytrityl-2'-O-terbutyldimethyl Silyl-2',3',4',5',5"penta deuterium β-D ribofuranosyl-N$^4$ Benzoyl Cytidine (structure XIV);

FIG. 18B is a 1H-NMR spectrum of 2',3',5'-tri Hydroxy-2',3',5',5"penta deuterium β-D ribofuranosyl-N$^4$ benzoyl Cytidine (structure XVIII);

FIG. 19B is a HPLC report of 5'-O-dimethoxytrityl-2',3',4',5',5"penta deuterium β-D ribofuranosyl-N$^4$ Benzoyl Cytidine (compound XIX);

FIG. 20B is a: HPLC report of 5'-O-dimetoxytrityl-2'-O-terbutyldimethyl Silyl-3'-N,N-diisopropyl cyanoethyl phosphoramidite-2',3',4',5',5"penta deuterium β-D ribofuranosyl-N$^4$ benzoyl Cytidine (structure XXII); Purity: 78.88%;

FIG. 20D is a UV analysis of 5'-O-dimethoxytrityl-2'-O-terbutyldimethyl Silyl-3'-N,N-diisopropyl cyanoethyl phosphoramidite-2',3',4',5',5"penta deuterium β-D ribofuranosyl-N$^4$ benzoyl Cytidine (structure XXII);

FIG. 22B is a HPLC chromatogram of 5'-O-dimethoxy trityl-2'3',4',5',5"-penta deuterium β-D ribofuranosyl-N$^6$ benzoyl Adenosine (structure XXVIII);

FIG. 23B is a capillary electrophoresis report of the purified oligonucleotide SEQ ID No.1, fully deuterated RNA;

FIG. 24B is a capillary electrophoresis report of the purified oligonucleotide SEQ ID No.2, approx. 25% deuterated RNA;

FIG. 25B is a capillary electrophoresis report of the purified oligonucleotide SEQ ID No.3 natural RNA;

FIG. 26B is a capillary electrophoresis report of the purified oligonucleotide SEQ ID No.4 natural RNA;

FIG. 27B is a capillary electrophoresis report of the purified oligonucleotide SEQ ID No.5 natural RNA.

DETAILED DESCRIPTION OF THE INVENTION

Figure 1C:
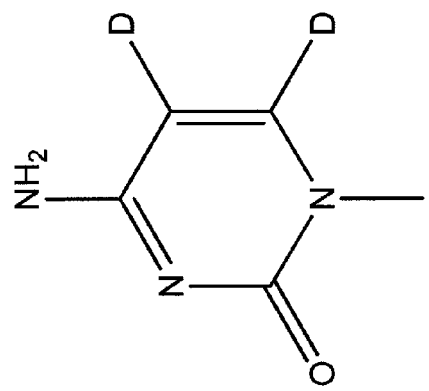
FIG. 1C is a chemical structure of a modified nucleobase, illustrated as deuteratedcytosine.

The instant invention describes high purity deuterated ribose and sugars, deuterated ribose-based nucleotides, deuterated RNA oligonucleotides, and controlled processes for synthesizing deuterium incorporated oligonucleotides for use in therapeutics. The controlled process would entail a method of development for various selected deuteration ranging from 0.1% to 98%, and analytical methods to ascertain the reaction conditions. The synthesis process provides deuterated oligonucleotides containing deuterium ranging from 0.1% per position to 98% per position. After incorporation of deuterium in varying percentages within nucleoside, further chemical synthesis will be performed to produce phosphoramidites which will maintain the percent deuterium at each step till the step of phosphoramidite. Subsequently such fixed ratio D/H oligonucleotide synthons will be used to produce oligonucleotide. Once the percent incorporation of deuterium has been determined by various analytical methods such as proton NMR and mass spectroscopy, the ratio of deuterium/ hydrogen will not be affected if proper choice of reaction conditions is maintained. The instant invention further describes the selected examples controlled synthesis of deuterium labeled nucleoside-3'-succinate nucleosides with partial or full saturation of deuterium label which varies from 0.1%-98% deuterium at specific positions of the sugar and purine/pyrimidine bases for use in solid phase oligonucleotide synthesis. Therefore, the instant oligonucleotide synthesis process is carried out similar to conventional oligonucleotide synthesis, i.e. from the 3'-end to 5'-end direction.

The deuterated ribose and sugars, deuterated ribose-based nucleotides, deuterated RNA oligonucleotides of the present invention may therefore be used for therapeutic benefits. Oligonucleotide therapy, i.e., the use of oligonucleotides to modulate the expression of specific genes, offers an opportunity to selectively modify the expression of genes without the undesirable non-specific toxic effects of more traditional therapeutics. In an illustrative example, the deuterated ribose and sugars, deuterated ribose-based nucleotides, deuterated RNA oligonucleotides of the present invention may be used in antisense therapies. The present invention therefore may be used to provide a modified antisense RNA with enhanced protection to provide a more stable, not easily digested, antisense RNA. The oligonucleotides of the present invention can therefore be used in clinical practice for any disease and against any target RNA for which antisense therapy is now known to be suitable or which is yet to be identified. The deuterated oligonucleotides of the present invention may be used for other nucleic based molecule therapies including silencing gene expression at the mRNA level with nucleic acid-based molecules, such as RNA interference.

Several illustrative steps for synthesizing deuterium nucleoside, sugar and base protection, phosphoramidites and the corresponding oligonucleotide contemplated are described below. Synthesis of sugar deuterium protected nucleosides involves selective deuteration of non-exchangeable protons, such as H-1, H-2, H-3, H-4 and H-5,5' of B-D-ribose. The H-1' and H-4' protons are slightly acidic in nature when they become part of nucleoside and have the tendency to get exchanged to a certain extent with hydrogen. As a result, these two protons do not give greater than 90% D/H ratio. While the protons H-2', H-3', H-5',5" have higher pK, and hence can be deuterated to greater than 95% of D/H ratio, they do not readily exchange back to hydrogen in protic medium during reaction or when in contact with slightly basic pH conditions The present invention discloses a modified phosphoramidite having the structure of Structure A:

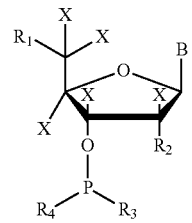

wherein X or X1 represents deuterium or hydrogen, R1 represents a blocking group, R2 independently represents a blocking group, R3 is a phosphate protecting group, preferably cyanoethyl dialkylamino, and R4 is a independently a protecting group, preferably 3'B-cyanoethyl protecting group, and B represents a nucleobase. Although 1' position of the ribose sugar is also deuterated, however the extent of deuterium can be variable at this position and can be exchanged for H after being deuterated. Therefore, the 1' position is illustrated as D/H in the Figures. From our data the deuterium incorporation at this position is approx. 50:50: deuterium: hydrogen. Therefore in our further discussions if deuterium incorporation is reduced to a lower deuterium in our formulations, the deuterium enrichment at 1' position will become almost 50% of the rest of the position as compared to deuteration in other positions of ribose ring. The deuterium at the 4' position could be variable as well.

The blocking, or protecting group, generally renders a chemical functionality of a molecule inert to specific reaction conditions and can later be removed from such functionality in a molecule without substantially damaging the remainder of the molecule. As part of the oligonucleotide process, functional groups on the nucleobases and the 2' sugar group can are blocked. Hydroxyl protecting groups according to the present invention include a wide variety of groups. Preferably, the protecting group is stable under basic conditions but can be removed under acidic conditions. Preferably, R1 (5' hydroxyl group) is dimethoxytrityl (DMT). Other representative hydroxyl protecting groups include, but are not limited to trityl, monomethoxytrityl, trimethoxytrityl, 9-phenylxanthen-9-yl (Pixyl) and 9-(p-methoxyphenyl)xanthen-9-yl (Mox). Preferably, R2 (2' hydroxy group) is protected with t-butyldimethylsilyl (TBDMS). Other groups, such as with t-butyldimethylsilyloxymethyl (TOM) group may be used as well. The phosphate protecting group functions to protect the phosphorus containing internucleotide linkage or linkages during, for example, solid phase oligonucleotide synthetic regimes. Treatment of the internucleotide linkage or linkages that have a phosphorus protecting group thereon with a deprotecting agent, such as aqueous ammonium hydroxide, will result in the removal of the phosphorus protecting group and leave a hydroxyl or thiol group in its place. In addition to those listed above, other protecting groups such as, but not limited to diphenylsilylethyl, delta.-cyanobutenyl, cyano p-xylyl (CPX), methyl-N-trifluoroacetyl ethyl (META) and acetoxy phenoxy ethyl (APOE) group can be used as well.

Figure 1D:
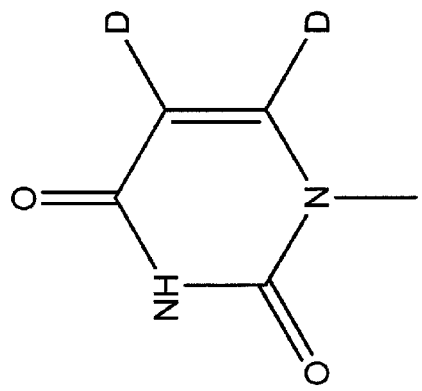
FIG. 1D is a chemical structure of a modified nucleobase, illustrated as deuterateduracil.
Figure 1A:
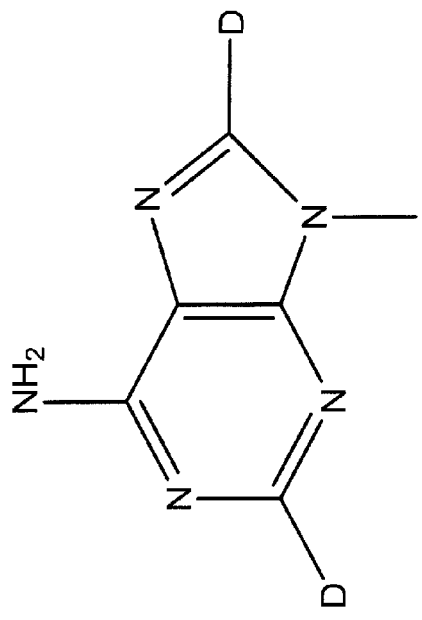
FIG. 1A is a chemical structure of a modified nucleobase, illustrated as deuteratedadenine.
Figure 1B:
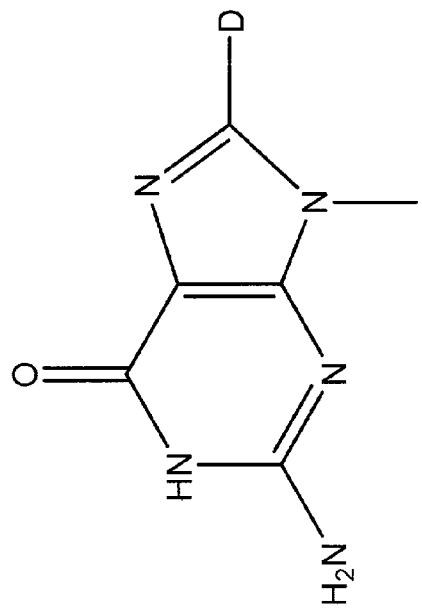
FIG. 1B is a chemical structure of a modified nucleobase, illustrated as deuteratedguanine.
Figure 11A:
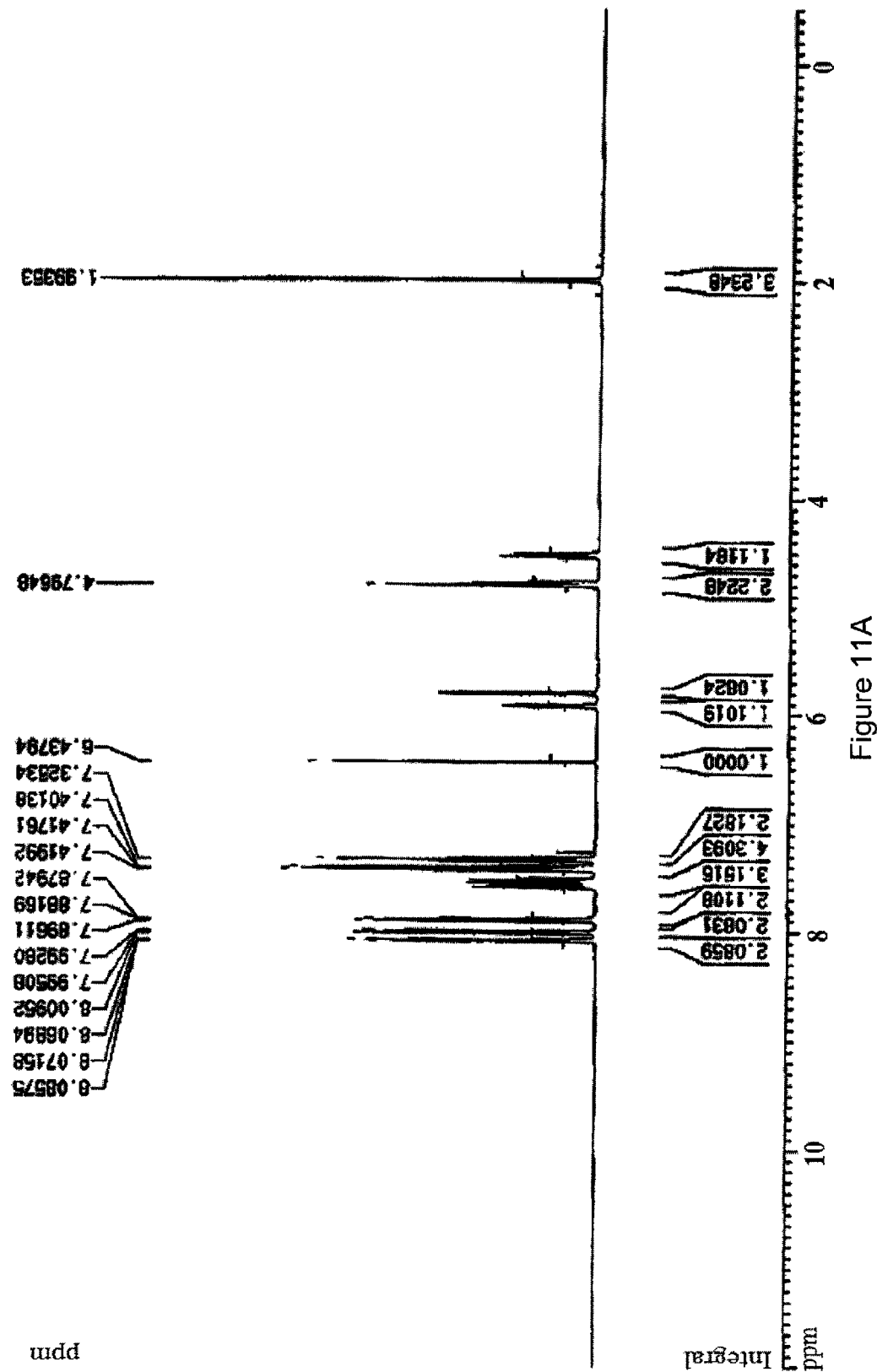
FIG. 11A is 1H-NMR spectrum of 1-O-Acetate-α/β2,3,5tribenzoyl ribofuranoside.
Figure 11B:
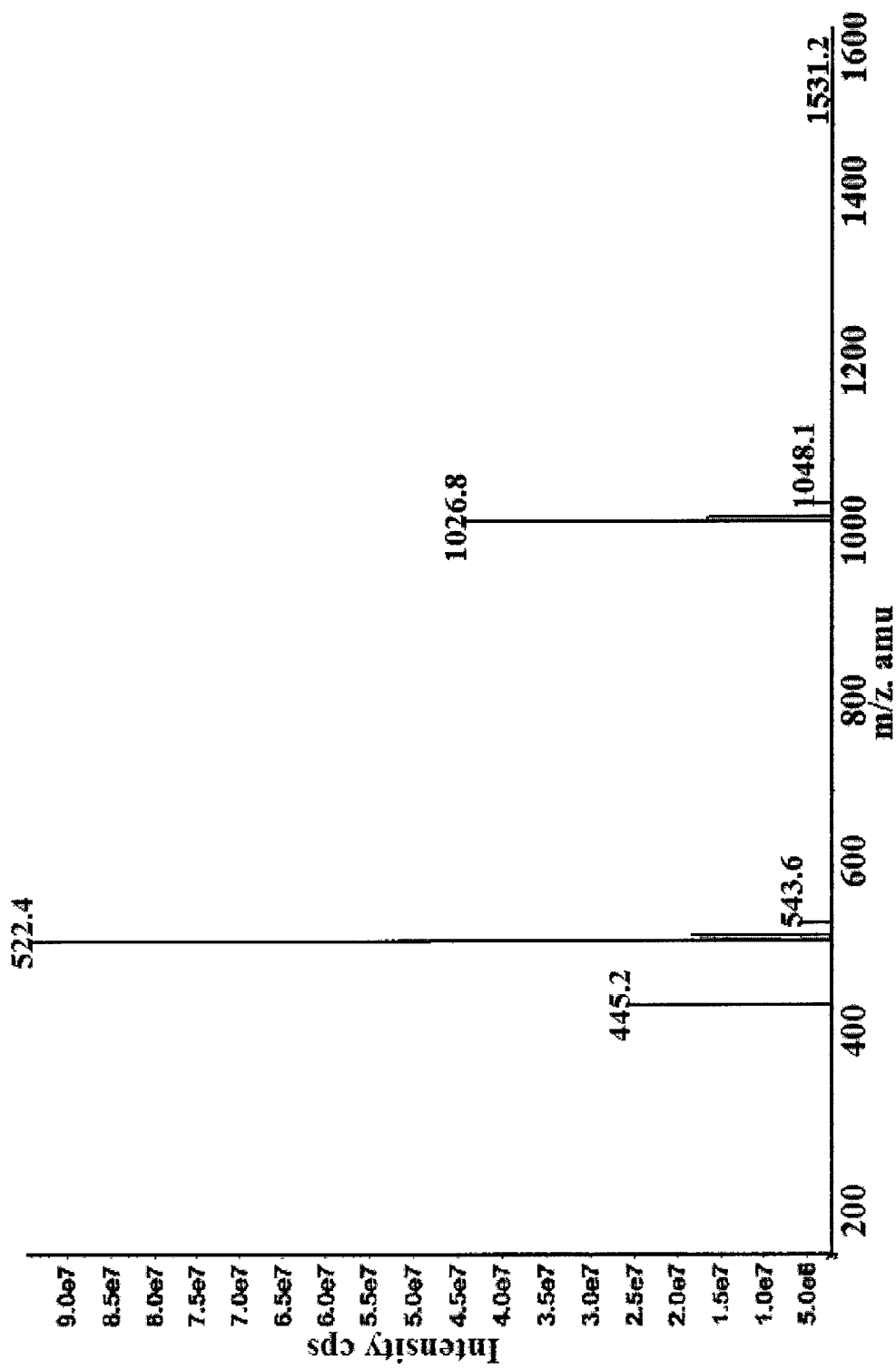
FIG. 11B is a positive ion mss spectrum of 1-O-Acetate-α/β2,3,5tribenzoyl ribofuranoside; Lot#: SK38-38, Calculated mass: 504.14; Observed Mass: 522.40.

The nucleobase B may be natural bases, such as adenine, guanine, cytosine, or uracil. B may also be modified bases, such as deuteratedadenine, see FIG. 1A, deuteratedguanine, see FIG. 1B, deuteratedcytosine, see FIG. 1C, deuteratureduracil, see FIG. 1D, or other modified bases known to one of skill in the art, including or analogs of natural bases, synthetic bases, and modified bases such as, but not limited, to hypoxanthine (inosine), 5-methylcytosine, 5-azacytosine, 5-halogenated uracil and cytosine, and 5-alky-substituted nucleobases such as C-5 propyne uracil and C-5 propyne cytosine, which have also been deuterated. B may also contain a blocking group, such as benzoyl protecting group, or isobutyryl protecting group, acetyl protecting group, phenoxyacetyl protecting group, 4-isopropylphenoxyacetyl protecting group, or dimethylformamidino, dimethylacetaminidine protecting group.

Figure 12A:
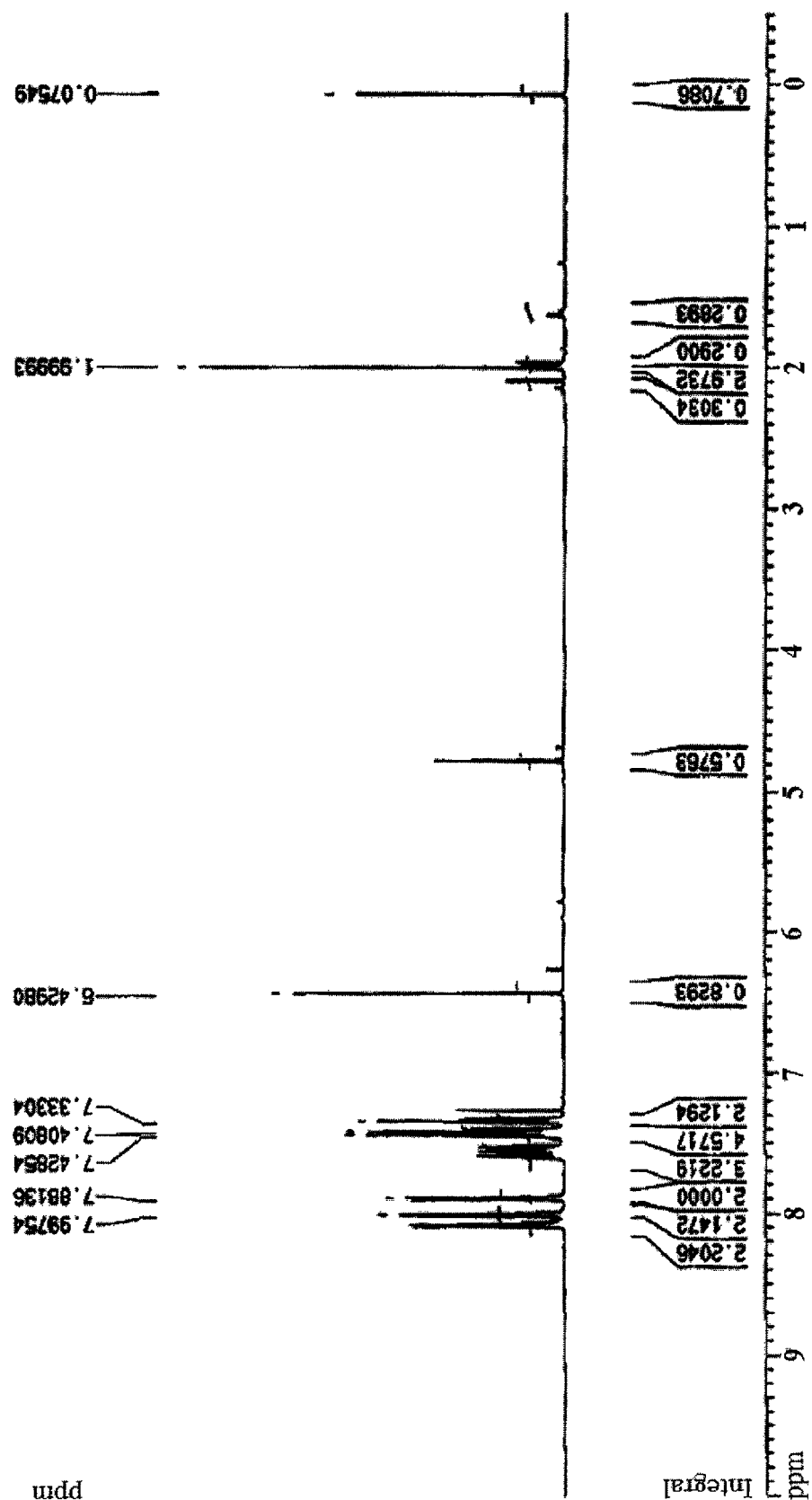
FIG. 12A is a ¹H-NMR spectrum of 1-O-Acetate-α/β2,3,5-tribenzoyl-2,3,4,5,5'pentadeuterium-D ribofuranoside (structure VI), with the H-4 proton shown at approx. 50% intensity, thereby indicating approx. 50% deuterium incorporation at this position.
Figure 12B:
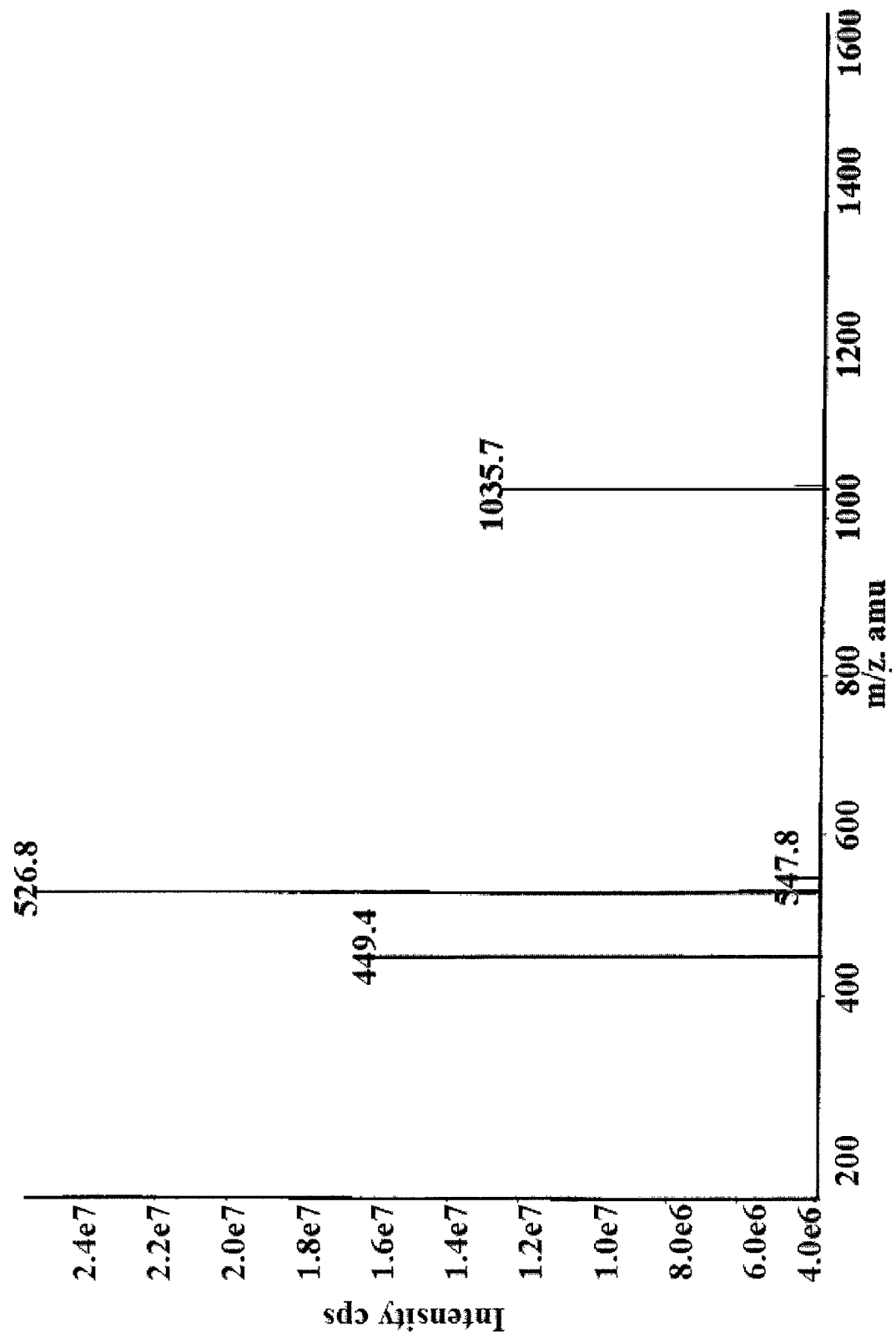
FIG. 12B is a positive ion mass spectrum of 1-O-Acetate-α/β2,3,5-tribenzoyl-1-2,3,4,5,5'pentadeuterium-D ribofuranoside (VI); Calculated mass: 509.17; Observed Mass: 526.80 (M+Sodium)

FIG. 2 describes the synthesis of an illustrative example of a starting material in the process of synthesizing deuterated RNA-nucleosides, n-protected phosphoramidites, and oligonucleotides. The synthesis of the 1-O-Acetate-α/β2,3,5-O-tribenzoyl-1-2,3,4,5,5'pentadeuterium-D ribofuranoside, structure VI was carried out according to the Scheme, starting with α/β-D ribofuranoside (-D-Ribose; structure I). Deuterium was introduced by slight modification of the procedure described by A. Foldesi, F. R. Nilson, C. Glemarec, C. Gioeli & J. Chattopadhyaya, Tetrahedron, 9033, 1992. Procedure for synthesis of deuterated Raney Nickel was also adopted from the same authors in the reference cited here with slight modification to improve the efficiency of deuterium incorporation. The steps involved synthesis of 1-O-methyl-α/β-D ribofuranoside (II) from D-Ribose (I). 1-O-methyl α/β2,3,4,5,5'pentadeuterium-D ribofuranoside (III) was synthesized from compound II with deuterated Raney Nickel. 1-O-methyl-α/β2,3,5-tribenzoyl-2,3,4,5,5'pentadeuterium-D ribofuranoside (IV) was synthesized from compound having structure III by carrying out benzoylation under mild conditions. 1-Bromo-α/βD 2,3,5-tribenzoyl-2,3,4,5,5'pentadeuterium-D ribofuranoside (V) was synthesized from compound IV first by selective removal of 1-O-methyl group to generate 1-hydroxyl sugar which was subsequently replaced by bromine without isolation of the intermediate 1-hydroxyl sugar. The compound V was proceeded directly without purification for the synthesis of 1-O-Acetate-α/β2,3,5-tribenzoyl-2,3,4,5, 5'pentadeuterium-D ribofuranoside (VI). Compound VI was crystallized and fully characterized by 1H NMR, see FIG. 12A. The percent deuterium incorporated at each sugar position was confirmed from this analysis and the sugar was further characterized by Mass spectral analysis, see FIG. 12B.

Synthesis of 1-O-Acetate-α/β2,3,4,5-O-tribenzoyl-2,3, 4,5,5'pentadeuterium-D ribofuranoside, Scheme 1

Preparation of Deuterium Raney-Nickel Catalyst: Deionized water, 192 mL was placed in a 500 ml Erlenmeyer flask equipped with a thermometer and Teflon coated magnetic stirrer. The Erlenmeyer flask was placed inside a plastic beaker which was half filled with water and located on top of a hot plate/magnetic stirrer. Sodium hydroxide pellets (51.2 g was slowly added into the water within the flask while gently stirring. The gentle stirring maintained the water temperature to about 50° Celsius (C). The mixture was stirred until al all the sodium hydroxide (NaOH) pellets had dissolved. Prior to adding additional chemicals, the temperature inside flask was maintained at approximately 50° C. Subsequently raney nickel alloy, (Sigma Aldrich) 40 g was gradually added in small portions within 30 minute time frame. The temperature of water outside, i.e. within the beaker, was maintained at approximately 50° C. +/−4° C. After addition of the Raney Nickel Alloy, the composition was stirred for approximately 60 minutes while maintaining the inside temperature. Subsequently, the reaction flask was cooled down slowly to room temperature, taking approximately 1 hour. Deionized water was added to the flask 1 liter at a time and carefully decanted out. This process was repeated two additional times for a total of 3 times. During each of the water additions and decanting, all solid materials was left within the flask. After completion of the 3 water and decanting steps, the solid was transferred to a 500 ml filtration flask. A tube was connected to the filtration flask to remove any over flown water created while deionized water was added to the top of the filtration flask. The contents of the filtration flask was continuously washed and stirred until all turbidity was gone. Once the turbidity was gone, additional washing with deionized water was continued using approximately 20 liters of deionized water. Washing was terminated upon the water having a pH 6.5-7.0 and the supernatant was clear.

Deuterated Raney Nickel catalyst was subsequently prepared. The catalyst particles after washing were transferred into a septum capped bottle. Teflon coated magnetic stirrer was placed in the bottle and a rubber stopper was placed on top of the septum bottle. The bottle was purged with Argon. The suspension was stirred for 1 minute, after which the particles were allowed to settle. Water was carefully removed using Pasteur-pipette. This process was carried out 4 times, each time requiring addition of by adding 1.5 ml deionized water, stirring, and careful removal of the water. Subsequently deuterium oxide ($D_2O$, 1.5 ml; Cambridge Isotope Labs., Massachusetts, purity greater than 98%) was added. The mixture was stirred for 30 minutes. After the solid settled to the bottom, the liquid was carefully removed by pipette. The process was repeated two additional times, adding additional deuterium oxide ($D_2O$, 1.5 ml) and stirring for 30 minutes. Each time the septum capped bottle was opened and reagents added, the bottle was flushed with Argon and quickly sealed with septum. After three times, 3 ml of $D_2O$ was added. Then mixture was stirred for 1 hour, followed by removal of the supernatant. This process was repeated 12 additional times, each time purging the bottle with Argon. The mixture was treated with $D_2O$ (10 ml) and kept sealed overnight after purging with Argon. The supernatant was carefully removed, followed by addition of fresh $D_2O$ (10 ml) in the same manner. The supernatant was decanted out.

Synthesis of 1-O-methyl α/β2,3,4,5,5'pentadeuterium-D ribofuranoside (Structure III): To 8 grams of 1-O-methyl-α/β-D ribofuranoside 10 ml of D2O (10 ml) was added. The solution was evaporated on a rotavapor. This process was repeated two additional time using 10 ml D2O each time. The residue was dissolved in 160 ml of D2O. Deuterated Raney Nickel (40 ml) was transferred into the solution. Argon was bubbled into the reaction mixture for 10 minutes. The reaction mixture was then maintained on an oil bath at 110° C. for 7 days under Argon atmosphere. The reaction mixture was cooled to room temperature and filtered through a bed of celite and washed with a small volume of deionized water.

The filtrate was evaporated on a rotavapor. The residue was co-evaporated with pyridine three times, and dried an additional 6 hours using a direct vacuum line. The process yielded 6.8 g of oily product.

Synthesis of 1-O-methyl-α/β2,3,5-tribenzoyl-2,3,4,5,5'pentadeuterium-D ribofuranoside (Structure IV): Dried 1-O-methyl-α/β2,3,4,5,5'pentadeuterium-D ribofuranoside (III, 6.8 g was) was placed in a round bottom three neck flask and set up with a pressure equalizing funnel and a magnetic stirrer. Dry distilled dichloromethane (34.1 ml) was added. The reaction mixture was stirred. Dry pyridine (68.2 ml) was then added. The solution was stirred at zero degrees Celsius. Subsequently, benzoyl chloride (21.2 ml) was added drop wise through pressure equalizing funnel in the sealed reaction flask. After addition of the benzoyl chloride, the pressure equalizing funnel was removed and replaced with a stopper. The mixture was kept in a sealed polyethylene bag at 0-4° C. in a refrigerator for 48 hours. The reaction was poured on ice and water mixture and the reaction mixture kept for 1 hour. The gummy material was extracted with chloroform, washed with chilled (0-5° C.) saturated sodium bicarbonate solution, followed by a brine solution. The organic layer passed through anhydrous sodium sulfate, and the solution was evaporated on a rotavapor. The residue was subsequently co-evaporated with pyridine, followed by addition with thy toluene. Further drying, 1 undertaken on direct vacuum line, was performed for 6 hours. An oily product was obtained and used to synthesize 1-Bromo-α/βD-2,3,5-tribenzoyl-2,3,4,5,5'pentadeuterium-D ribofuranoside.

Synthesis of 1-Bromo-α/βD 2,3,5-tribenzoyl-2,3,4,5,5'pentadeuterium-D ribofuranoside (Structure V): Toluene dried 1-O-methyl-α/β2,3,5-tribenzoyl-2,3,4,5,5'pentadeuterium-D ribofuranoside (IV) was dissolved in a solution of 33% hydrogen bromide (HBr) made in glacial acetic acid and sealed tightly. The solution was stirred at room temperature. After 30 minutes, the reaction mixture was cooled to 8-10° C. Subsequently, the glacial acetic acid (200 ml) was added to the reaction mixture. Deionized water (130 ml) was then added in a drop wise manner. The reaction mixture was stirred for 23 minutes. The reaction mixture was poured on 5-10° C. cooled deionized water. The gummy mass was extracted with chloroform. Chilled (0-5° C.) aqueous sodium bicarbonate solution was added to the organic layer until the pH of the organic layer was basic (pH>8). The organic layer was separated and washed with chilled aqueous sodium bicarbonate solution once again, followed by passing the organic layer over anhydrous sodium sulfate. The filtered solution was evaporated on a rotary evaporator. The gummy solid was co-evaporated with dry pyridine two times. An oily product was obtained and used in next step.

Synthesis of 1-O-Acetate-α/β2,3,5-tribenzoyl-2,3,4,5,5'pentadeuterium-D ribofuranoside (Structure VI): The dried product, 1-Bromo-α/β2,3,5-tribenzoyl-2,3,4,5,5'pentadeuterium-D ribofuranoside (Structure V) obtained in the proceeding step was taken in dry pyridine (40 ml) and dry distilled in chloroform (40 ml). To the reaction mixture, acetic anhydride (13.9 ml) was added. The solution was mixed gently, sealed and stored at room temperature for 72 hours. The solution was then diluted with chloroform. The total organic layer was placed in a separatory funnel and washed with saturated aqueous sodium bicarbonate solution once, followed by washing with saturated brine solution. The organic layer was passed over anhydrous sodium sulfate, followed by evaporation on a rotary evaporator. The residue was co-evaporated with toluene three times. The gummy mass was dried using a direct vacuum line for 2 hours. Anhydrous ethanol was added to the gummy mass. The solution was kept at 4° C. for 2 hours. The solid obtained was filtered and washed with cold ethanol. The solid was transferred in a round bottom flask and dried on high vacuum direct line at 37° C. for 12 hours. The processes resulted in a yield of 4.5 grams of an off white product. The product was analyzed by 1H NMR and Mass spectral analysis.

Referring to FIGS. 3, 5 and 7, the synthesis of modified phosphoramidites are illustrated and carried out according to Schemes 4, 6 and 8 respectively and the individual steps outlined in below. FIGS. 3, 5 and 7 show illustrative examples of phosphoramidites having nucleobases uracil, cytosine, and adenine. Phosphoramidites having other nucleobases such as guanine or modified nucleobases can be synthesized using the same or similar steps. Accordingly, the following examples are illustrative only and not meant to be limiting.

Synthesis of 2',3',5'-tri-hydroxy-2',3',4',5',5''penta deuterium β-D ribofuranosy Uridine (Structure IX): A mixture of Uracil (compound VII; 0.5 gm; 4.46 mmole), hexamethyl disilazane (15 ml) and ammonium sulphate (20 mg 0.15 mmol) was boiled under reflux until the Uracil was dissolved, approximately 15 hours. Subsequently, hexamethyldisilazane was evaporated under vacuum & toluene is added. The mixture was shaken and solvents were evaporated out to obtain a residual solid consisting of trimethyl silylated uracil. The solid residue was used without purification for coupling. Freshly distilled 1,2dichloro ethane (freshly distilled over $CaH_2$), (16 ml) was to the residue. The mixture was stirred at 40° C., followed by addition of stannic chloride (1.13 ml; 1.46 mmole) at the 40° C. temperature. The reaction was continued for 15 minutes at 40° C. Deuterated 1-acetate α/β-D ribofuranoside (structure VI; 1.81 gm; 3.56 mmol) solution in 1,2dichloro ethane (freshly distilled over $CaH_2$) was placed in a pressure equalizing funnel and mounted on top of the reaction flask above. The solution was added drop wise and the reaction was boiled under reflux for 2.5 hr. The reaction mixture was cooled and stirred in a saturated sodium bicarbonate solution for 1.5 hr. The reaction mixture was filtered through a bed of celite powder. The organic layer was separated and passed through anhydrous sodium sulphate. The reaction mixture was evaporated under vacuum. And checked TLC in chloroform:methanol (8:2). A gummy mass obtained was chromatographed on a column (1.5"X 14 cm) of silica (70:230 mesh) (100 gm) with EtOAc:Hexane (6:4) as an eluant. Fractions were monitored by TLC. The $R_f$ value was 0.46 in chloroform:methanol (8:2). Pure fractions monitored by UV visualization, combined, concentrated on rotary evaporator and the compound having the structure VIII was obtained as a foam (yield; 1.7 gm).

Figure 13A:
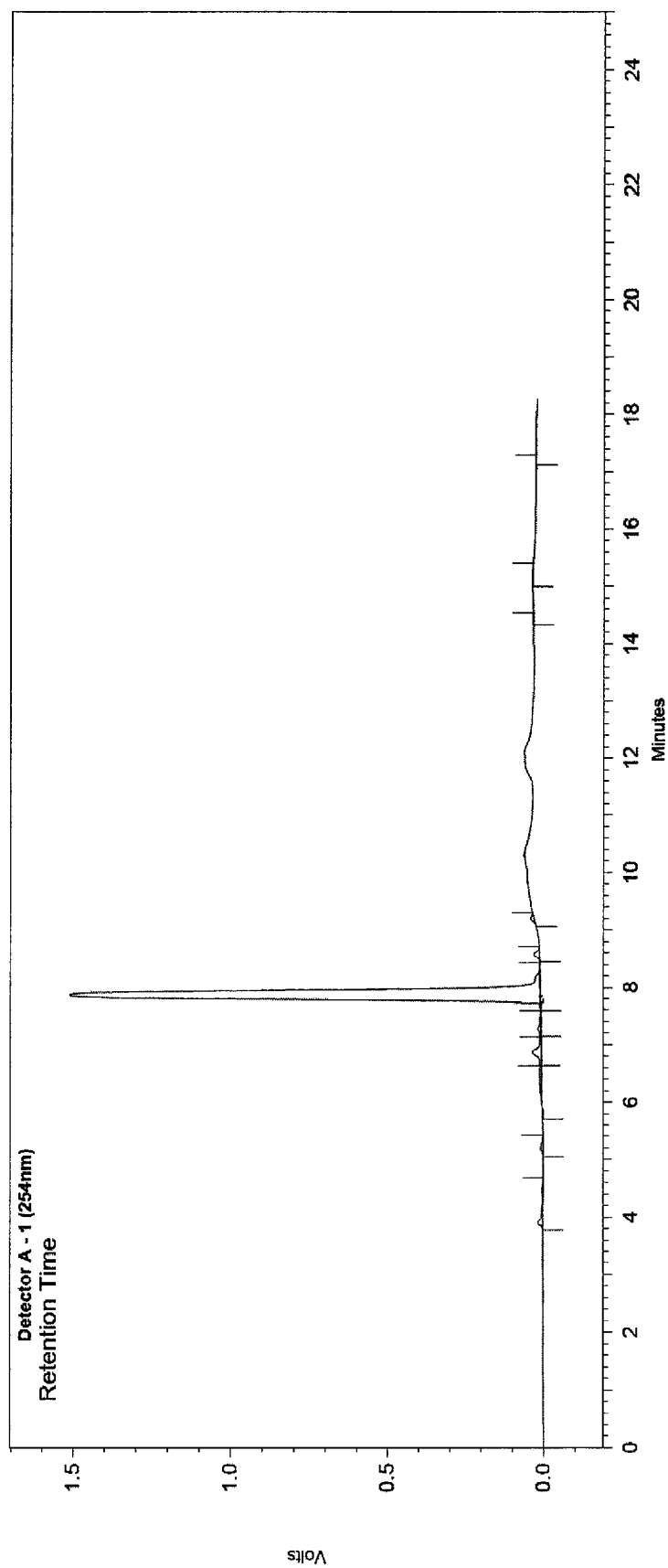
FIG. 13A is a HPLC chromatogram of 2',3',5'-tri-hydroxy-2',3',4',5',5"penta deuterium β-D ribofuranosyl-Uridine (structure IX)
Figure 14A:
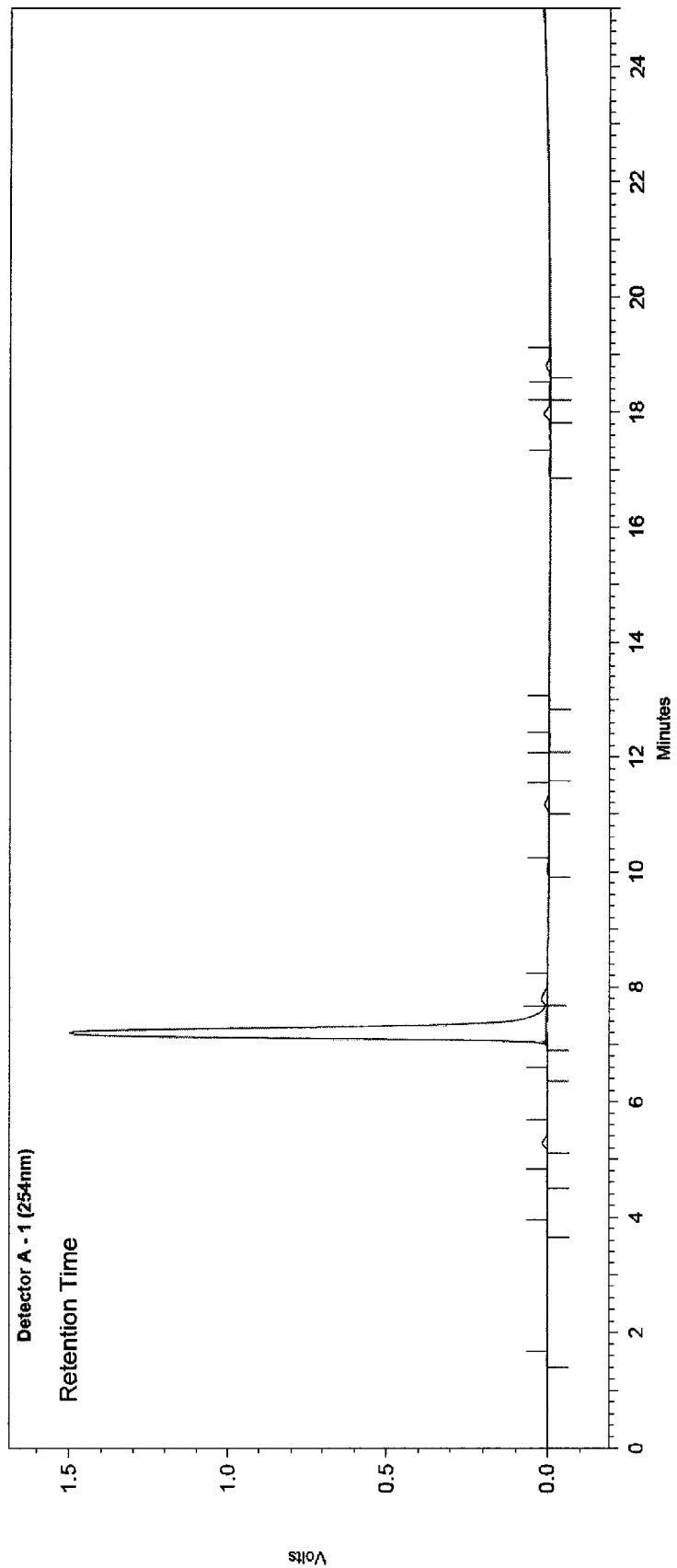
FIG. 14A is a HPLC report of 5'-O-dimethoxy trityl-2',3',4',5',5"penta deuterium β-D ribofuranosyl-Urdine (Structure X)
Figure 14C:
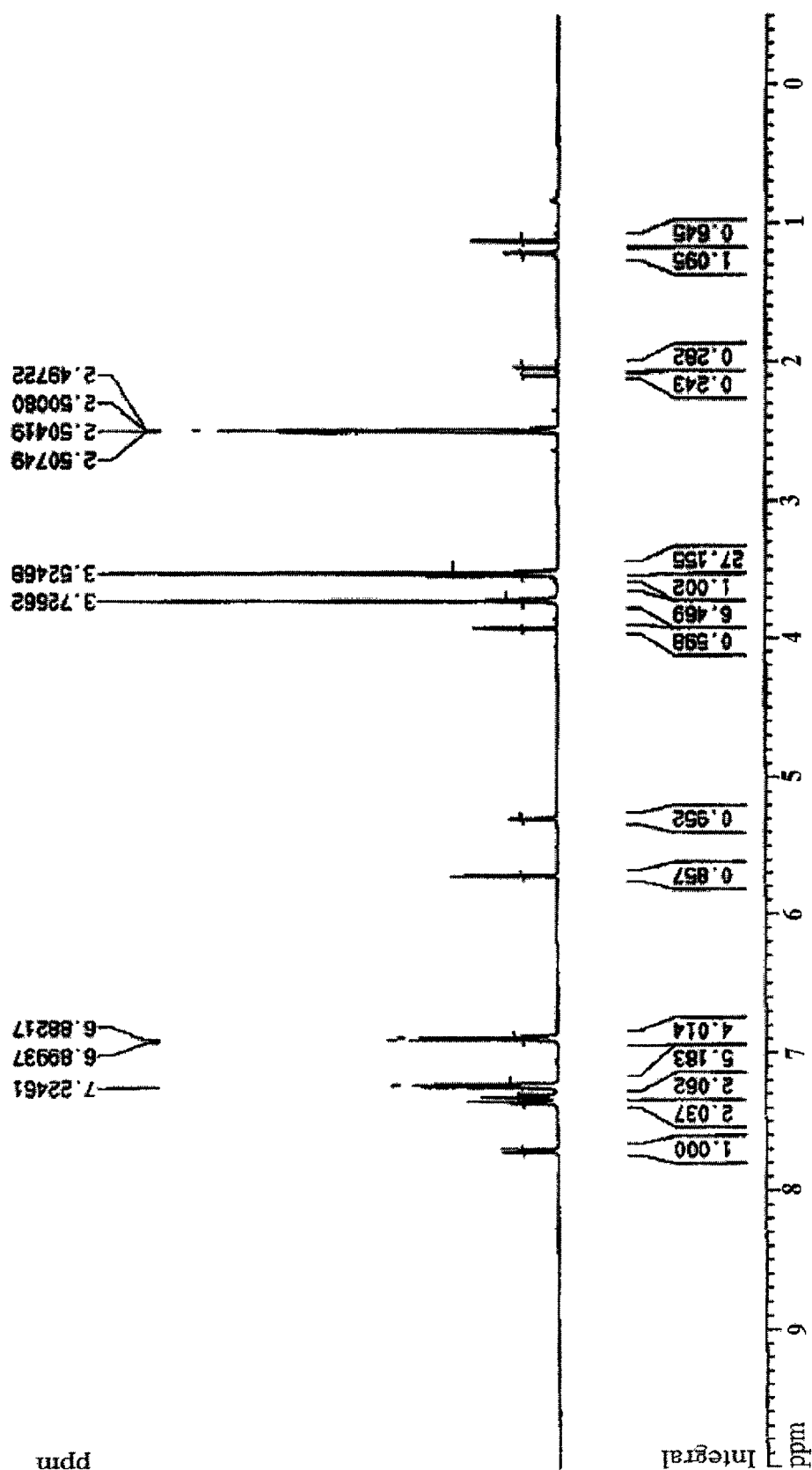
FIG. 14C is a ¹H-NMR spectrum of 5'-O-dimethoxy trityl-2',3',4',5',5"penta deuterium β-D ribofuranosyl-Uridine (Structure X)
Figure 14D:
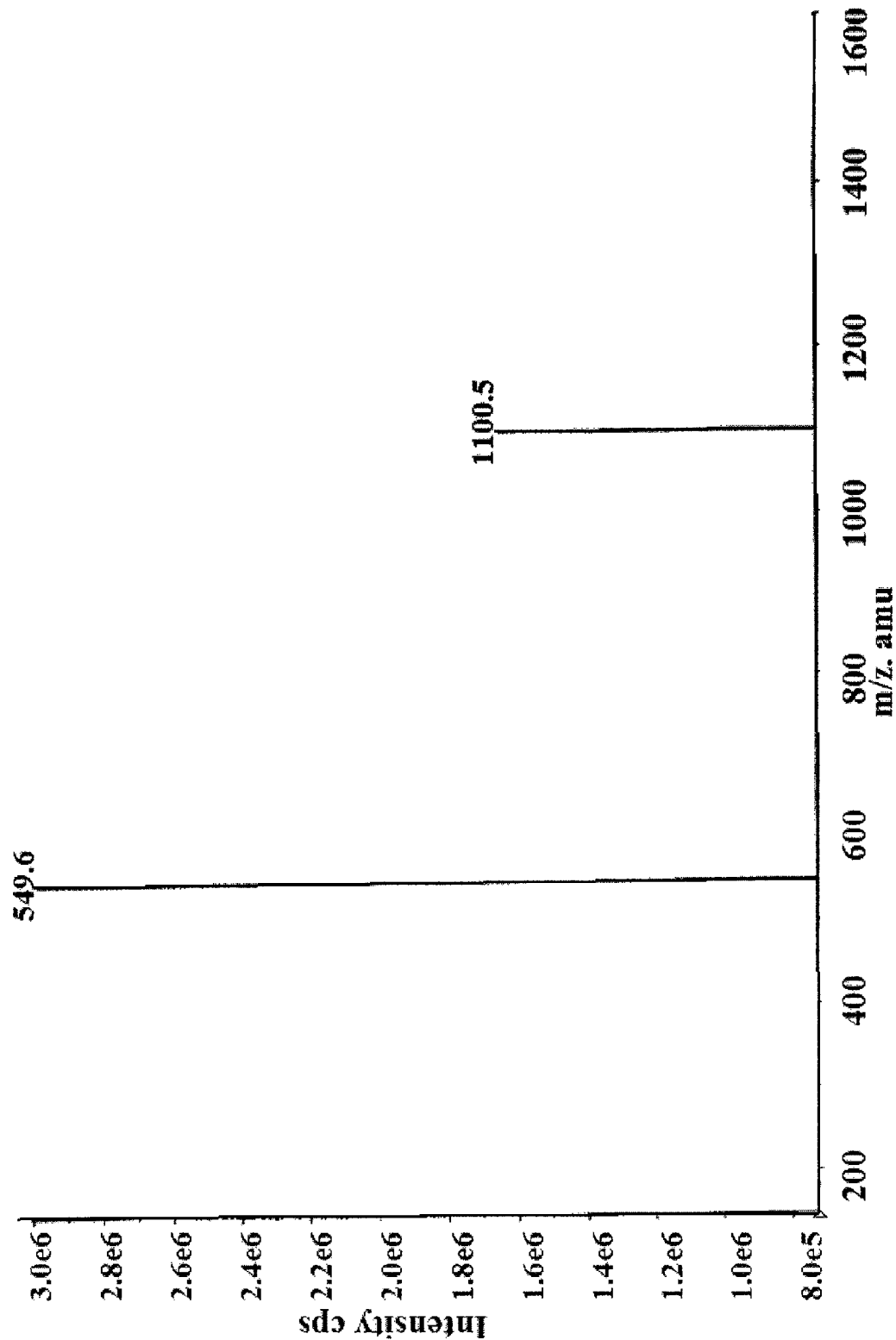
FIG. 14D is a ¹H-NMR spectrum of 5'-O-dimethoxytrityl-2'-O-tert-Butyldimethylsilyl-3'-O-succinyl pyridinium salt-2',3',4',5',5"penta deuterium β-D ribofuranosyl-N⁴ benzoyl Cytidine (compound structure XXIII)
Figure 15A:
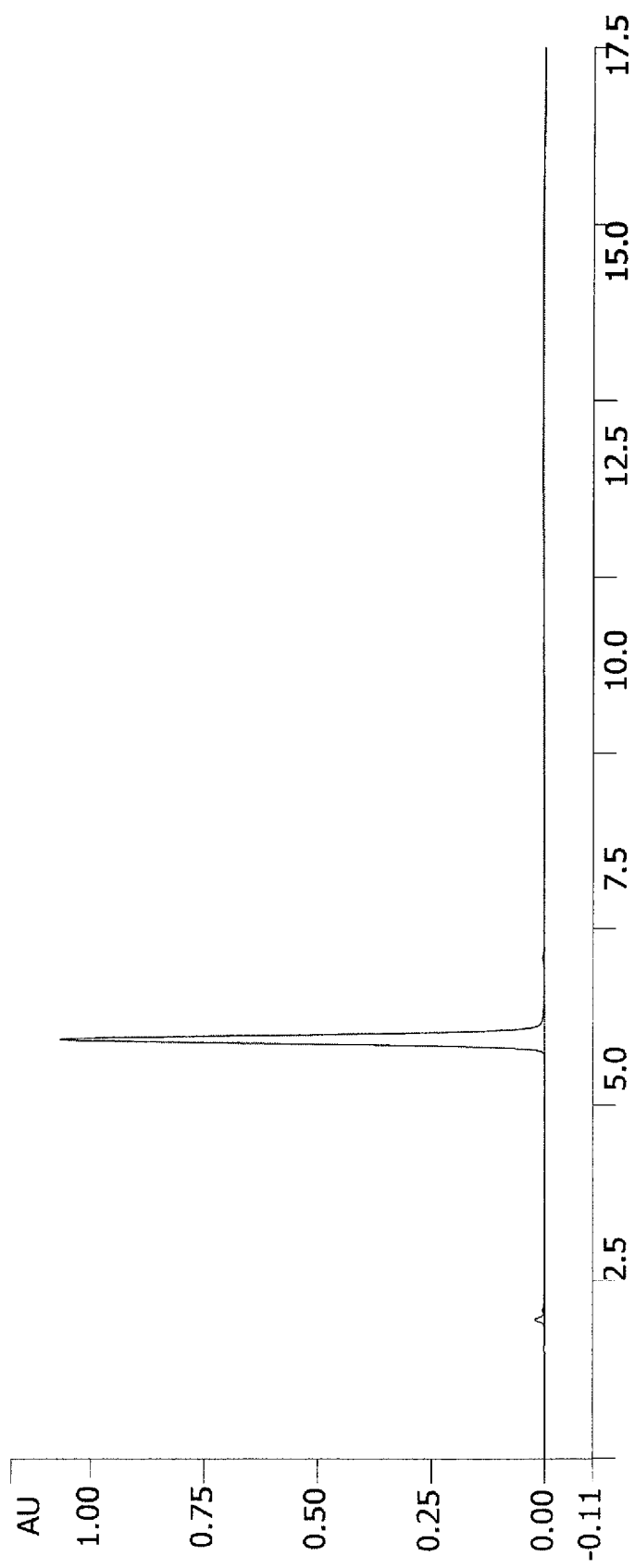
FIG. 15A is a HPLC chromatogram of 5'-O-dimethoxytrityl-2'-O-tert-Butyldimethylsilyl-2',3',4',5',5"penta deuterium β-D ribofuranosyl-Uridine (structure XI)
Figure 15C:
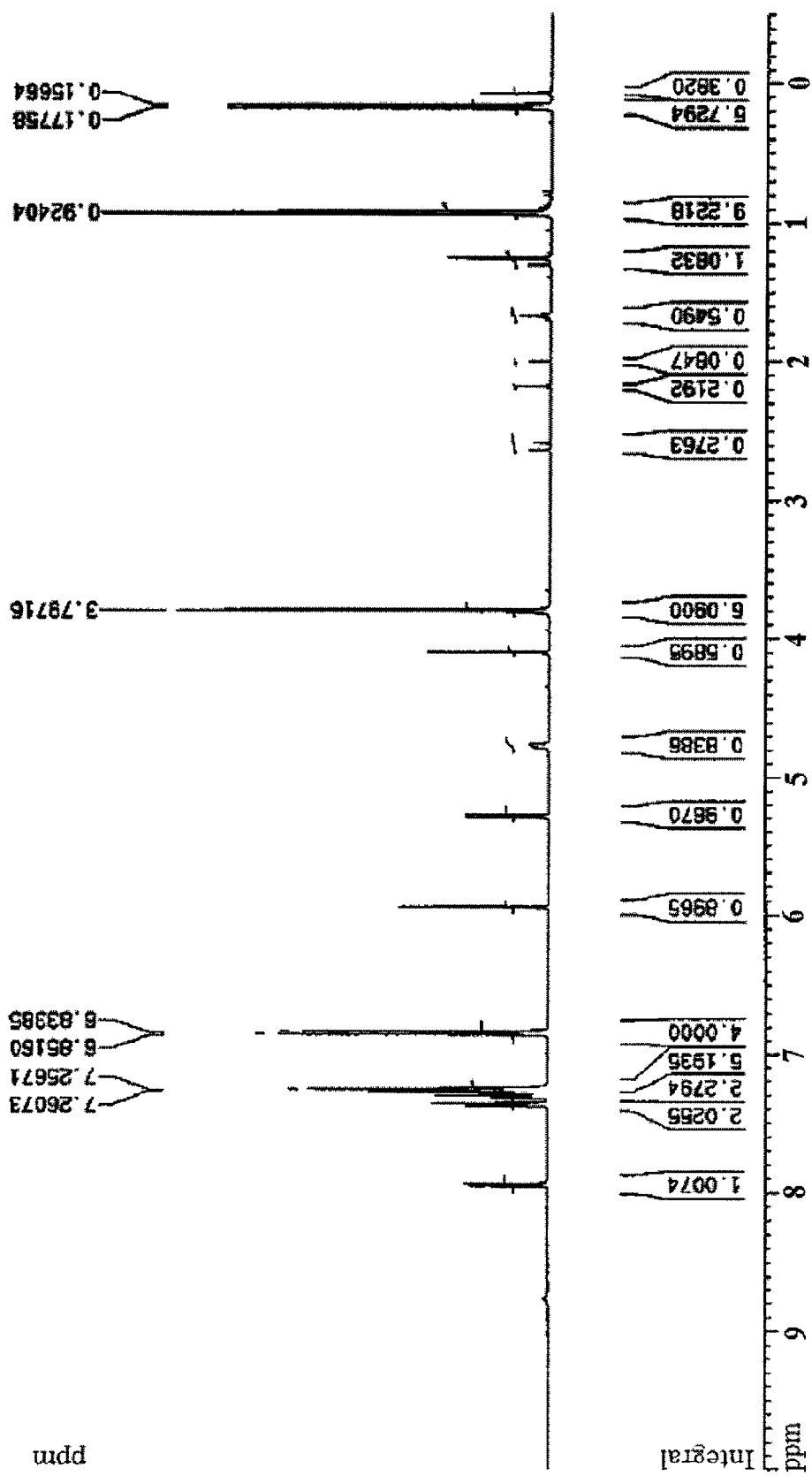
FIG. 15C is a ¹H-NMR spectrum of 5'-O-dimethoxytrityl-2'-O-tert-Butyldimethylsilyl-2',3',4',5',5"penta deuterium β-D ribofuranosyl-Uridine; (structure XI)
Figure 15D:
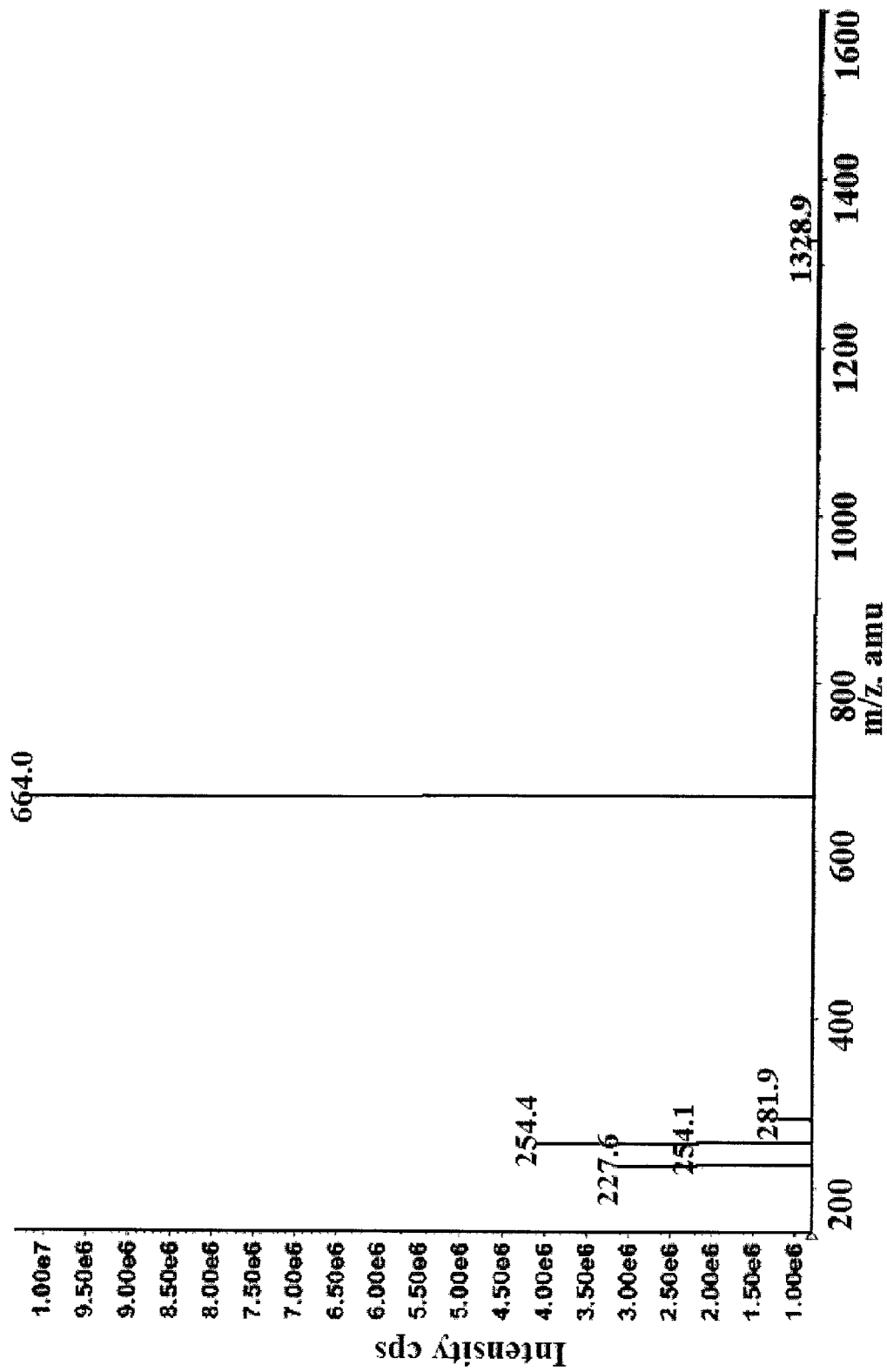
FIG. 15D is a mass spectrum of 5'-O-dimethoxytrityl-2'-O-tert-Butyldimethylsilyl-2',3',4',5',5"penta deuterium β-D ribofuranosyl-Uridine (structure XI); Calculated mass: 665.32; Observed Mass: 664.00.
Figure 16A:
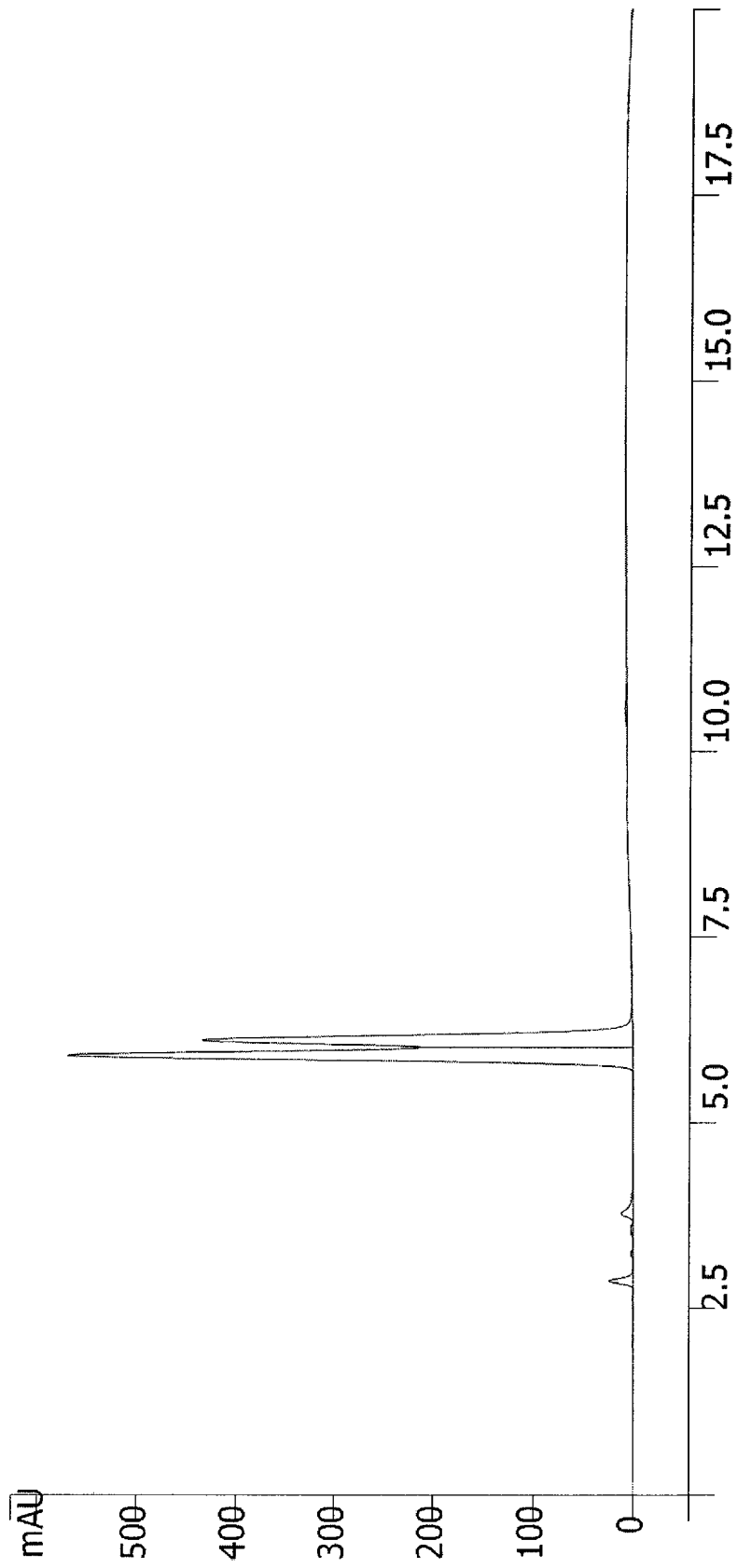
FIG. 16A is a HPLC chromatogram of 5'-O-dimethoxytrityl-2'-O-tert-Butyldimethylsilyl-3'-N,N-diisopropyl cyanoethyl phosphoramidite-2',3',4',5',5"penta deuterium β-D ribofuranosyl Uridine (structure XIII)
Figure 16C:
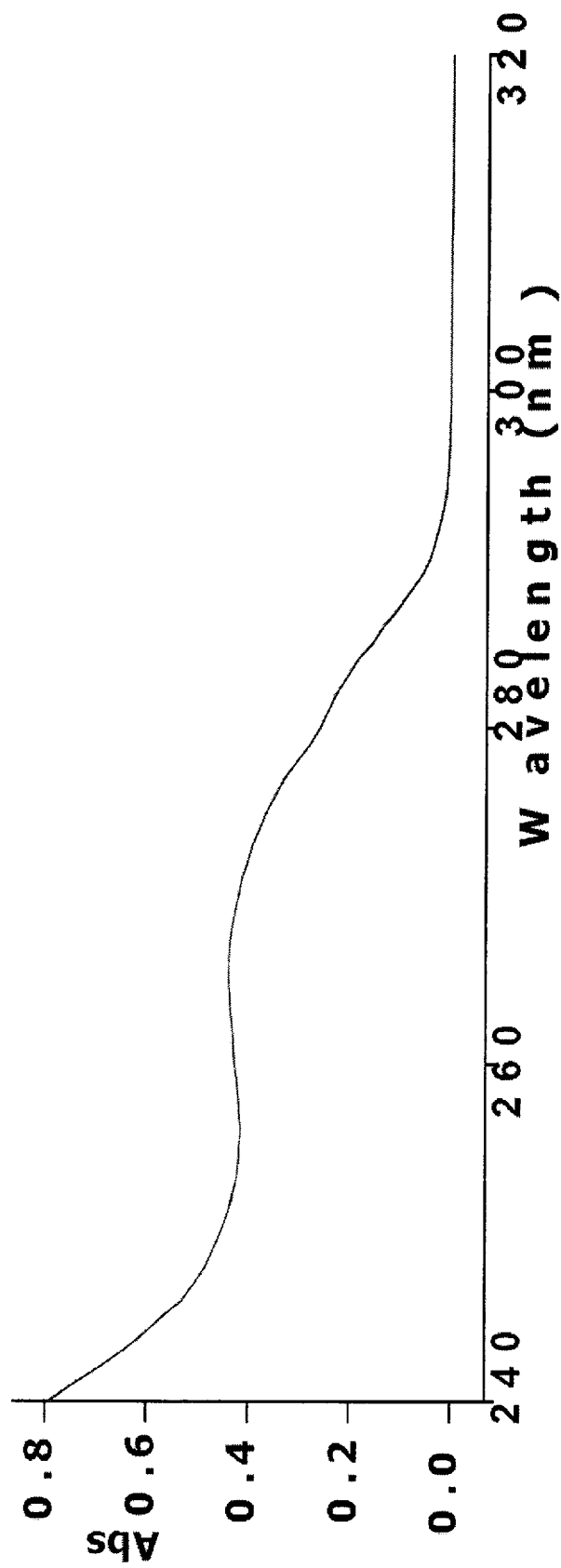
FIG. 16C is a UV analysis of 5'-O-dimethoxytrityl-2'-O-tert-Butyldimethylsilyl-3'-N,N-diisopropyl cyanoethyl phosphoramidite-2',3',4',5',5"penta deuterium β-D ribofuranosyl Uridine (structure XIII)
Figure 16E:
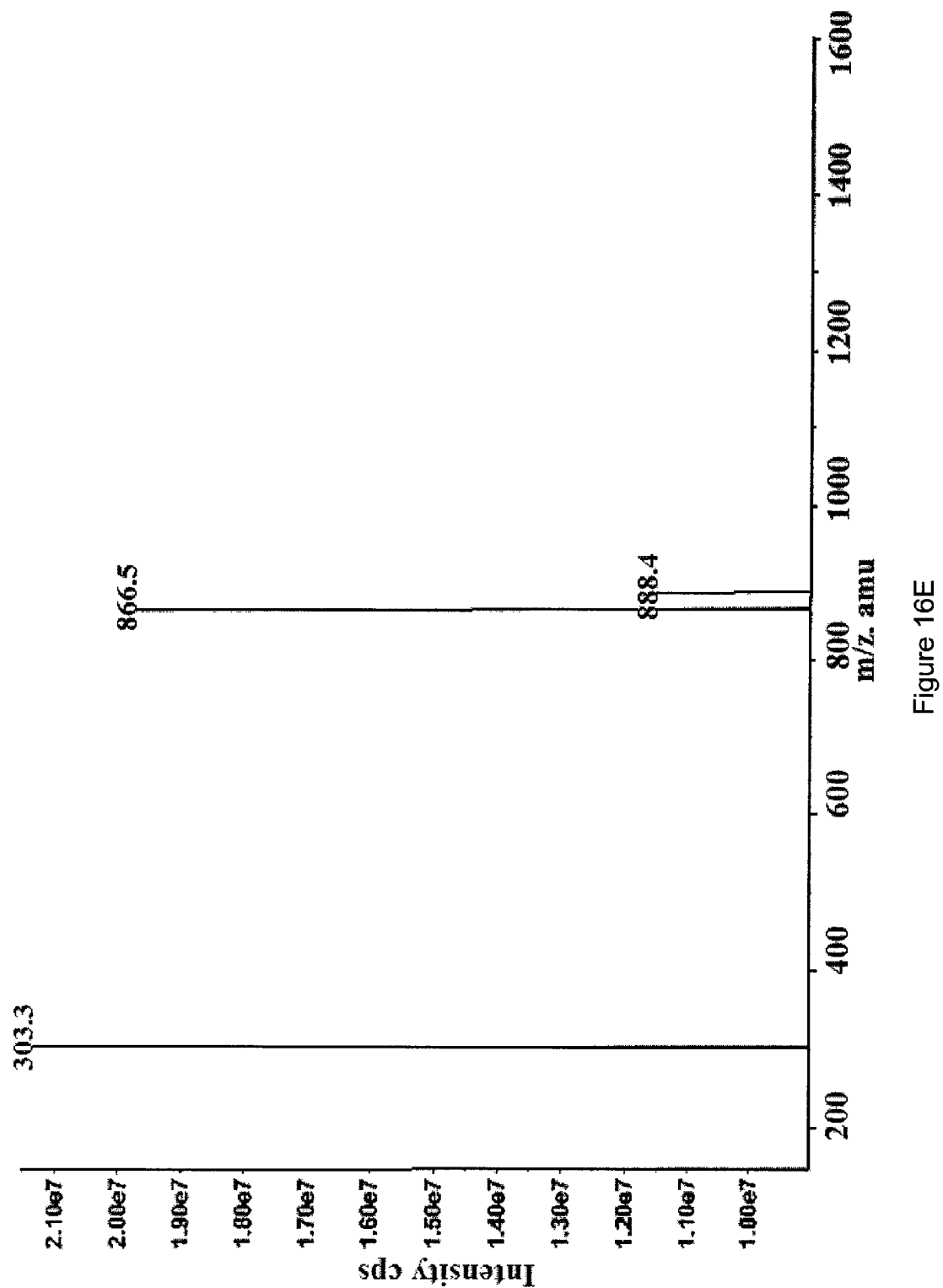
FIG. 16E is a mass spectrum of 5'-O-dimethoxytrityl-2'-O-tert-Butyldimethylsilyl-3'-N,N-diisopropyl cyanoethyl phosphoramidite-2',3',4',5',5"penta deuterium β-D ribofuranosyl Uridine (structure XIII); Calculated mass: 865.43; Observed Mass: 866.50; (Mass+Sodium Ion (888.4)
Figure 16F:
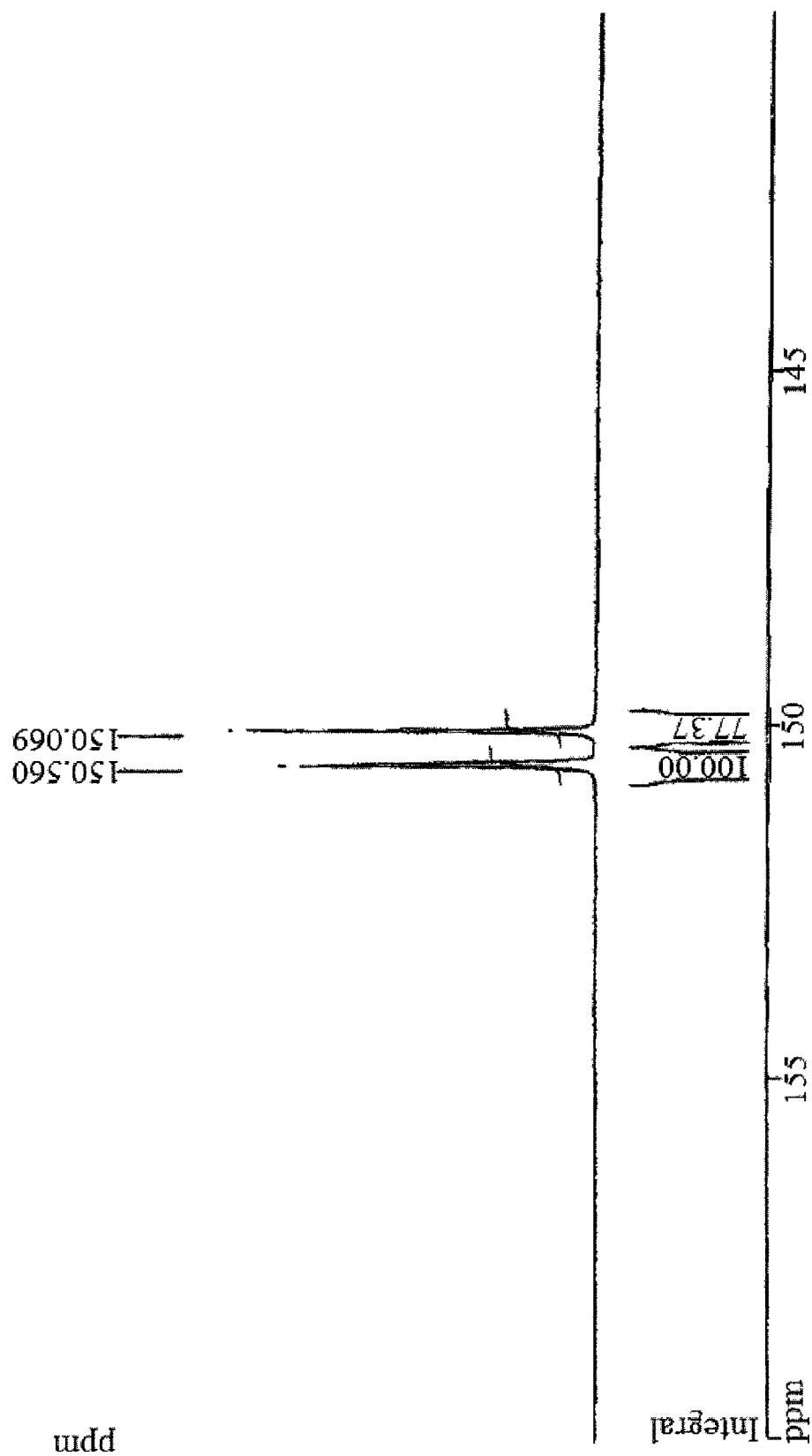
FIG. 16F is a $^{31}$P NMR spectrum of 5'-O-dimethoxytrityl-2'-O-tert-Butyldimethylsilyl-3'-N,N-diisopropyl cyanoethyl phosphoramidite-2',3',4',5',5"penta deuterium β-D ribofuranosyl Uridine (structure XIII); Lot#: SK188-38. sharp doublet at 150.560 & 150.069 ppm; purity: 100%; Δ=0.491.

A mixture of structure VIII (1.7 gm) in pyridine (20 ml) and aqueous ammonia solution (37% w/v, 20 ml) was kept in a tightly sealed flask at 37° C. for 48 hours. The mixture was then evaporated in vacuum and co-evaporated with isopropyl alcohol to dryness. A solution of residue in dichloromethane was applied to a column (2×15 cm) packed with Silica Gel (70:230) (100 gm) in chloroform, followed by chloroform:methanol:85:15 (V:V). The pure fraction as visualized by UV, and was evaporated to yield a compound powder of structure IX, 2',3',5'-tri-hydroxy-2',3',4',5',5''penta deuterium β-D ribofuranosyl Uridine, (yield; 700 mg; 93.3%), See FIGS. 13A-13C. Rf; 0.4 system; chloroform:methanol (85:15). UV; maxima at 260 (0.494), Emax; 7826.22.

Synthesis of 5'-O-dimethoxy trityl-2',3',4',5',5''penta deuterium β-D ribofuranosyl Uridine (Structure X) 2',3',5'-tri-hydroxy-2',3',4',5',5''penta deuterium β-D ribofuranosyl Uridine (structure IX; 0.7 gm; 0.175 mmol) was dried with dry pyridine two times followed by addition of dry pyridine (10 ml). The solution was stirred and cooled to 0° C. with a drying tube attached. To the solution was added 4,4,dimethoxy trityl chloride (DMT-Cl; 1.16 gm; 3.42 m.mole) in two portions at one hour intervals. The progress of the reaction was monitored by TLC in Chloroform (85:15). After completion of reaction (approx. 4 hours), the reaction mixture was quenched with cooled methanol (5 ml), followed by removal of solvent on a rotary evaporator. The residual gum was taken in chloroform and washed with saturated bicarbonate solution once, followed by washing with brine solution once. The crude product obtained after removal of the solvent was chromatograph on a column of silica Gel (70:230 mesh size) (150 gm) with chloroform:methanol (95:5) as an eluant. Fractions were monitored by TLC and visualized by UV. Rf 0.4 in chloroform:methanol (95:05). Pure fractions were combined and evaporated to give an almost colorless foam, yield; of 1.3 gm; 86.6%, UVmax at 250 nm; Emax of 11,671. The product was analyzed by one or more of the following HPLC, UV, 1H NMR, mass spectral data and/or $^{31}$P NMR, see FIGS. 14A-14D.

Synthesis of 5'-O-dimethoxytrityl-2'-O-tert-Butyldimethylsilyl-2',3',4',5',5"penta deuterium β-D ribofuranosyl-Uridine XI and 5'-O-dimethoxytrityl-3'-O-tert-Butyldimethylsilyl-2',3',4',5',5"penta deuterium β-D ribofuranosyl-Uridine XII: Compound 5'-O-dimethoxy trityl-2',3',4',5',5"penta deuterium β-D ribofuranosyl Uridine (structure IX; 1.3 gm; 2.36 mmole) was dried by co-evaporation with anhydrous acetonitrile and under vacuum for several hours. The dried product was added to anhydrous tetrahydrofuran (THF, 13 ml). To the solution was added silver nitrate (AgNo3 0.5 gm, 2.94 mmole) under anhydrous condition with a drying tube on top of the reaction flask. To the mixture was added dry pyridine (0.69 ml; 8.54 mmole). The reaction mixture was stirred for 10 minute at room temperature. Subsequently, tert butyl dimethyl silyl chloride (TBDMS-Chloride, 0.53 gm, 3.52 mmole) was added under anhydrous conditions. The reaction mixture was sealed and stirred at room temperature for at 2.5 hours. The progress of the reaction was monitored by TLC and visualized under UV. The TLC solvent system was chloroform:Hexane:Acetone (65:25:10). The crude product showed formation of both the 2' isomer (Structure XI) and 3' isomer. The comparative analysis on TLC with unmodified 2' and 3'-isomers was carried out and the spots co-migrated.

After the usual work up, the crude product was chromatographed on a column of silica gel (230:400 mesh) with a solvent system consisting of chloroform:Hexane:Acetone: 65:25:10. The fractions were monitored by TLC and visualized by UV. The R$_f$ value was 0.38 in the same solvent system. Combined pure fractions were evaporated to give a foam having a yield of 800 mg, of 5'-O-dimethoxytrityl-2'-O-tert-Butyldimethylsilyl-2',3',4',5',5"penta deuterium β-D ribofuranosyl-Uridine 50.9% UV ˆmax at 250 nm (0.350); Emax of 1634. The 3'-isomer 1-(5-O-dimethoxytrityl-3-O-tert-Butyldimethylsilyl-2,3,4,5,5'penta deuterium β-D ribofuranosyl) Uracil XII was not isolated. The product was analyzed by one or more of the following HPLC, UV, 1H NMR, mass spectral data and/or $^{31}$P NMR, see FIGS. 15A-15D.

Synthesis of 5'-O-dimethoxytrityl-2'-O-tert-Butyldimethylsilyl-3'-N,N-diisopropyl cyanoethyl phosphoramidite-2',3', 4',5',5"penta deuterium β-D ribofuranosyl Uridine (Compound Structure XIII): From the synthesis of 5'-O-dimethoxytrityl-2'-O-tert-Butyldimethylsilyl-2',3',4',5', 5"penta deuterium β-D ribofuranosyl Uridine, Structure XI and 5'-O-dimethoxytrityl-3'-O-tert-Butyldimethylsilyl-2',3', 4',5',5"penta deuterium β-D ribofuranosyl Uridine Structure XII, the 2'-TBDMSilyl isomer (structure XI; 430 mg) was thoroughly dried with anhydrous acetonitrile and placed in a round bottom flask. Anhydrous tetrahydrofuran (4.3 ml) was added and the solution purged with Argon and replaced with a stopper. To the solution, under stirring, was added 2,4,6-collidine (430 microliter; 5 equivalents), followed by addition of 1-methyl imidazole (51 microliters; 1.0 equivalents). The solution was stirred at room temperature and N,N-diisopropylamino cyanoethyl phosphonamidic chloride (phosphorylating reagent, ChemGenes Catalog No. RN-1505; 290 microliters; 2 equivalents) was quickly added. After 70 minutes, the reaction was complete, and it was worked up by dilution with chloroform. The organic layer was placed in a separatory funnel and washed with saturated aqueous sodium bicarbonate, followed by further washing of the organic layer with brine solution. The organic layer was passed over anhydrous sodium sulfate. The solution was concentrated on a rotary evaporator. The TLC was checked in the system ethyl acetate:hexane:triethylamine (30:60:10). The crude product was purified on a column of silica gel (230-400 mesh) column diameter (30 cm×1.5 cm). The pure fractions were monitored by TLC and combined and then concentrated. A colorless, foamy product was obtained having a dry weight of 300 mg. The product was analyzed by HPLC, UV, 1H NMR, mass spectral data and 31P NMR, see FIGS. 16A-16F.

Solid supports attached with deuterium labeled nucleosides are required for the synthesis of oligonucleotides. Solid support bound with deuterium labeled nucleosides after oligonucleotide synthesis result in deuterium labeled nucleoside at the 3'-end of the oligonucleotide. In this process the oligonucleotide synthesis is carried out from 3'-end to 5'-end direction (conventional oligonucleotide synthesis). The instant invention discloses methods for synthesizing deuterium labeled nucleoside -3'-succinate nucleosides with controlled deuterium label which can vary from 0.1%-98% deuterium at specific positions of the sugar and purine/pyrimidine bases. The instant invention discloses a process which incorporates deuterium containing phosphoramidites and solid supports, which have varying percent of enrichment of deuterium with a ratio of deuterium and hydrogen ranging from 20:98.

Structure B illustrates a deuterated solid support structure having the chemical structure of:

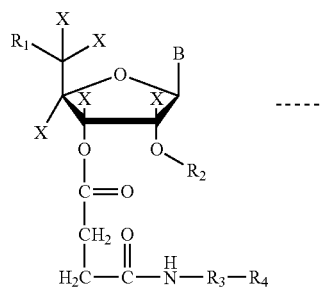

wherein X represents deuterium or hydrogen, R1 represents a blocking group, R2 independently represents a blocking group, R3 represents a linking molecule, and R4 represents a solid support and B represents a nucleobase. As described previously, B may be a natural base, a modified base, or combinations thereof. Linking molecules are generally known in the art as small molecules which function to connect a solid support to functional groups. The preferred linking molecule is succyl-Icaa, but other linking molecules known to one of skill in the art may be used. The solid support is generally used to attach to a first nucleoside. In a preferred embodiment, the solid support is controlled pore glass (CPG). However, other supports, such as, but not limited to, oxalylcontrolled pore glass, macroporous polystyrene (MPPS), aminopolyethyleneglycol, may be used as well.

FIG. 4 illustrates Scheme 3, synthesis of a deuterated ribonucleoside coupled to a solid support structure, illustrated herein as 5'-O-dimethoxytrityl-2'-O-tert-Butyldimethylsilyl-3'-succinyl Icaa-CPG-2',3',4',5',5"penta deuterium β-D ribofuranosyl Uridine.

Figure 17A:
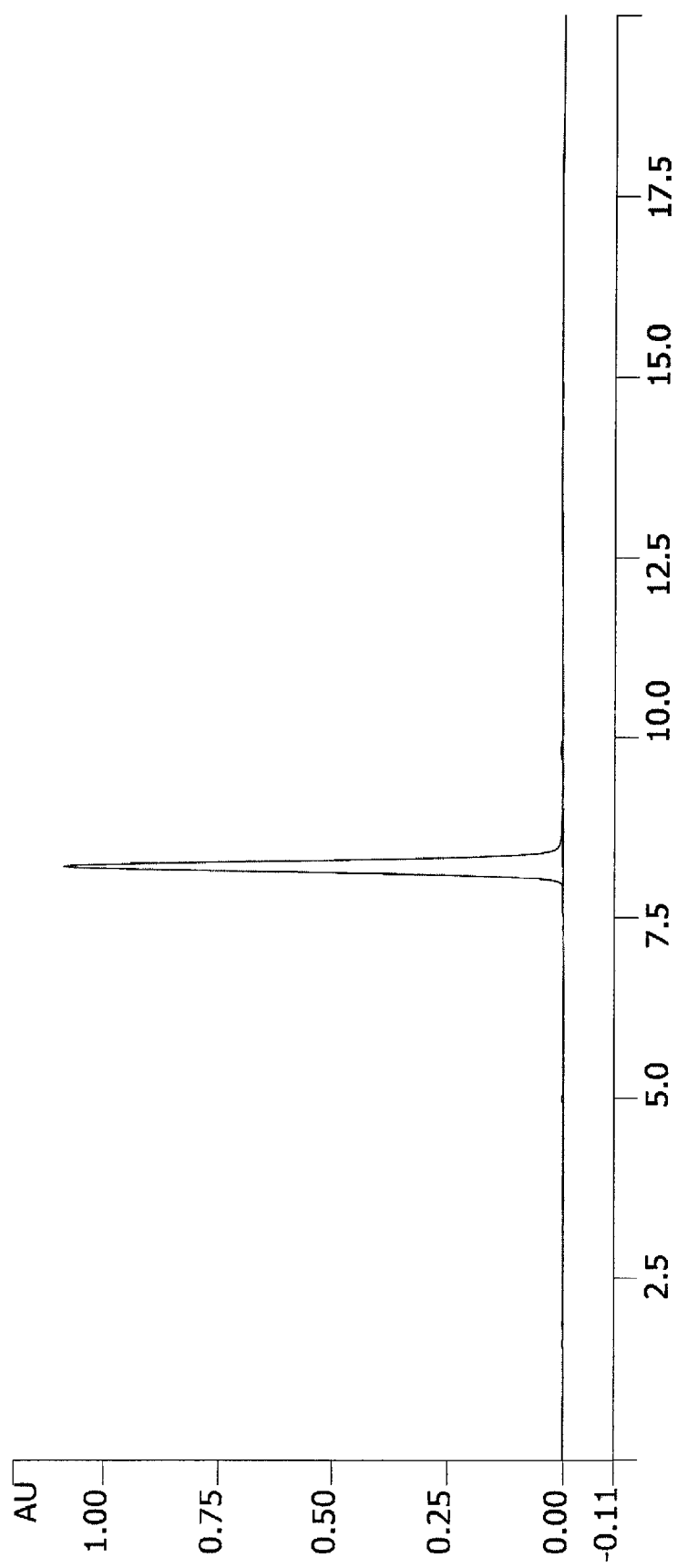
FIG. 17A is a HPLC chromatogram of 5'-O-dimetoxytrityl-2'-O-terbutyldimethyl Silyl-2',3',4',5',5"penta deuterium β-D ribofuranosyl-N$^4$ Benzoyl Cytidine structure XIV)
Figure 17C:
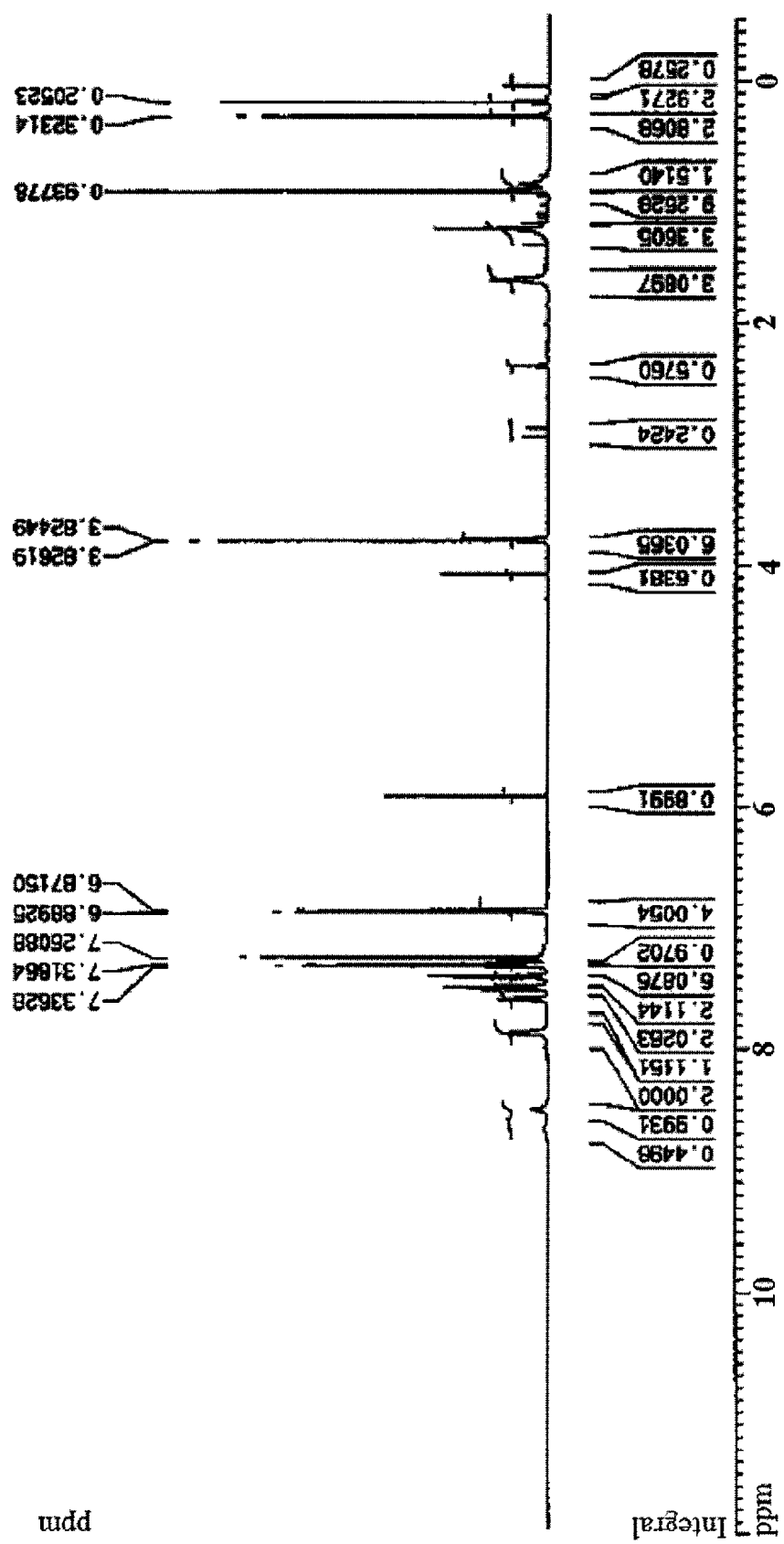
FIG. 17C is a 1H-NMR spectrum of 5'-O-dimetoxytrityl-2'-O-terbutyldimethyl Silyl-2',3',4',5',5"penta deuterium β-D ribofuranosyl-N$^4$ Benzoyl Cytidine (structure XIV)
Figure 17D:
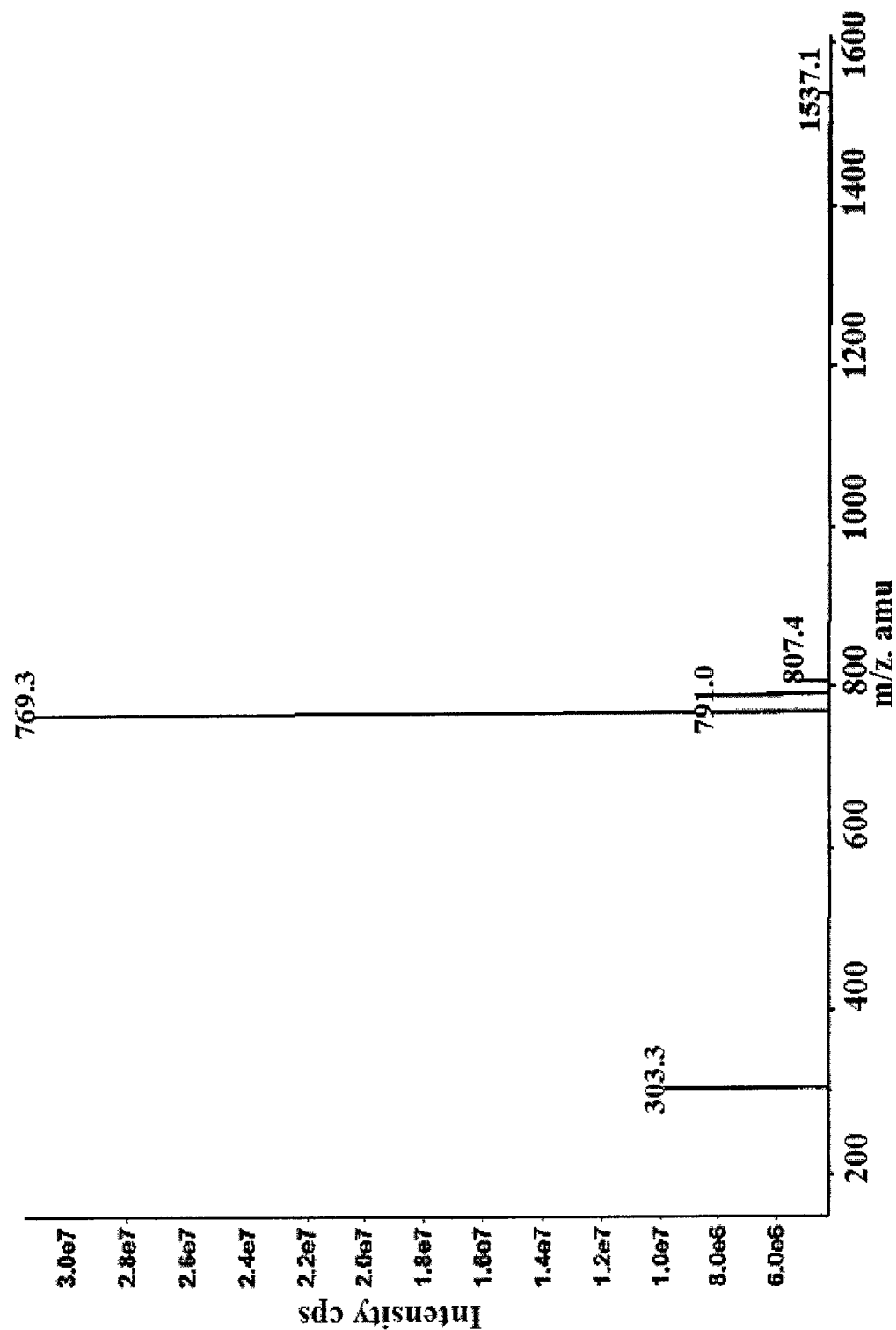
FIG. 17D is a mass spectrum of 5'-O-dimetoxytrityl-2'-O-terbutyldimethyl Silyl-2',3',4',5',5"penta deuterium β-D ribofuranosyl-N$^4$ Benzoyl Cytidine (structure XIV); Calculated mass: 768.36; Observed Mass: 769.30.
Figure 17E:
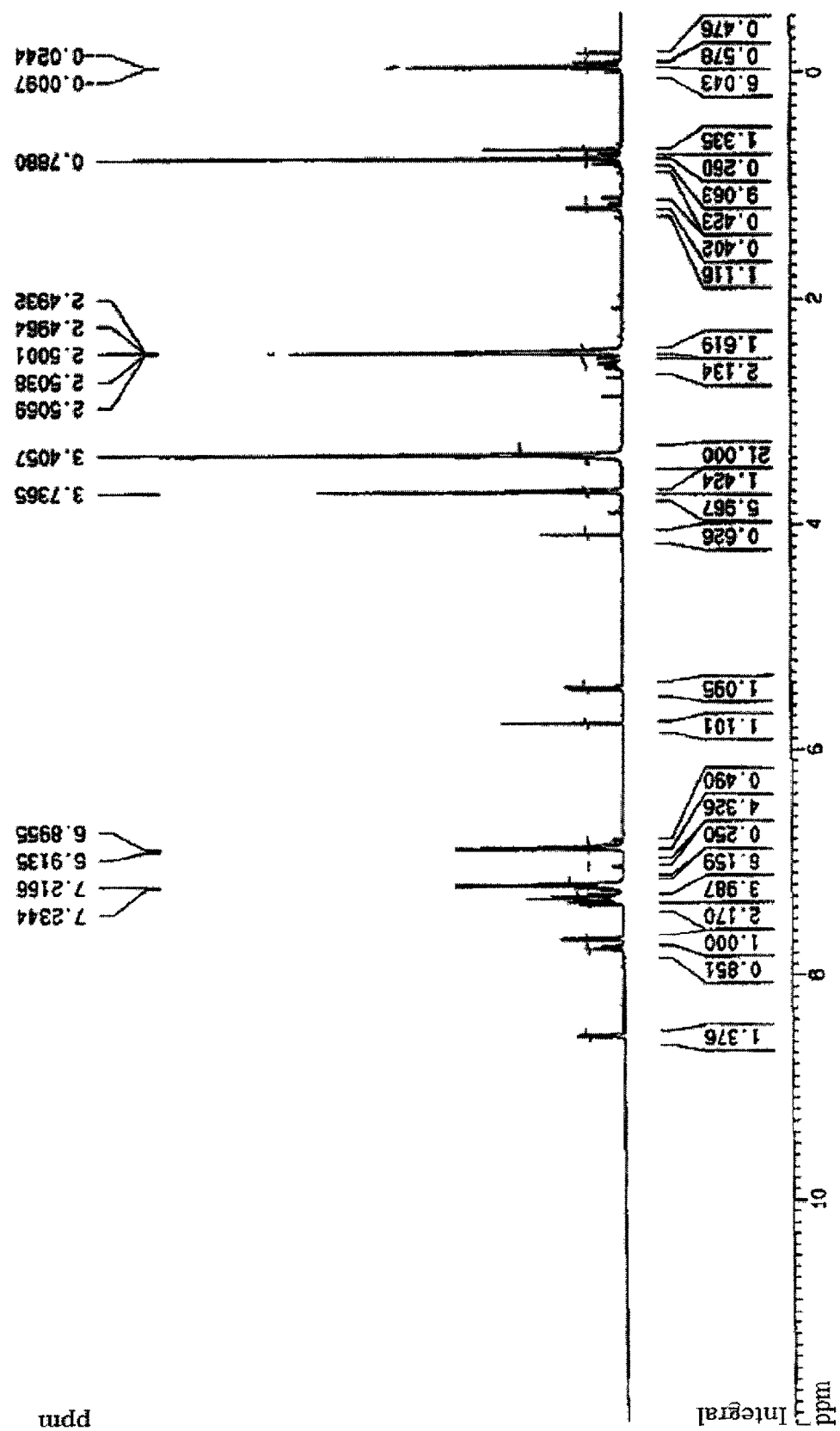
FIG. 17E is a $^1$H-NMR spectrum of 5'-O-dimethoxytrityl-2'-O-tert-Butyldimethylsilyl-3'-O-succinyl pyridinium salt-2',3',4',5',5"penta deuterium β-D ribofuranosyl-Uridine (structure XIV)
Figure 17F:
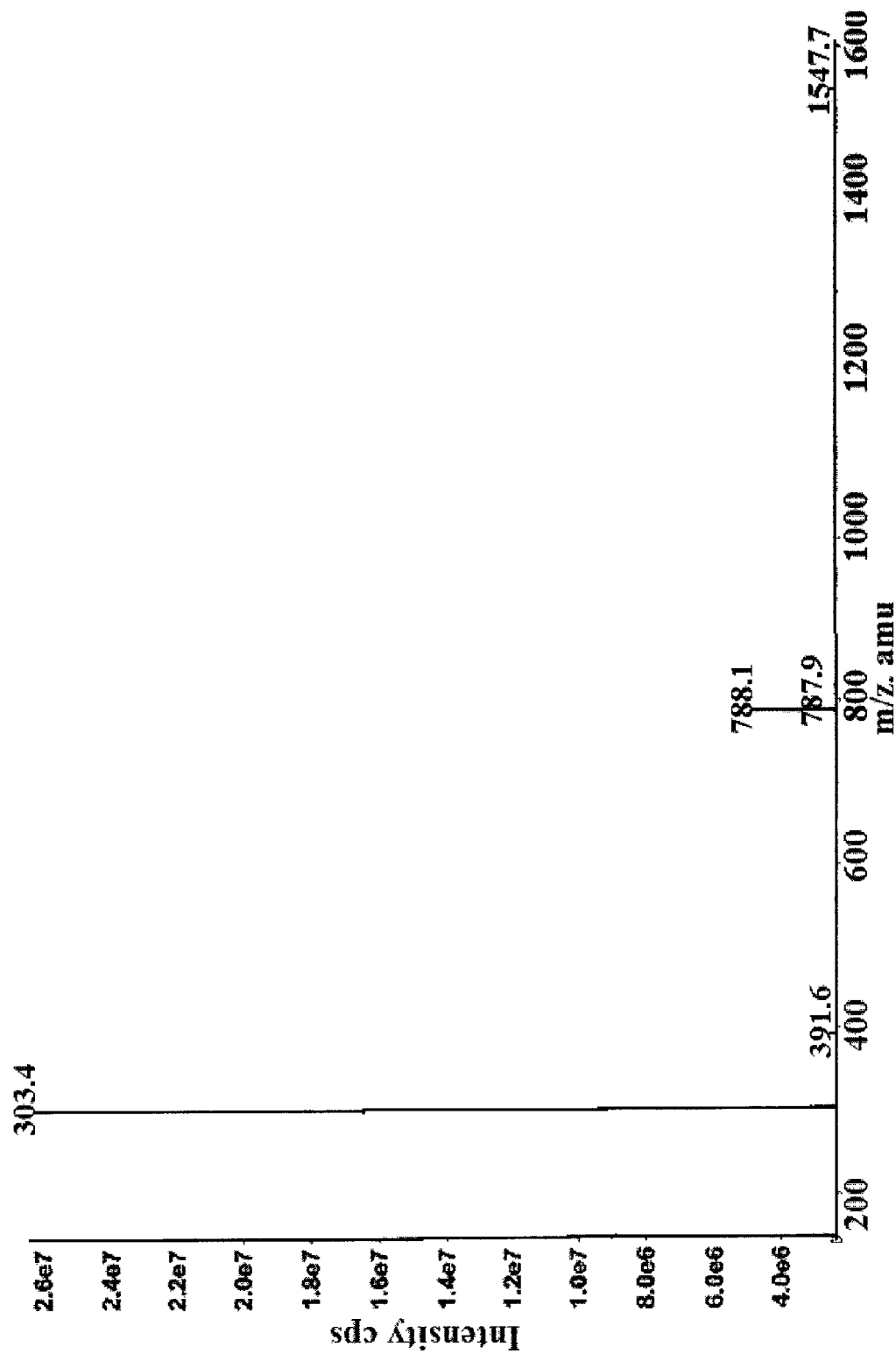
FIG. 17F is a positive mode-mass spectrum of 5'-O-dimethoxytrityl-2'-O-tert-Butyldimethylsilyl-3'-O-succinyl pyridinium salt-2',3',4',5',5"penta deuterium β-D ribofuranosyl-Uridine (structure XIV); Calculated mass: 764.83; Observed Mass: 788.10 (+Sodium Ion)
Figure 18A:
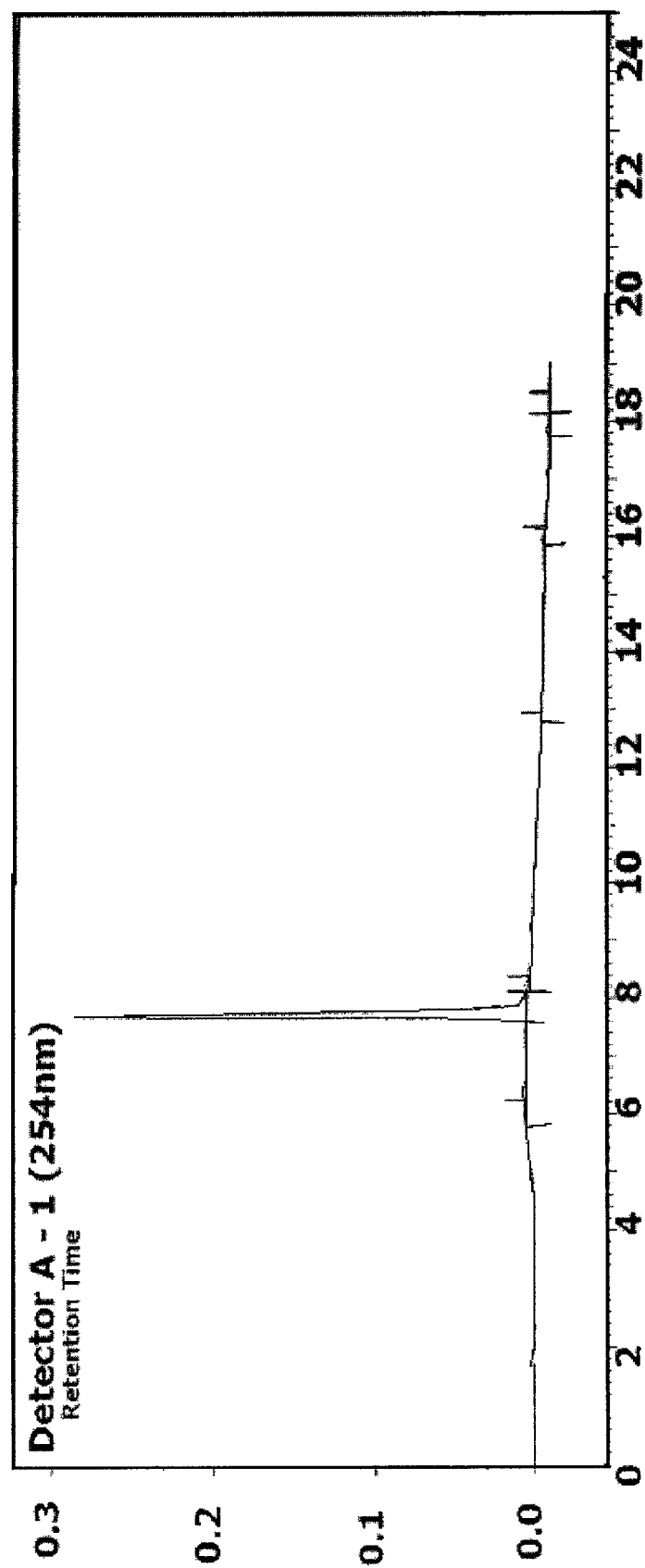
FIG. 18A is a HPLC report of 2',3',5'-tri Hydroxy-2',3',5',5"penta deuterium β-D ribofuranosyl-N$^4$ benzoyl Cytidine (structure XVIII)
Figure 18C:
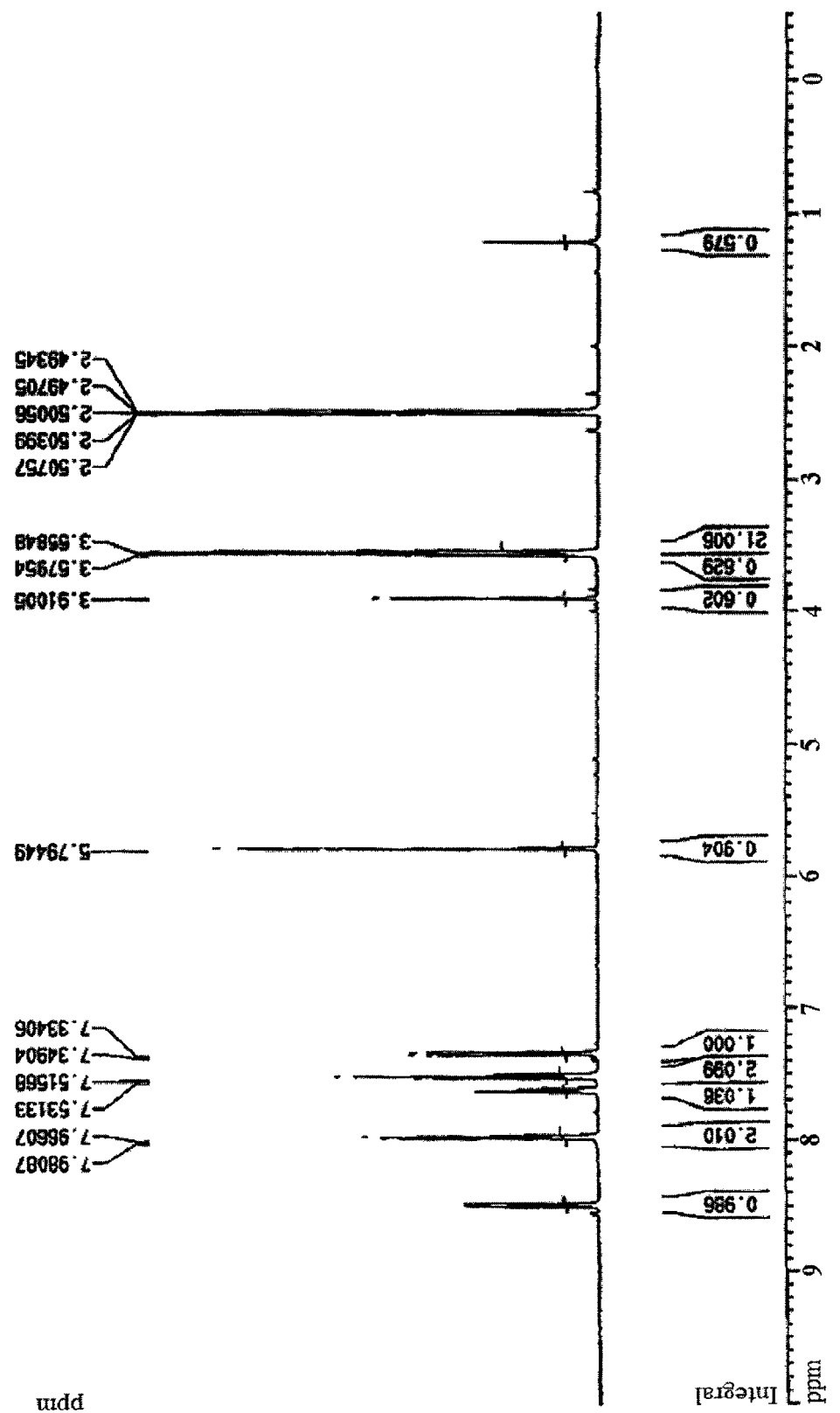
FIG. 18C is a mass spectrum of 2',3',5'-tri Hydroxy-2',3',5',5"penta deuterium β-D ribofuranosyl-N$^4$ benzoyl Cytidine (structure XVIII); Calculated mass: 352.14; Observed Mass: 352.50.
Figure 18D:
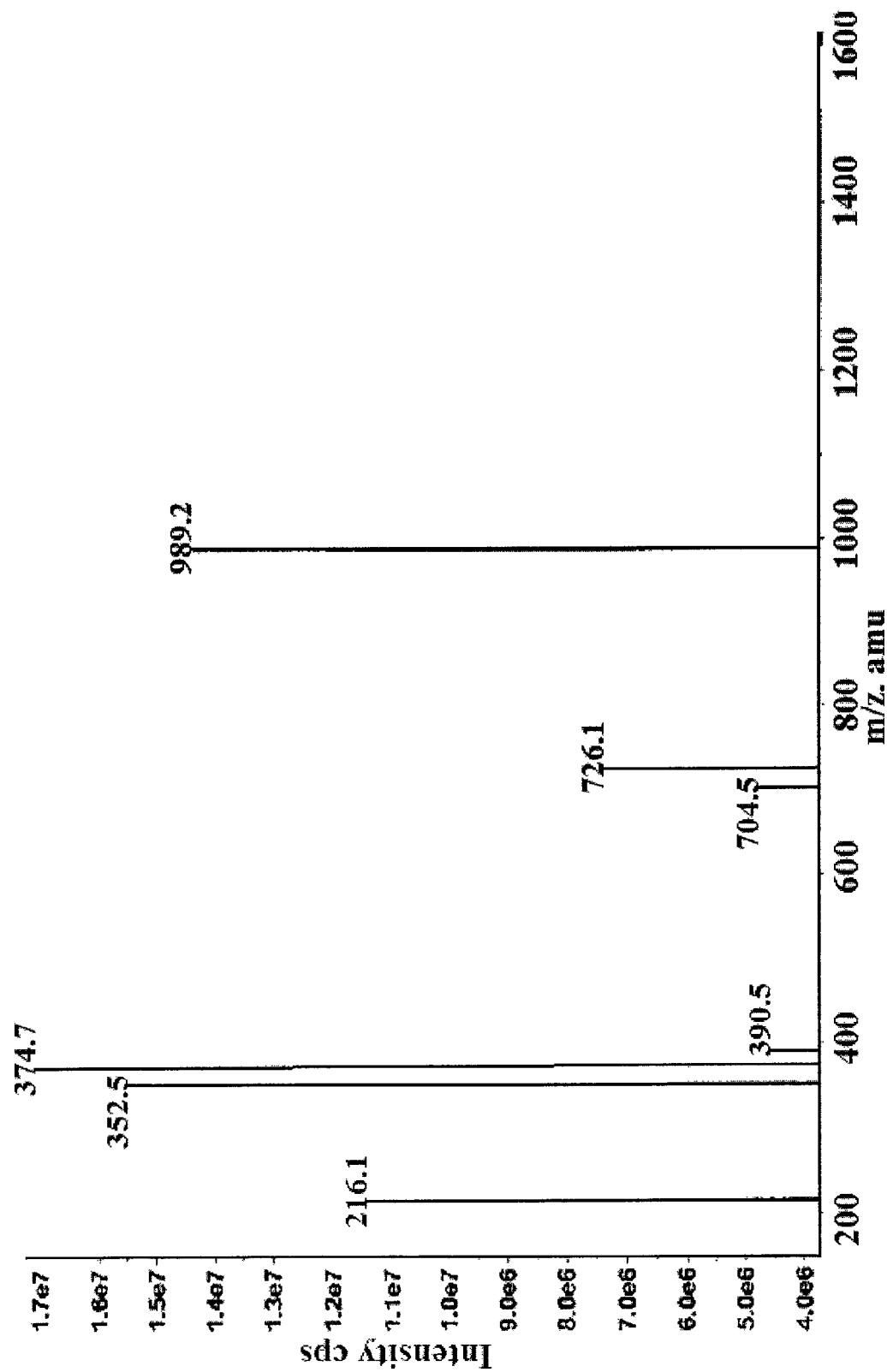
FIG. 18D is a mass spectrum of 2',3',5'-tri Hydroxy-2',3',5',5"penta deuterium β-D ribofuranosyl-N$^4$ benzoyl Cytidine (structure XVIII); Calculated mass: 352.14; Observed Mass: 352.50.
Figure 19A:
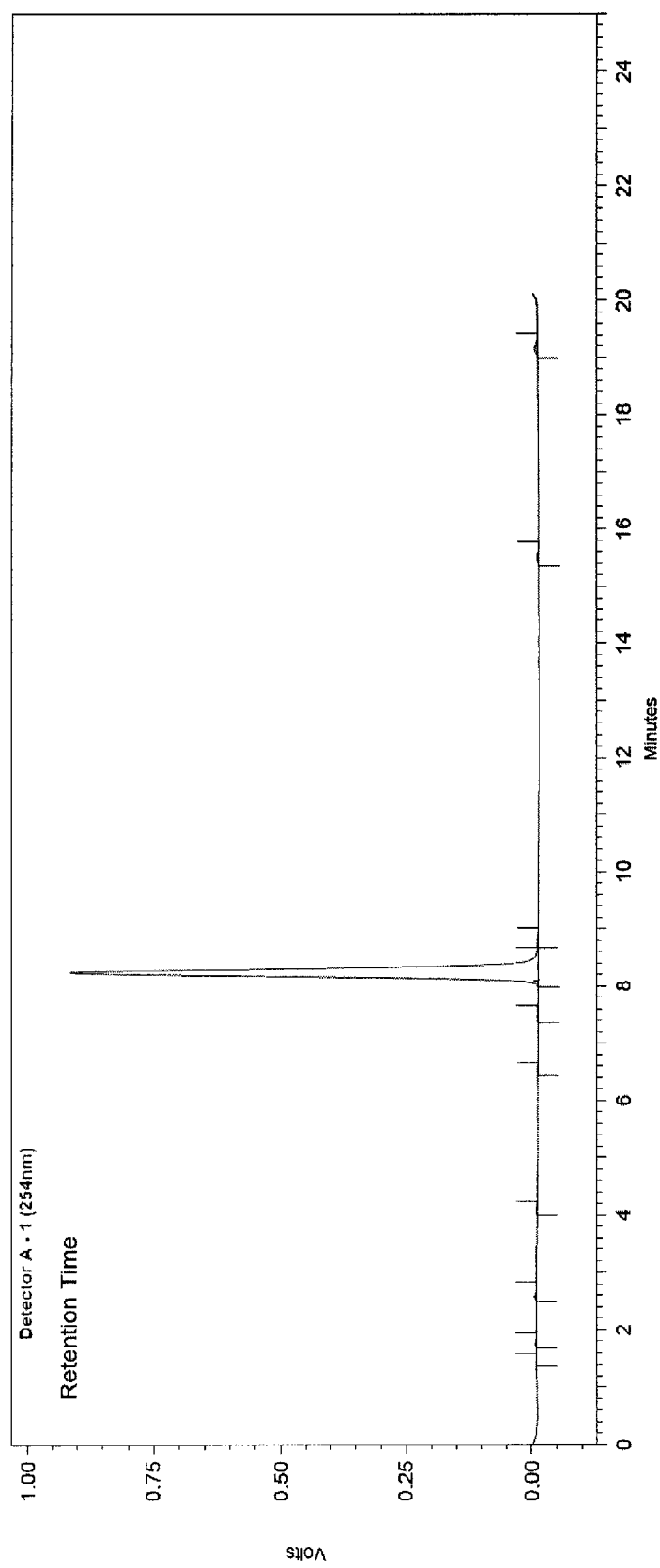
FIG. 19A is a positive mode-mass spectrum of 5'-O-dimethoxytrityl-2'-O-tert-Butyldimethylsilyl-3'-O-succinyl pyridinium salt-2',3',4',5',5"penta deuterium β-D ribofuranosyl-Uridine (structure XIV); Calculated mass: 764.83; Observed Mass: 788.10 (+Sodium Ion)
Figure 19C:
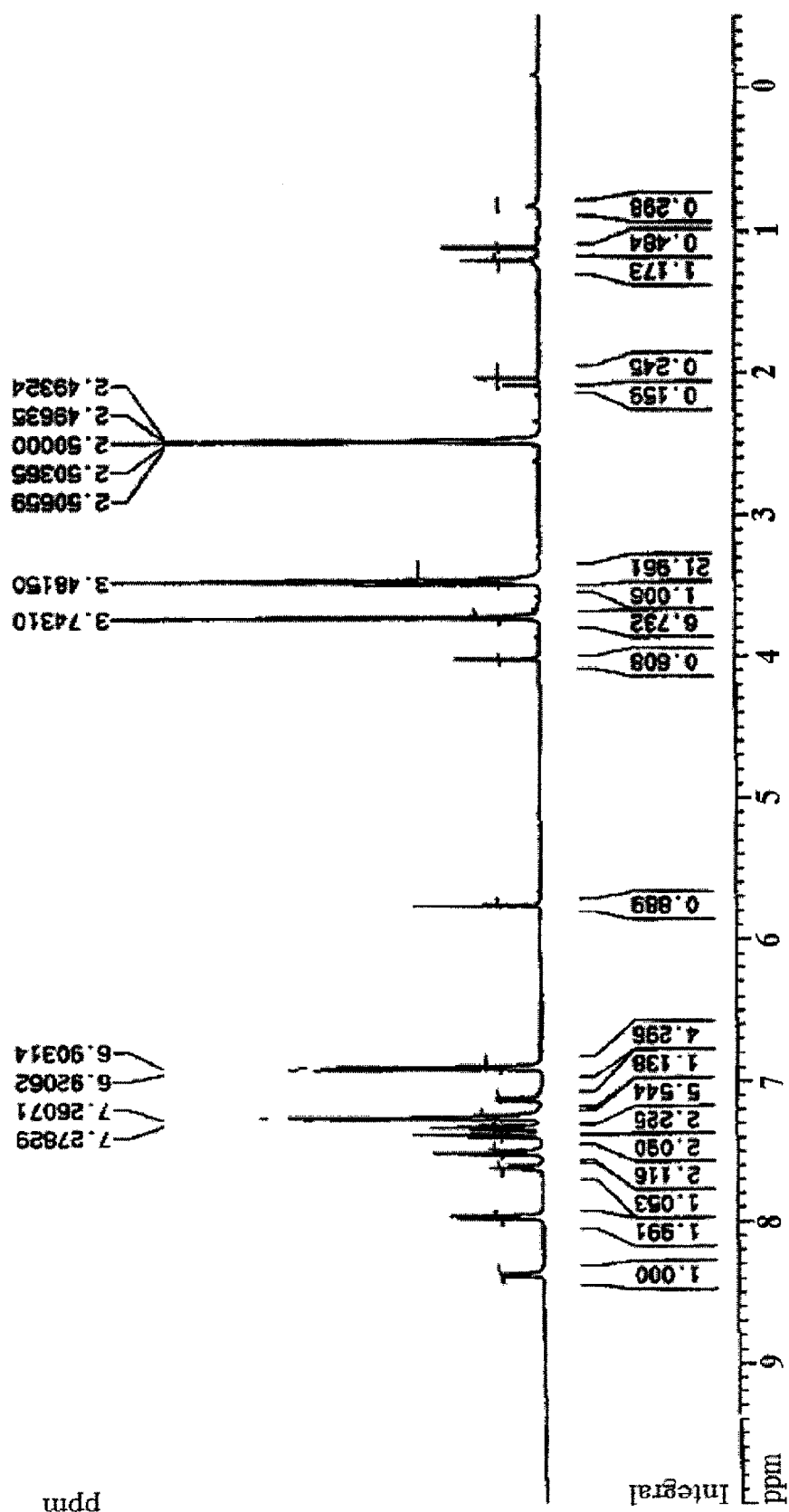
FIG. 19C is a $^1$H-NMR spectrum of 5'-O-dimethoxytrityl-2',3',4',5',5"penta deuterium β-D ribofuranosyl-N$^4$ Benzoyl Cytidine (compound XIX)
Figure 19D:
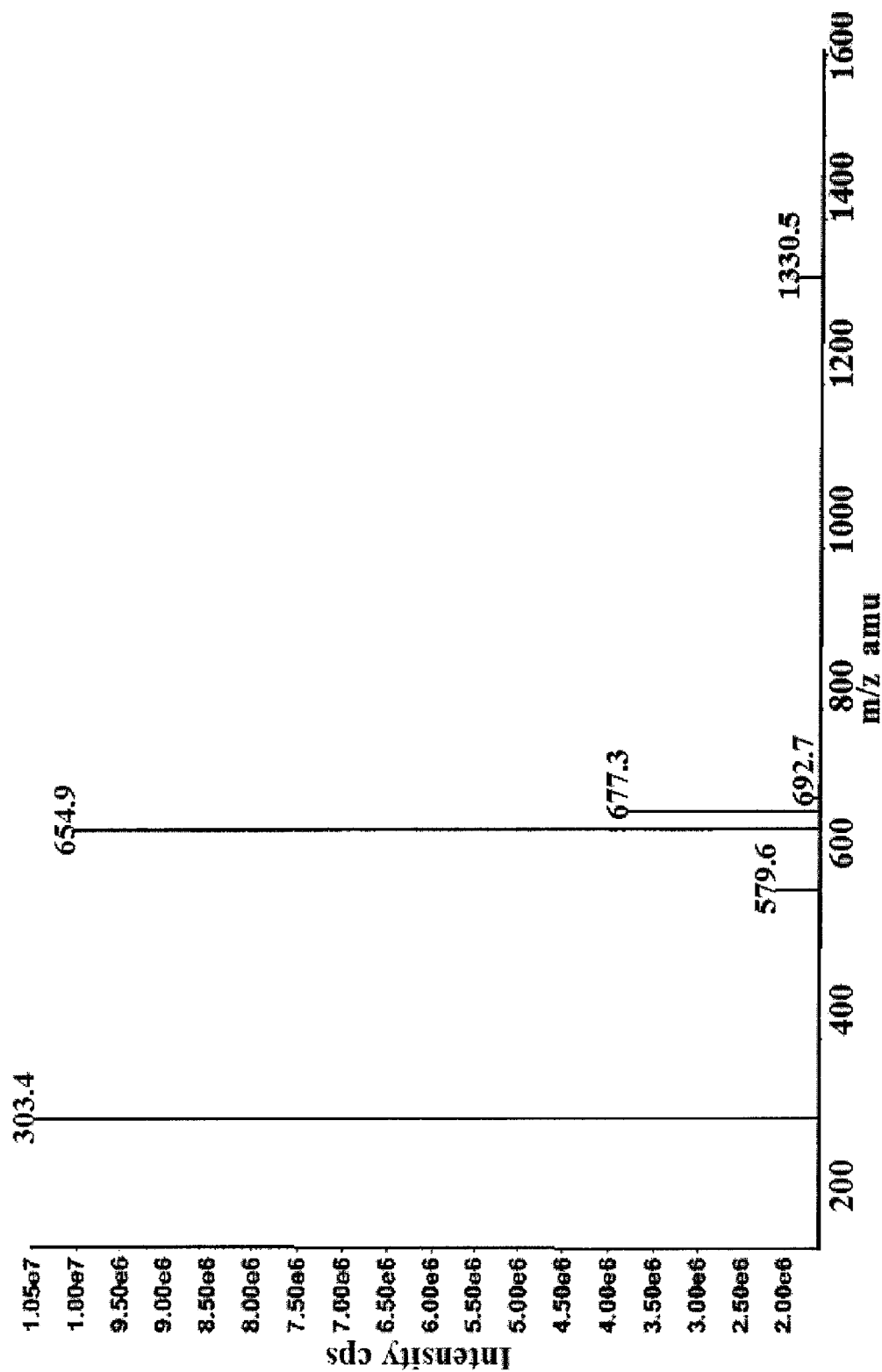
FIG. 19D is a $^1$H-NMR spectrum of 5'-O-dimethoxytrityl-2',3',4',5',5"penta deuterium β-D ribofuranosyl-N$^4$ Benzoyl Cytidine (compound XIX)
Figure 20A:
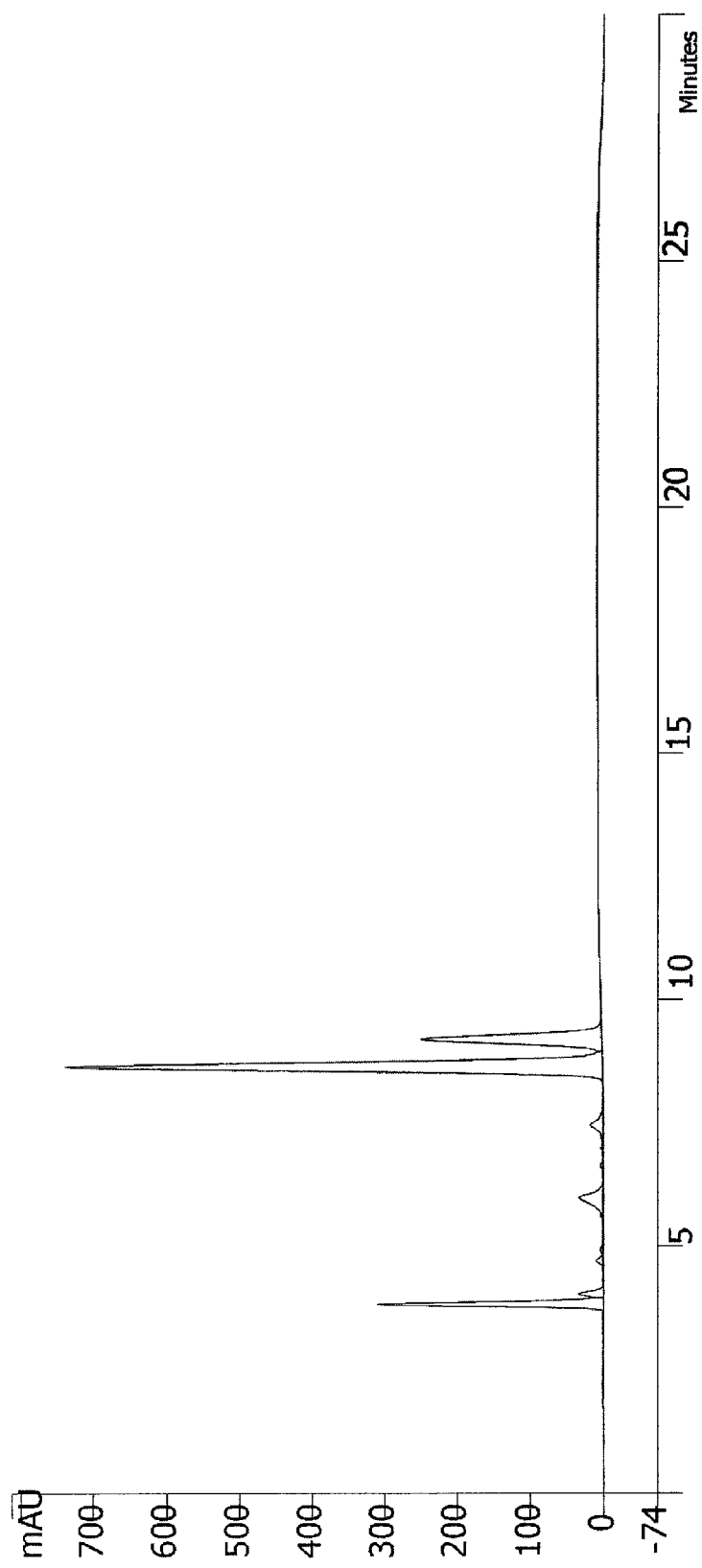
FIG. 20A is a HPLC chromatogram of 5'-O-dimetoxytrityl-2'-O-terbutyldimethyl Silyl-3'-N,N-diisopropyl cyanoethyl phosphoramidite-2',3',4',5',5"penta deuterium β-D ribofuranosyl-N$^4$ benzoyl Cytidine (structure XXII); Purity: 78.88%.
Figure 20C:
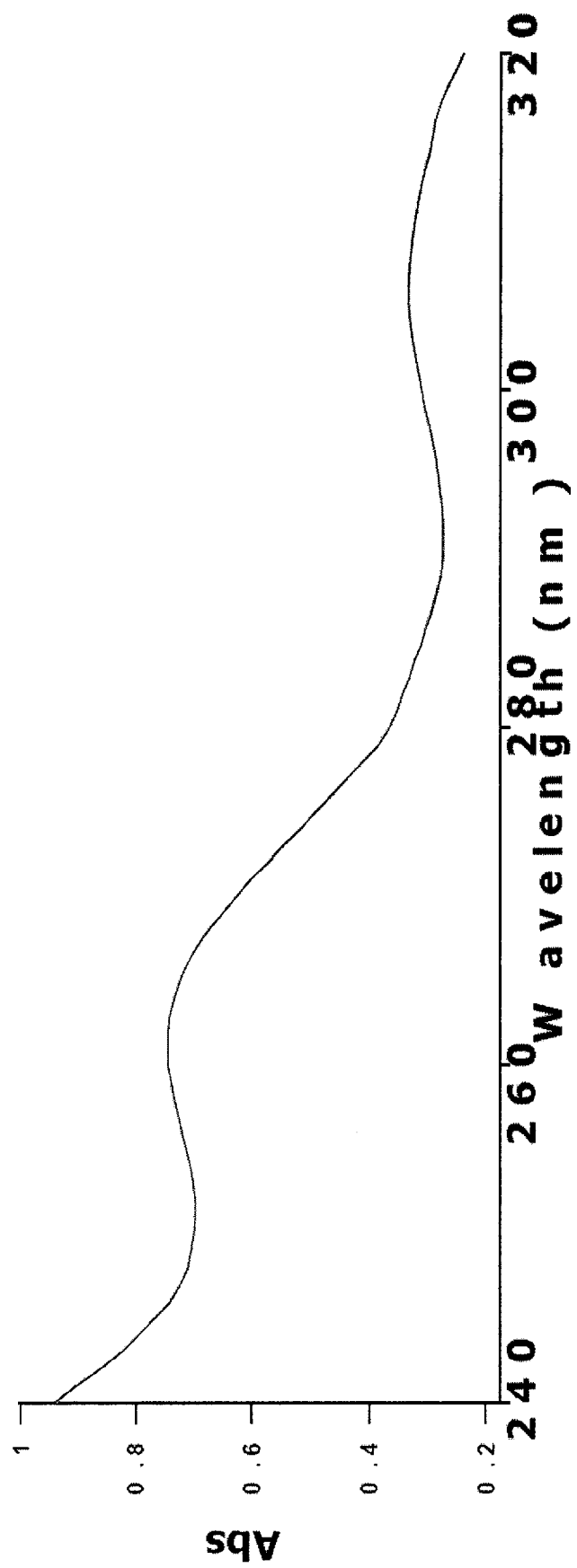
FIG. 20C is a UV analysis of 5'-O-dimethoxytrityl-2'-O-terbutyldimethyl Silyl-3'-N,N-diisopropyl cyanoethyl phosphoramidite-2',3',4',5',5"penta deuterium β-D ribofuranosyl-N$^4$ benzoyl Cytidine (structure XXII)
Figure 20E:
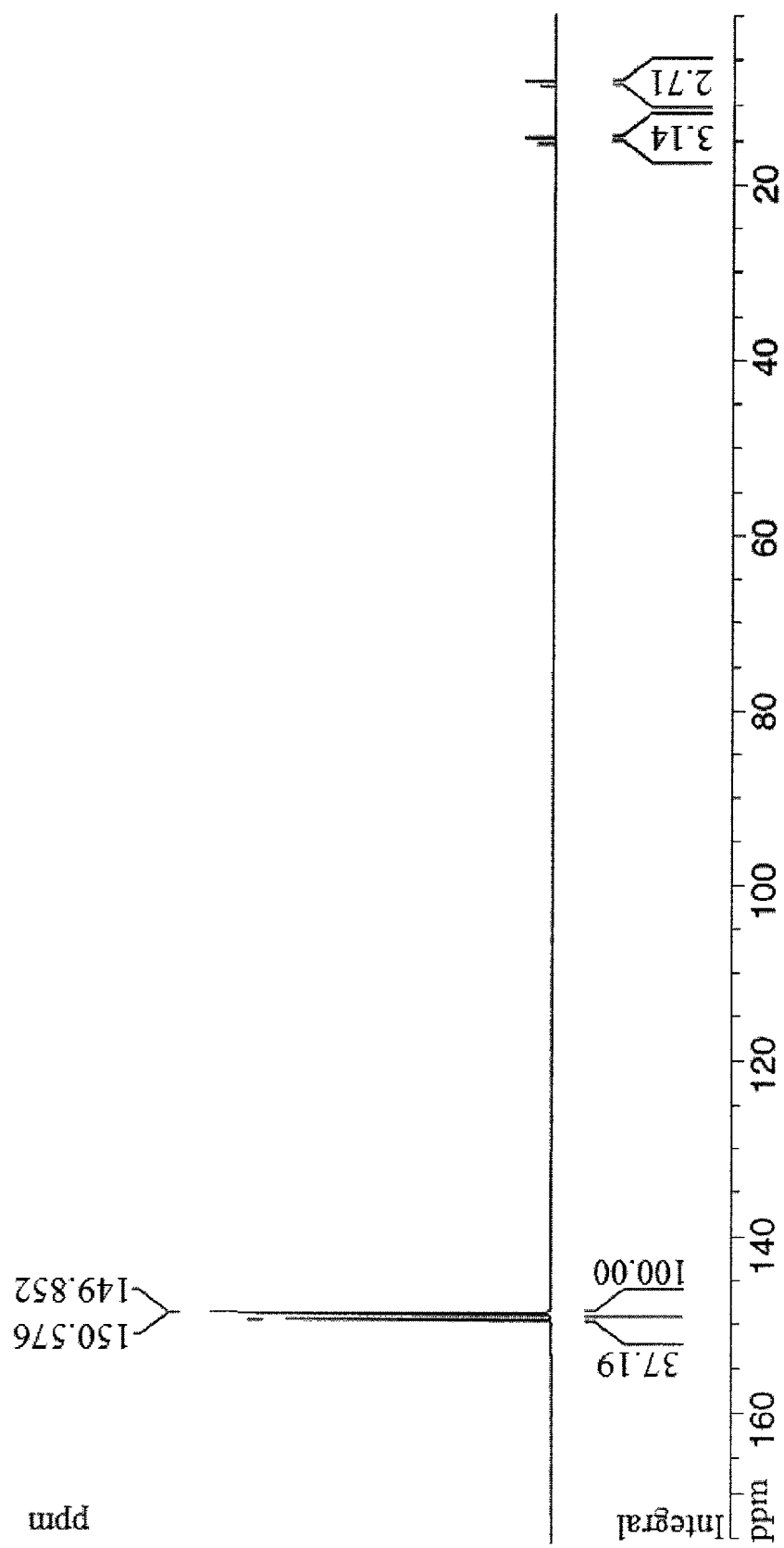
FIG. 20E is a $^{31}$P NMR spectrum of 5'-O-dimetoxytrityl-2'-O-terbutyldimethyl Silyl-3'-N,N-diisopropyl cyanoethyl phosphoramidite-2',3',4',5',5"penta deuterium β-D ribofuranosyl-N$^4$ benzoyl Cytidine (structure XXII); sharp doublet at 150.576 & 149.852 ppm; Purity: 95%; Δ=0.724.
Figure 20F:
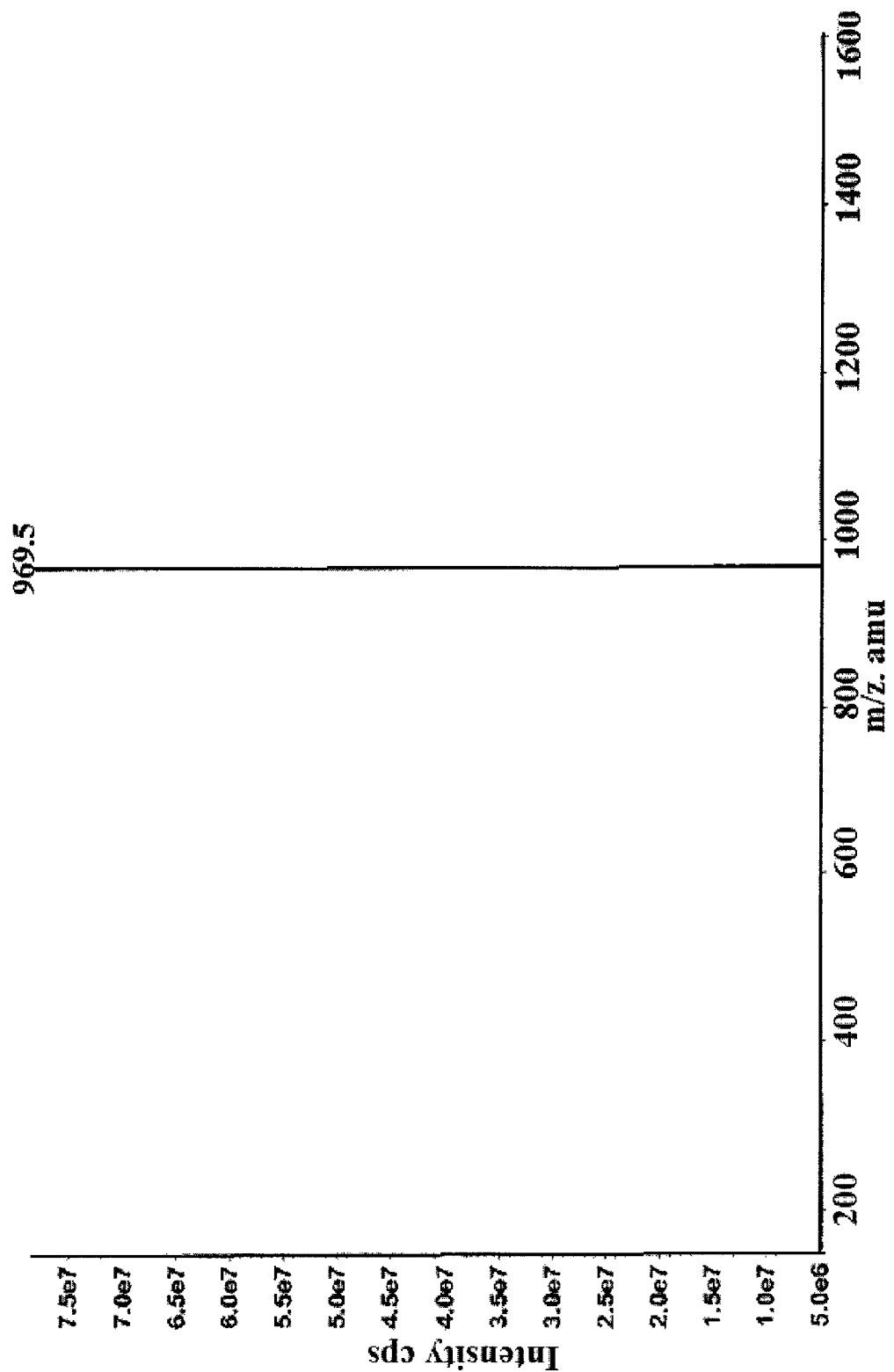
FIG. 20F is a $^{31}$P NMR spectrum of 5'-O-dimetoxytrityl-2'-O-terbutyldimethyl Silyl-3'-N,N-diisopropyl cyanoethyl phosphoramidite-2',3',4',5',5"penta deuterium β-D ribofuranosyl-N$^4$ benzoyl Cytidine (structure XXII); sharp doublet at 150.576 & 149.852 ppm; Purity: 95%; Δ=0.724.

Synthesis of 5'-O-dimethoxytrityl-2'-O-tert-Butyldimethylsilyl-3'-O-succinyl pyridinium salt-2',3',4',5',5"penta deuterium β-D ribofuranosyl Uridine (Compound Structure XIV): The compound, 5'-O-dimethoxytrityl-2'-O-tert-Butyldimethylsilyl-2',3',4',5',5"penta deuterium β-D ribofuranosyl Uridine (XI; 350 mg) was placed in dry pyridine 3.5 ml and stirred. To the stirred solution was added succinic anhydride (158 mg; 1.58 mmol), followed by addition of 4-dimethyl amino pyridine (20 mg; 0.163 mmol). The reaction mixture was sealed and kept in a water bath and maintained at 37° C. for 14 hours. The reaction mixture was checked by TLC and found to be complete. Subsequently, the reaction mixture was quenched with cold methanol (200 microliters), followed by solvent removal on a rotary evaporator. The crude reaction mixture was placed in chloroform and the organic layer was washed with saturated brine solution. The organic layer was filtered through anhydrous sodium sulfate and the chloroform solution was removed under vacuum. The crude compound was purified by a short column chromatography using chloroform:methanol (95:5) solvent system. The pure fractions were combined and evaporated. The foamy product was dried on high vacuum for 6 hours. The Rf value of the product in this system was 0.3. The process yielded 120 mg. The product was analyzed by one or more of the following HPLC, UV, 1 H NMR, mass spectral data and/or $^{31}$P NMR, see FIGS. 17E and 17F.

Synthesis of 5'-O-dimethoxytrityl-2'-O-tert-Butyldimethylsilyl-3 succinyl Icaa-CPG-2',3',4',5',5"penta deuterium β-D ribofuranosyl Uridine (Compound Structure XV): The preceding step nucleoside, 3'-succinate-pyridinium salt, 5'-O-dimethoxytrityl-2'-O-tert-Butyldimethylsilyl-3'-succinyl pyridinium salt-2',3',4',5',5"penta deuterium β-D ribofuranosyl Uridine (compound structure XIV; 85 mg) was placed in a round bottom flask and thoroughly dried with anhydrous acetonitrile, followed by drying under high vacuum using a direct line for 6 hours. To the solid was added anhydrous acetonitrile (6 ml), followed by addition of O-(Benzotriazole-1-Y-L)-N,N,N,N-tetramethyl-uronium-hexafluoro-phosphate, HBTU; (47 mg; 1.1 equivalents). Diisopropyl ethylamine (39 microliters; 2 equivalents). Was then added. To the solution was added an amino linker Icaa CPG (long chain alkyl amine controlled Pore Glass; 500 a particle size; a product of Prime Synthesis Inc., Pennsylvania; 1.5 g). The mixture was sealed thoroughly and kept at 37° C. for 12 hours. The CPG was filtered, washed with acetonitrile, followed by diethyl ether. The CPG was air dried overnight.

The residual amino group was blocked. The dried CPG was placed in an Erlenmeyer flask, and CAP A solution (a Chem-Genes product, catalog no. RN-1458 consists of acetic anhydride:pyridine:tetrahydrofuron (10:10:80) 10 ml) was added. The suspension was kept at room temperature well sealed for 2 hours. The CPG was filtered, washed with isopropanol, followed by washing with diethyl ether. The completion of complete blocking of the residual amino function was checked by ninhydrin test. A negative ninhydrin test indicates complete capping of residual amino functional group. Trityl determination of the loaded CPG was carried out. The trityl value was 44 μmol/g.

Referring to FIG. 5, Scheme 4 illustrates an example of synthesis of an alternative embodiment of a phosphoramidite in accordance with the instant invention and having with the nucleobase cytosine having the structure XXII. The details of the individual steps involved in the synthesis are outlined below.

Synthesis of 2',3',5'-tri O-benzoyl-2',3',4',5',5"penta deuterium β-D ribofuranosyl $N^4$ benzoyl Cytidine: Structure XVII): A mixture of $N^4$ bz-cytosine; (compound structure XVI; 750 mg; 3.47 mmol), hexamethyl disilazane (HMDS; 19 ml) and ammonium sulphate (32 mg; 0.24 mmol) was boiled under reflux until the $N^4$ bz-cytosine dissolved, approximately 15 hours. Hexamethyldisilazane was then evaporated under vacuum and toluene added. The mixture was shaken and the solvents evaporated out to obtain a residual solid consisting of trimethyl silylated $N^4$ bz-cytosine. The solid residue was used without purification for coupling. Freshly distilled 1,2dichloro ethane (freshly distilled over CaH$_2$), 16 ml was added to the residue. The mixture was stirred at 40° C. Stannic chloride (0.86 ml; 3.29 mmole) was then added at the 40° C. temperature. The reaction was continued for 15 minutes at the 40° C. temperature. Deuterated β-D ribose-1-acetate (structure VI (1.42 gm; 2.79 mmole) solution in 1,2dichloro ethane (4.3 ml; freshly distilled over CaH$_2$) was placed in a pressure equalizing funnel and mounted on top of the reaction flask. The solution was added drop wise and the reaction was boiled under reflux for 2.5 hours. The reaction mixture was cooled and stirred in saturated sodium bicarbonate solution for 1.5 hours. The reaction was filtered through a bed of celite powder. The organic layer was separated and passed through anhydrous sodium sulphate. The reaction mixture was evaporated under vacuum and checked using TLC, in chloroform:methanol: (98:02). The R$_f$ value was 0.46. The reaction yielded 2.14 grams.

Synthesis of 2',3',5'-tri Hydroxy-2',3',4',5',5"penta deuterium β-D ribofuranosyl $N^4$ benzoyl Cytidine (Compound Having Structure XVIII): A mixture of 2',3',5'-tri O-benzoyl-2',3',4',5',5"penta deuterium β-D ribofuranosyl $N^4$ benzoyl Cytidine, structure XVII, (2.14 g; 3.22 mmol) in pyridine (20.5 ml) as stirred until dissolved. Methanol (5 ml) was then added. The solution was cooled to 0° C. and 2N aqueous sodium hydroxide solution (6.26 ml) for selective hydrolysis of O-benzoyl groups was added. The hydrolysis reaction was carried out for 20 minutes at 0° C. while stirring continued. The reaction mixture was carefully neutralized to a pH 7.5 with 2N aqueous HCl (7 ml). The solution was evaporated after addition of pyridine (10 ml). The residue was co-evaporated with isopropyl alcohol to dryness. The residue was titrated with distilled water to give a colorless solid. The solid was filtered, washed with diethyl ether and dried under high vacuum. A compound having structure XII was obtained as a powder (yield 1.0 g; 88.49%). The Rf value was 0.5 in chloroform:methanol: (85:15); UV max. at 260 (0.903), and Emax of 16,000. The product was analyzed by one or more of the following HPLC, UV, 1H NMR, mass spectral data and/or $^{31}$P NMR, see FIGS. 18A-18D.

Synthesis of 5'-O-dimethoxytrityl-2',3',4',5',5"penta deuterium β-D ribofuranosyl $N^4$ Benzoyl Cytidine (Compound Having Structure XIX): Compound 2',3',4',5',5"penta deuterium β-D ribofuranosyl $N^4$ Benzoyl Cytidine (structure XVIII 1.0 g; 2.88 mmol) was dried with dry pyridine two times followed by addition of dry pyridine (10 ml). The solution was stirred and cooled to 0° C. with a drying tube attached. 4,4, dimethoxy trityl chloride (DMT-Cl; 1.15 gm; 3.39 mmol) was added to the solution in two portions at one hour intervals. The progress of the reaction was monitored by TLC in Chloroform: 85:15. After completion of reaction (approx. 4 hours), the reaction mixture was quenched with cooled methanol (5 ml), followed by removal of the solvent on a rotary evaporator. The residual gum was placed in chloroform and washed with a saturated bicarbonate solution once, followed by washing with brine solution. The crude product obtained after removal of the solvent was chromatographed on a column of silica Gel (70:230 mesh size) (150 gm) with chloroform:Hexane:Acetone (50:30:20). Fractions were monitored by TLC and visualized by UV. Rf 0.4 in chloroform:methanol: 94:06. Pure fractions were combined and evaporated to give almost a colorless foam, (yield; 1.5 gm; 81.08%), UV lambda max at 260 nm; Emax; 16609.66 (260 nm). The product was analyzed by one or more of the following HPLC, UV, 1 H NMR, mass spectral data and/or $^{31}$P NMR, see FIGS. 19A-19D.

Synthesis of 5'-O-dimetoxytrityl-2'-O-terbutyldimethyl Silyl-2',3',4',5',5"penta deuterium β-D ribofuranosyl N$^4$ benzoyl Cytidine & 5'-O-dimetoxytrityl-3'-O-terbutyldimethyl Silyl-2',3',4',5',5"penta deuterium β-D ribofuranosyl N$^4$ benzoyl Cytidine (Compound Having Structures XX & XXI): Compound 5'-O-dimetoxytrityl-2',3',4',5',5"penta deuterium β-D ribofuranosyl N$^4$ Benzoyl Cytidine (compound XIII; 1.5 gm; 1.95 mmol) was dried by co-evaporation with anhydrous acetonitrile and under vacuum for several hours. The dried product was placed in anhydrous tetrahydrofuran (THF; 15 ml). To the solution was added silver nitrate (AgNo3 0.49 gm; 2.94 mmol) under anhydrous condition with a drying tube on top of the reaction flask. Dry pyridine (0.60 ml; 7.26 mmol) was added to the mixture and stirred for 10 minute at room temperature. Subsequently, tert-butyldimethyl silyl chloride (TBDMS-Chloride; 0.52 g; 3.52 mmol) under anhydrous conditions to seal the reaction mixture. The mixture was stirred for 2.5 hours at room temperature. The progress of the reaction was monitored by TLC and visualized under UV. The TLC solvent system used first checked using chloroform:Hexane:Acetone (65:25:10) ($R_f$ value was 0.38) and then using ethyl acetate:hexane (50:50). The crude product showed formation of both the 2' isomer (Structure XX) and 3' isomer (Structure XXI). The comparative analysis on TLC with unmodified 2' and 3'-isomers was carried out and the spots co-migrated.

The crude product was chromatographed on a column of silica gel (230:400 mesh) with a solvent system consisting of chloroform:Hexane:Acetone (65:25:10). The fractions were monitored by TLC and visualized by UV. The $R_f$ was 0.38 in the same solvent system. Combined pure fractions were evaporated to give a foam with a yield of 800 mg; of 5'-O-dimetoxytrityl-2'-O-terbutyldimethyl Silyl-2',3',4',5',5"penta deuterium β-D ribofuranosyl benzoyl Cytidine 50.9%. UV A max at 250 nm (0.350); Emax of 1634. The 3'-isomer, 5'-O-dimetoxytrityl-3'-O-terbutyldimethyl Silyl-2',3',4',5',5"penta deuterium β-D ribofuranosyl) N$^4$ benzoyl Cytidine (structure XXI) was not isolated.

Synthesis of 5'-O-dimetoxytrityl-2'-O-terbutyldimethyl Silyl-3'-N,N-diisopropyl cyanoethyl phosphoramidite-2',3', 4',5',5"penta deuterium β-D ribofuranosyl) N$^4$ benzoyl Cytidine (Compound Having Structure XXII): From the preceding step, the 2'-TBDMSilyl isomer (compound XX; 430 mg) was thoroughly dried with anhydrous acetonitrile and placed in a round bottom flask. Anhydrous tetrahydrofuran (2.0 ml) was added and the solution was purged with Argon and replaced with a stopper. To the solution under stirring, 2,4,6-collidine (176 microliter; 5 equivalents) was added, followed by addition of 1-methyl imidazole (21 microliters; 1.0 equivalents). To the stirred solution at room temperature, N,N-diisopropylamino cyanoethyl phosphonamidic chloride (phosphorylating reagent, ChemGenes Catalog No. RN-1505; 119 microliters; 2 equivalents) was added. After 75 minutes, the reaction was found to be complete, and it was worked up by dilution with chloroform. The organic layer was placed in a separatory funnel and washed with saturated aqueous sodium bicarbonate, followed by further washing of the organic layer with brine solution. The organic layer was passed over anhydrous sodium sulfate. The solution was concentrated on a rotary evaporator and checked using TLC with a solvent system of ethyl acetate:hexane:triethylamine: 50:40:10 and ethyl acetate:hexane:triethylamine (30:60:10) and (50:40:10).

The crude product was purified on a column of silica gel (230-400 mesh) having a column diameter 30 cm×1.5 cm. The column was run first in the system using ethyl acetate:hexane:triethylamine (30:60:10) and after removal of upper impurities, the system was changed to ethyl acetate:hexane:triethylamine (50:40:10). The pure fractions were, monitored by TLC, were combined and concentrated. Colorless foamy product was obtained having a dry weight of 125 mg. The product was analyzed by HPLC, UV, 1H NMR, Mass spectral data and $^{31}$P NMR, see FIGS. 20A-20F.

Referring to FIG. 6, Scheme 5 illustrates an example of synthesis of an alternative embodiment of a deuterated solid support structure, illustrated herein as 5'-O-dimethoxytrityl-2'-O-tert-Butyldimethylsilyl-3'-succinyl Icaa-CPG-2',3',4', 5',5"penta deuterium β-D ribofuranosyl N$^4$ benzoyl Cytidine.

Figure 21A:
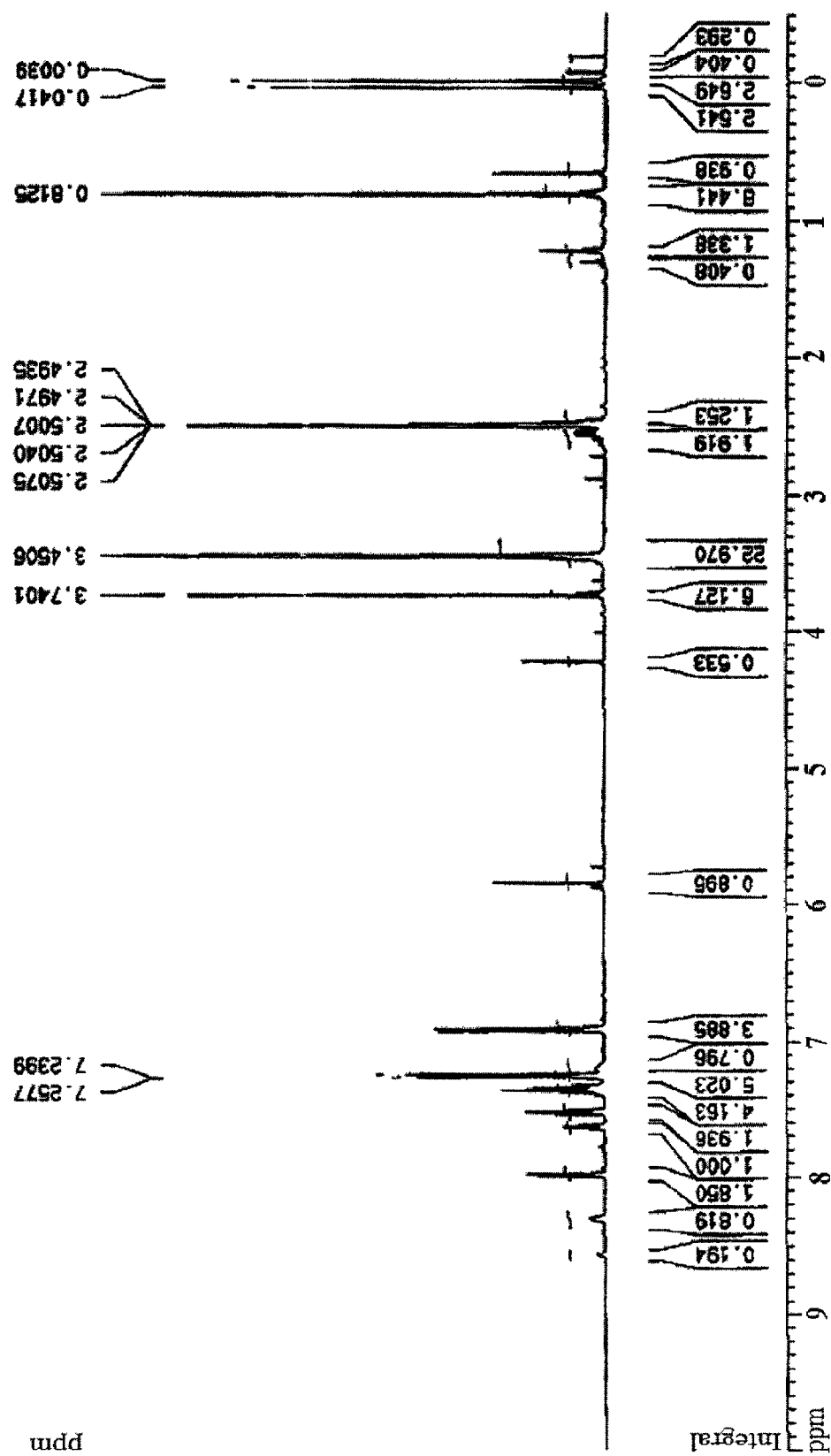
FIG. 21A is a $^{31}$P NMR spectrum of 5'-O-dimetoxytrityl-2'-O-terbutyldimethyl Silyl-3'-N,N-diisopropyl cyanoethyl phosphoramidite-2',3',4',5',5"penta deuterium β-D ribofuranosyl-N$^4$ benzoyl Cytidine (structure XXII); sharp doublet at 150.576 & 149.852 ppm; Purity: 95%; Δ=0.724.
Figure 21B:
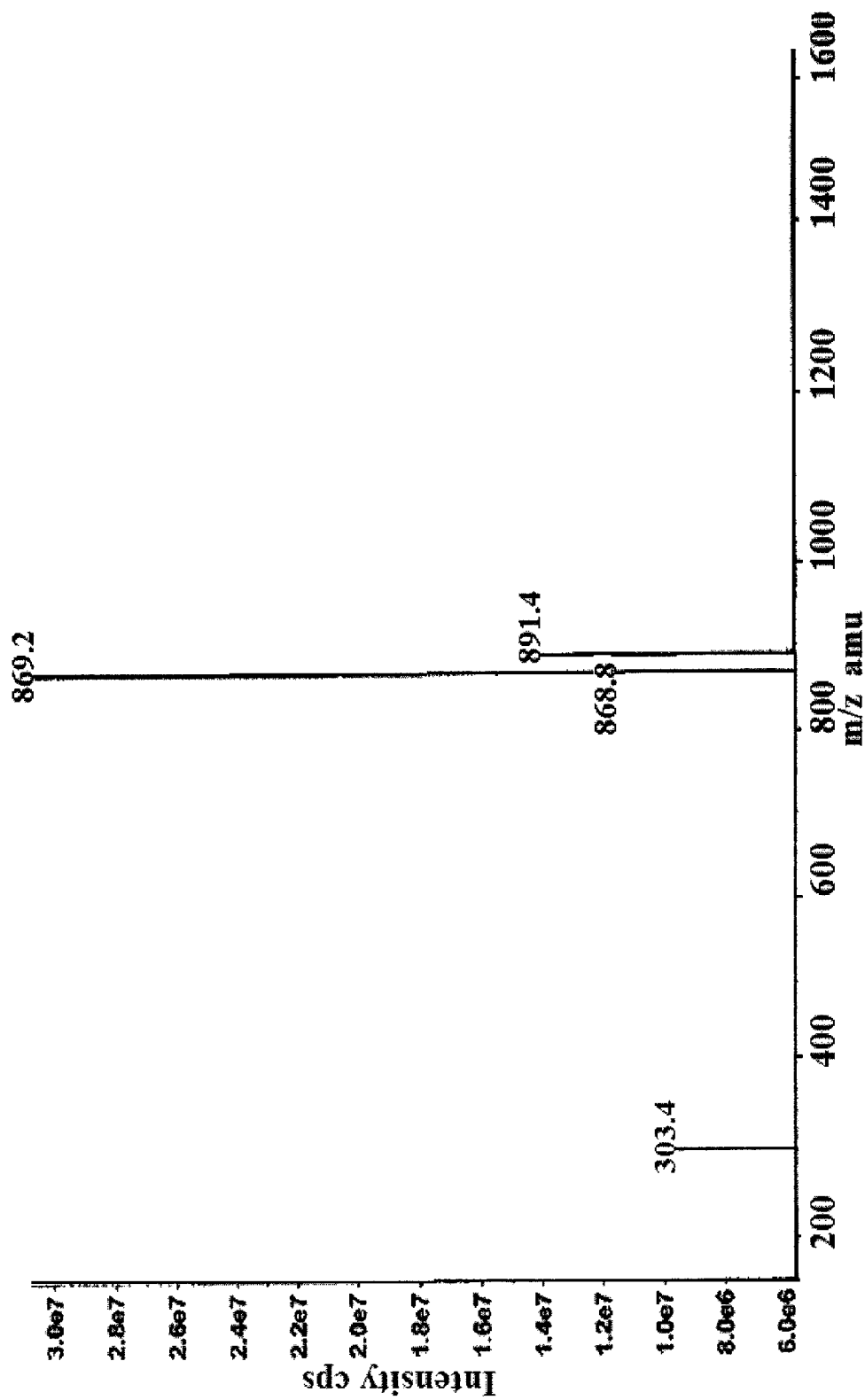
FIG. 21B is a mass spectrum of 5'-O-dimethoxytrityl-2'-O-tert-Butyldimethylsilyl-3'-O-succinyl pyridinium salt-2',3',4',5',5"penta deuterium β-D ribofuranosyl-N$^4$ benzoyl Cytidine (compound structure XXIII); Calculated mass: 867.95; Observed Mass: 869.20.

Synthesis of 5'-O-dimethoxytrityl-2'-O-tert-Butyldimethylsilyl-3'-O-succinyl pyridinium salt-2',3',4',5',5"penta deuterium β-D ribofuranosyl N$^4$ benzoyl Cytidine (Compound Having Structure XXIII): The compound, 5'-O-dimethoxytrityl-2'-O-tert-butyldimethylsilyl-2',3',4',5',5"penta deuterium β-D ribofuranosyl N$^4$ benzoyl Cytidine (structure XXIII); (300 mg) was placed in 3.0 ml dry pyridine. Succinic anhydride (120 mg; 1.99 mmol was added to the stirred solution, followed by addition of 4-dimethyl amino pyridine (14 mg; 0.115 mmol). The reaction mixture was sealed and kept in a water bath maintained at 37° C. for 14 hours. The reaction mixture was checked by TLC and determined to be complete. Subsequently, the reaction mixture was quenched with cold methanol (180 microliters), followed by solvent removal on a rotary evaporator. The crude reaction mixture was placed in chloroform and the organic layer was washed with saturated brine solution. The organic layer was filtered through anhydrous sodium sulfate and the chloroform solution was concentrated under vacuum. The crude compound was purified by a short column chromatography using chloroform:methanol (95:5) solvent system. The pure fractions were combined and evaporated. The foamy product was dried on high vacuum for 6 hours. The $R_f$ value of the product in this system was 0.35. The process yielded 80 mg. The product was analyzed by one or more of the following HPLC, UV, 1 H NMR, mass spectral data and/or $^{31}$P NMR, see FIGS. 21A-21B.

Synthesis of 5'-O-dimethoxytrityl-2'-O-tert-Butyldimethylsilyl-3 succinyl Lcaa-CPG-2',3',4',5',5"penta deuterium β-D ribofuranosyl N$^4$ benzoyl Cytidine (Compound Having Structure XXIV): The preceding step nucleoside, 3'-succinate-pyridinium salt, 5'-O-dimethoxytrityl-2'-O-tert-Butyldimethylsilyl-3'-succinyl pyridinium salt-2',3',4',5', 5"penta deuterium β-D ribofuranosyl N$^4$ benzoyl Cytidine (compound structure XXIII; 40 mg) was placed in a round bottom flask and thoroughly dried with anhydrous acetonitrile, followed by drying under high vacuum using a direct line for 6 hours. Anhydrous acetonitrile (6 ml) was added to the dried material, followed by addition of HBTU; (19.2 mg; 1.1 equivalents), followed by addition of diisopropyl ethylamine (16 microliters; 2 equivalents). To the solution was added an amino linker Lcaa CPG (long chain alkyl amine controlled Pore Glass; 500 A particle size; a product of Prime Synthesis Inc., Pennsylvania; 680 mg). The mixture was sealed thoroughly and kept at 37° C. for 12 hours. The CPG was filtered, washed with acetonitrile, and followed by a diethyl ether wash. The CPG was air dried overnight.

The residual amino groups were blocked. The dried CPG was placed in an Erlenmeyer flask, and CAP A solution (a ChemGenes product, catalog no. RN-1458 consists of acetic anhydride:pyridine:tetrahydrofuran (10:10:80) 10 ml was added. The suspension was sealed and kept at room temperature for 2 hours. Subsequently, the CPG was filtered, washed with isopropanol, followed by a diethyl ether wash. The completion of the complete blocking of the residual amino function was checked by ninhydrin test. A negative ninhydrin test indicated complete capping of residual amino functional group. The trityl value indicated a loading of 30 μmol/g.

Referring to FIG. 7, Scheme 6 shows an example of the synthesis of an alternative embodiment of a phosphoramidite in accordance with the instant invention, having the nucleobase adenine, structure XXVIII. The details of the individual steps involved in the synthesis are outlined below.

Synthesis of 2',3',5'tri-O-benzoyl-2',3',4',5',5"-penta deuterium β-D ribofuranosyl $N^6$ Benzoyl Adenosine (Compound Having Structure XXVI): A mixture of $N^6$ bz-adenine (XXV; 760 mg; 3.18 mmol) was placed in distilled 1,2-dichloroethane and stirred. Bissily acetamidite (BSA; 3.116 ml; 15.29 mmol) was added and boiled under reflux until the $N^6$ bz-adenine was dissolved (15 hr). Subsequently BSA was evaporated under a vacuum & toluene was added. The mixture was shaken and the solvents were evaporated to obtain a residual solid consisting of silylated $N^6$ bz-adenine. The solid was used without purification for coupling. Freshly distilled 1,2dichloro ethane (50 ml; freshly distilled over $CaH_2$), was added to the residue. The mixture was stirred at 40° C., followed by addition of stannic chloride (0.55 ml; 0.73 mmol) at this temperature. The reaction was continued for 15 minutes at 40° C. Deuterated β-D ribose-1-acetate (structure VI (1.29 g; 2.53 mmol) solution in 1,2dichloro ethane (4.3 ml; freshly distilled over $CaH_2$) was placed in a pressure equalizing funnel and was mounted on top of the reaction flask above. The solution was added drop wise and the reaction was boiled under reflux for 2.5 hours.

The reaction mixture was cooled. Saturated sodium bicarbonate solution was stirred in for 1.5 hours. The reaction was filtered through a bed of celite powder. The organic layer was separated and passed through anhydrous sodium sulphate. The reaction mixture was evaporated under vacuum and checked using TLC, using chloroform:ethylacetate:triethylamine (47:47:8). The $R_f$ value was determined to be 0.53.

The crude product was purified by column chromatography (silica gel; 230-400 mesh), using a solvent system of chloroform:ethylacetate:triethylamine (47:47:6) The pure fraction, monitored by TLC, was combined and concentrated on a rotary evaporator. Pure foamy product was obtained having a yield of 400 mg.

Synthesis of 2',3',5'tri Hydroxy-2',3',4',5',5"-penta deuterium β-D ribofuranosy) N6 benzoyl Adenosine (Compound Having Structure XXVII): The preceding tribenzoyl compound, 2',3',5'tri-O-benzoyl-2',3',4',5',5"-penta deuterium β-D ribofuranosyl N6 Benzoyl Adenosine (XXVI; 400 mg) was placed in pyridine (4.8 ml) and methanol (1.2 ml). The mixture was stirred to bring the compound to solution. The solution was then cooled to 0° C. with an ice bucket outside. To the solution, 2N NaOH (1.16 ml) was added, and the basic reaction mixture was hydrolyzed to remove O-benzoyl groups, for a period of 20 minutes. To the reaction mixture was then added 2N HCl (cooled to 0° C.). The addition was done carefully to neutralize the basic solution to pH 7.5 (using 1.0 ml 2 N HCl). To the reaction mixture, pyridine (5 ml) was added and the solution was concentrated. Co-evaporation with pyridine (2×5 ml) followed the concentration step. The residue was purified by crystallization by addition of water. The solid obtained was filtered and washed with diethyl ether. The solution was checked using TLC, using a solvent system of chloroform:methanol (85:15). The vacuum dried product had an $R_f$ value of 0.4 and with a yield of 200 mg.

Figure 22A:
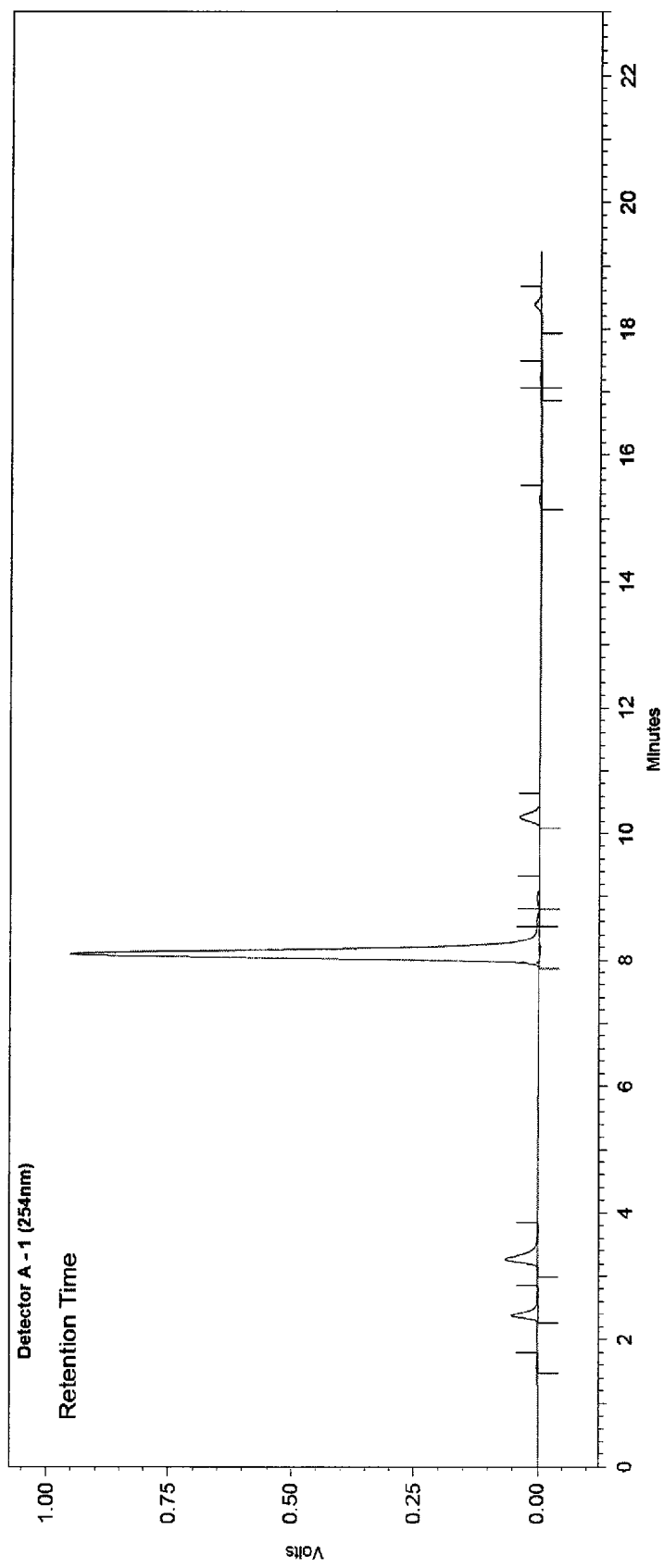
FIG. 22A is a HPLC chromatogram of 5'-O-dimethoxy trityl-2'3',4',5',5"-penta deuterium β-D ribofuranosyl-N$^6$ benzoyl Adenosine (structure XXVIII)
Figure 22C:
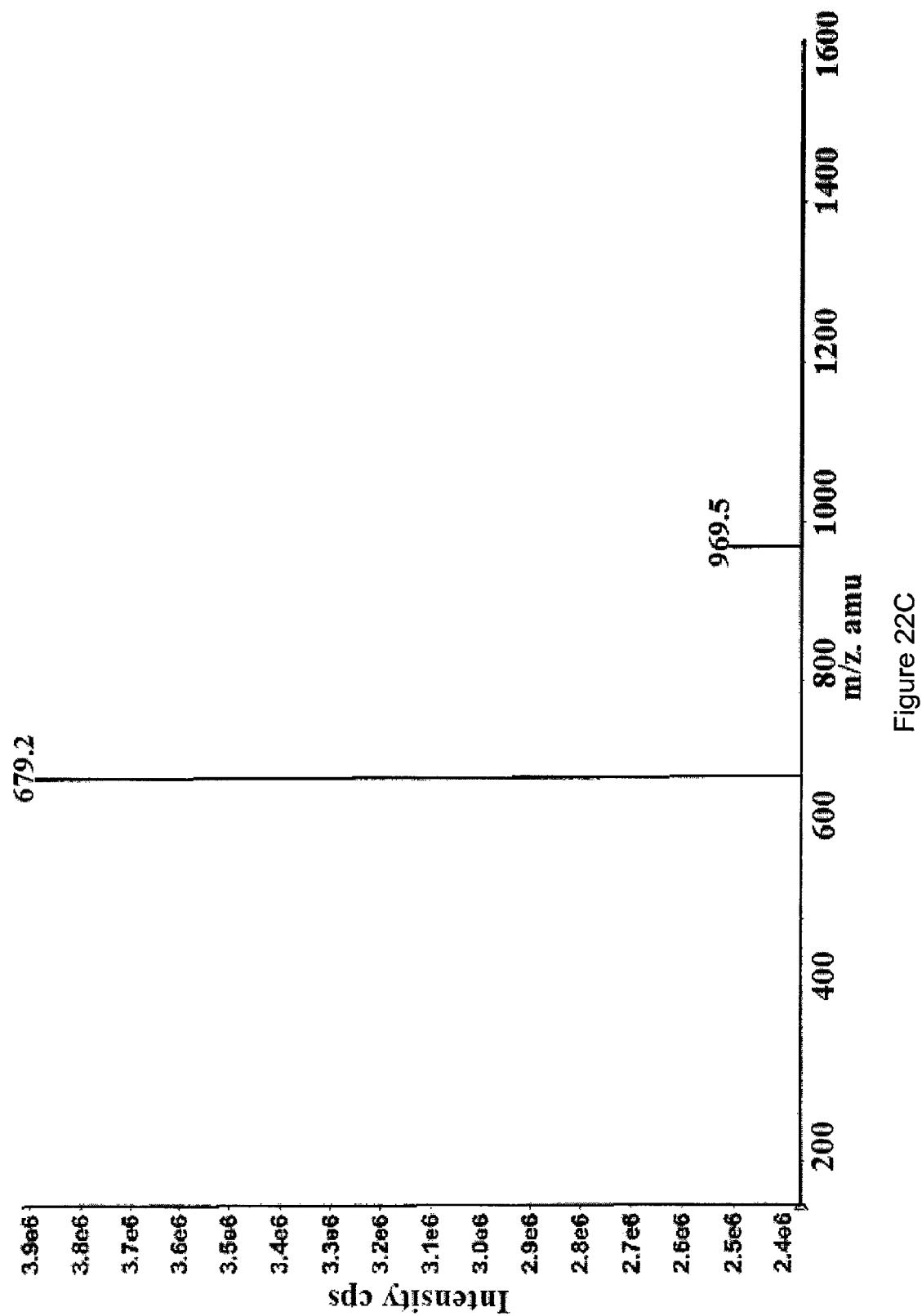
FIG. 22C mass spectrum of 5'-O-dimethoxy trityl-2'3',4',5',5"-penta deuterium β-D ribofuranosyl-N$^6$ benzoyl Adenosine (structure XXVIII); Lot #09015RDV Calculated mass: 678.28; Observed Mass: 679.2.

Synthesis of 5'-O-dimethoxy trityl-2',3',4',5',5"-pentadeuterium β-D ribofuranosyl $N^6$ benzoyl Adenosine (Compound Having Structure XXVIII): The compound 2',3',5'-tri Hydroxy-2',3',4',5',5"-penta deuterium β-D ribofuranosyl N6 benzoyl Adenosine (XXVII; 200 mg) was dried with dry pyridine two times followed by addition of dry pyridine (2M) under anhydrous conditions. The solution was stirred and cooled to 0° C. with a drying tube attached. To the solution was added 4,4, dimethoxy trityl chloride (DMT-Cl; 0.21 g; 0.619 mmol) in one portion. The progress of the reaction was monitored by TLC in Chloroform (95:05). After completion of the reaction (approximately 4 hours), the reaction mixture was quenched with cooled methanol(2 ml). The solvent was then removed on rotary evaporator. The residual gum was placed in chloroform and washed with saturated bicarbonate solution once, followed by a single wash with brine solution. The crude product obtained after removal of the solvent was chromatographed on a column of silica Gel (70:230 mesh size) (150 gm) with chloroform:methanol(95:5) as an eluant. Fractions were monitored by TLC and visualized by UV. The $R_f$ value was 0.38 in chloroform:methanol(95:05). Pure fractions were combined and evaporated to give almost colorless foam. The process yielded 80 mg; UVmax at 250 nm; $E_{max}$ of 11,671. The product was analyzed by one or more of the following HPLC, UV, 1 H NMR, mass spectral data and/or $^{31}P$ NMR, see FIGS. 22A-22C.

Oligonucleotide Synthesis: Using Schemes 1-6 to synthesize the necessary chemical structures, the instant invention describes an oligonucleotide synthesis process for the production of deuterated ribonucleotides. Referring to FIG. 8A, illustrative example of a deuterated ribo-oligonucleotide having structure C1 is shown, wherein n represents the number of nucleoside units (ribose+nucleobase) of the oligonucleotide, thereby defining the oligonucleotide sequence, B represents natural or modified nucleobase, and X is deuterium, wherein W could be oxygen ($O^-$) or Sulfur ($S^-$); Y could be oxygen ($O^-$) C1-C18 alkoxy, C1-18 alkyl; NHR3 with R3 being C1-C18 alkyl or C1-C4 alkoxy-C1-C6-alkyl; NR3R4 in which R3 is as defined above and R4 is C1-C18 alkyl, or in which R3 is as defined above and R4 is C1-C18-alkyl, or in which R3 and R4 form together with the nitrogen atom carrying them, a 5-6 membered heterocyclic ring which can additionally contain another hetero atom from the series O, S and N. Alternatively, the oligonucleotide linkage could contain a Y-group which be replaced with X—C—$(Y_1Y_2Y_3Y_4)$—, represented by Formula II:

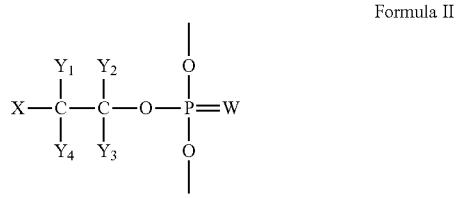

Formula II wherein W can be oxygen ($O^-$) or sulfur ($S^-$); Y can be singly or multiply hydrogen, methyl, ethyl; X can be an electron attracting group, such but not limited to, halogen, such as fluorine, chlorine, or bromine, CN, $NO_2$, $SO_2$, aromatic groups such as but not limited to phenyl thio, phenyl sulfoxy, phenylsulfonyl. The phenyl ring groups can be substituted with halogen, CN, $NO_2$. It is also possible for [X—C—($Y_1$, $Y_2$)] in formula II to be replaced by CF, CCl, or $CBr_3$.

The number of nucleoside units of the oligonucleotide may be for example 2-200, preferably less than 100, and most preferably between 2 and 50. The oligonucleotide unit may have deuterium levels in the range of 1% to 98% accomplished by dilution with cold material. For example, the oligonucleotide having 100% deuteration may be serially diluted with cold RNA for final concentrations of between 0.1% and 98%. As illustrated in FIG. 9A, the oligonucleotide preferably contains a phosphodiester internucleotide linkage. FIG. 9B illustrates an alternative embodiment of the deuterated oligonucleotide illustrated in FIG. 8 having a phosphate backbone variant illustrated as, but not limited to, phosphorothioate internucleotide linkages. Phosphorothioate modifications have been shown to be useful for delivering biologically active oligonucleotides, see *Protocols for Oligonucleotides and Analogs*, Editor, Sudhir Agarwal, Humana Press, Totawa, N.J., 1993. Moreover, use of variant backbones such as phosphorothioate can be useful in resisting degradation by cellular enzymes, thereby providing a more stable modified oligonucleotide.

The phosphorylating reagents, N,N-diisopropylamino cyanoethyl phosphonamidic chloride or 2-cyanoethyl, N,N,N,N-tetraisopropyl phosphane are readily commercially available and were produced by ChemGenes Corp (Wilmington, Mass.). High purity dimethoxytriphenyl chloride (DMT-chloride) was obtained from Esscee Biotech India Pvt. Ltd. High purity pyridine was obtained from Caledon Laboratories.

The oligonucleotides listed in Table 1 were synthesized using 3'→5' directed deuterated nucleoside-2'-tertbutyl dimethyl silyl-3'-cyanoethyl phosphoramidites as well as standard or natural RNA phosphoramidite chemistry in 1 μmole scale. The syntheses were performed on Expedite 8900 synthesizer using standard RNA 1 μmole cycle.

TABLE 1

Deuterated/Natural Oligonucleotide sequences synthesized by conventional synthesis method.

| SEQ ID NO | SEQUENCE (5' to 3,) |
|---|---|
| SEQ ID NO: 1 | CUCUCUCUCUCU |
| SEQ ID NO: 2 | CAUUGGUUCAAACAU |
| SEQ ID NO: 3 | AGGUUCAAACAU |

Following synthesis of the desired oligonucleotide, the controlled pore glass (CPG) solid support was transferred to a 2 ml microfuge tube. Oligonucleotides were cleaved from the CPG and deprotected by incubation for 30 min at 65° C. in 1 ml of 40% methylamine solution in water. The supernatant was removed and the CPG was washed with 1 ml of water. Supernatants were pooled and dried. The t-butyl-dimethylsilyl protecting group was removed from the RNA residue by treatment with 250 μl of fresh anhydrous triethylammonium-trihydrogen fluoride at room temperature in ultrasonic bath for 2 hours. The oligonucleotide was precipitated by 1.5 ml of n-butanol. The sample was cooled at −20° C. for 1 hour then centrifuged at 10,000 g for 10 minutes.

After the supernatant was decanted, the pellet was washed with n-butanol one additional time.

The oligonucleotide was then purified by Ion-Exchange HPLC using a linear gradient in buffer A=(10.0%, 0.5M TRIS and 10.0% ACN), pH 7.5 and buffer B=1.0 M Lithium Chloride in buffer A. The entire sample was loaded on a Source15Q column (1.0 cm×25 cm) and eluted with a linear 5% to 75% acetonitrile gradient over 40 minutes. Samples were monitored at 260 nm and peaks corresponding to the desired oligonucleotide species were collected, and precipitated by adding 5.0 volume of (2% $LiClO_4$, in acetone), followed by centrifuging at 10,000 g for 10 minutes. The supernatant was decanted, and the pellet was washed with ethanol.

General Procedure for 1.0 μmol phosphodiester of oligonucleotide synthesis is described below. Amidites (solid) used for the specific sequence of interest were individually placed in a 20 mL expedite bottle and dissolved in a quantity of dry acetonitrile to make the solution 0.075M. The bottles were flushed with Argon and shaken after sealing the screw cap promptly to dissolve the solid completely. The monomer solution bottles were then screwed in to the synthesizer. In addition, 1.0 um expedite column with Product 5'-O-DMT-2'-O-tert-Butyldimethylsilyl-Uridine-3'-succinyl lcaa—A support produced by ChemGenes Corp., Cat # N-6104. Natural RNA base loaded support was prepared and attached to the synthesizer. Table 2 illustrates the oligonucleotide synthesis scheme using an automatic DNA/RNA Synthesizer.

TABLE 2

Oligonucleotide synthesis on an automated DNA/RNA Synthesizer:

| | # of Cycles | Reagent | Wait Time (sec) | Volume (μl) |
|---|---|---|---|---|
| Cycle 1 | | | | |
| Prewash | 2 | Synthesis Grade Acetonitrile | — | 350 |
| RNA Protocol Cycle 2a | | | | |
| Deblock | 2 | 3% TCA/DCM | 60 | 150 |
| Wash | 3 | Synthesis Grade Acetonitrile | — | 350 |
| Coupling | 1 | Ribo-sugar (deuterated) nucleoside amidites (0.075M concentration) | 600 | 255 |
| Activator | 1 | 5-Ethylthio Tetrazole (0.35M) | | 120 |
| Wash | 1 | Synthesis Grade Acetonitrile | — | 350 |
| Cap A | 1 | Acetic anhydride/THF/Pyridine | 50 | 120 |
| Cap B | 1 | N-Methyl imidazole/THF | | 100 |
| Wash | 1 | Synthesis Grade Acetonitrile | — | 350 |
| Oxidize | 1 | 0.02M Iodine in Pyridine/THF/Water | 25 | 100 |
| Wash | 3 | Synthesis Grade Acetonitrile | — | 350 |

After completion of the synthesis per summary of the key features as listed in the Table 2, the controlled pore glass (CPG) solid support was washed with 3.0 ml diethyl ether and transferred to a 2 ml microfuge tube. Oligonucleotide 1 was cleaved from the CPG and deprotected by incubation for 30 min at 65° C. in 1 ml of 40% methylamine solution in water. The supernatant was removed and the CPG was washed with 1 ml of water. The supernatants were pooled and dried. The t-butyl-dimethylsilyl protecting group was removed from the RNA residue by treatment with 500 μl of fresh 12.0% solution of tetraethyl ammonium fluoride in DMSO, at 45° C. in an ultrasonic bath for 1 hour. Oligonucleotide 1 was precipitated with 1.5 ml of n-butanol. After precipitation, the sample was cooled at −20° C. for 1 hour then centrifuged at 10,000 g for 10 minutes. The supernatant was decanted, the pellet was washed with n-butanol one time. A final wash with 500 µl ethanol was performed. The sample was centrifuged at 10000 rpm for 5 minutes. Following centrifugation, the supernatant was decanted. The pellet was dissolved in 1000 µl M·Q water. The optical density, OD, (Crude desalt) of the sample was measured. The oligonucleotide was then purified by Ion-Exchange HPLC using a linear gradient in buffer A (10.0%, 0.5M TRIS and 10.0% ACN), pH 7.5 and buffer B (1.0 M Lithium Chloride in buffer A).

The entire sample was loaded on a Source 15Q column (1.0 cm×25 cm) and eluted with a linear 5% to 75% acetonitrile gradient over 40 minutes. Samples were monitored at 260 nm and peaks corresponding to the desired oligonucleotide species were collected, and precipitated by adding 5.0 volume of 2% LiClO$_4$, in acetone, followed by centrifugation at 10,000 g for 10 minutes. The supernatant was decanted, and the pellet was washed with ethanol.

Oligonucleotide Synthesis Example 1

Oligonucleotide 1A

Oligonucleotide 1A was synthesized to have a sequence according to SEQ ID NO: 1, rC*rU*rC*rU*rC*rU*rC*rU* rC*rU*rC*rU*, wherein r is a ribose sugar and * represents deuterated ribose resulting from using deuterium labeled phosphoramidites in the synthesis process. Oligonucleotide 1A was synthesized using 5'→3' approach, directed with deuterated RNA phosphoramidite chemistry in 1 mmol scale. The synthesis was performed on Expedite 8900 synthesizer using standard RNA 1 mmol cycle and a coupling time of the monomers with solid support of 10.0 minutes.

Figure 23A:
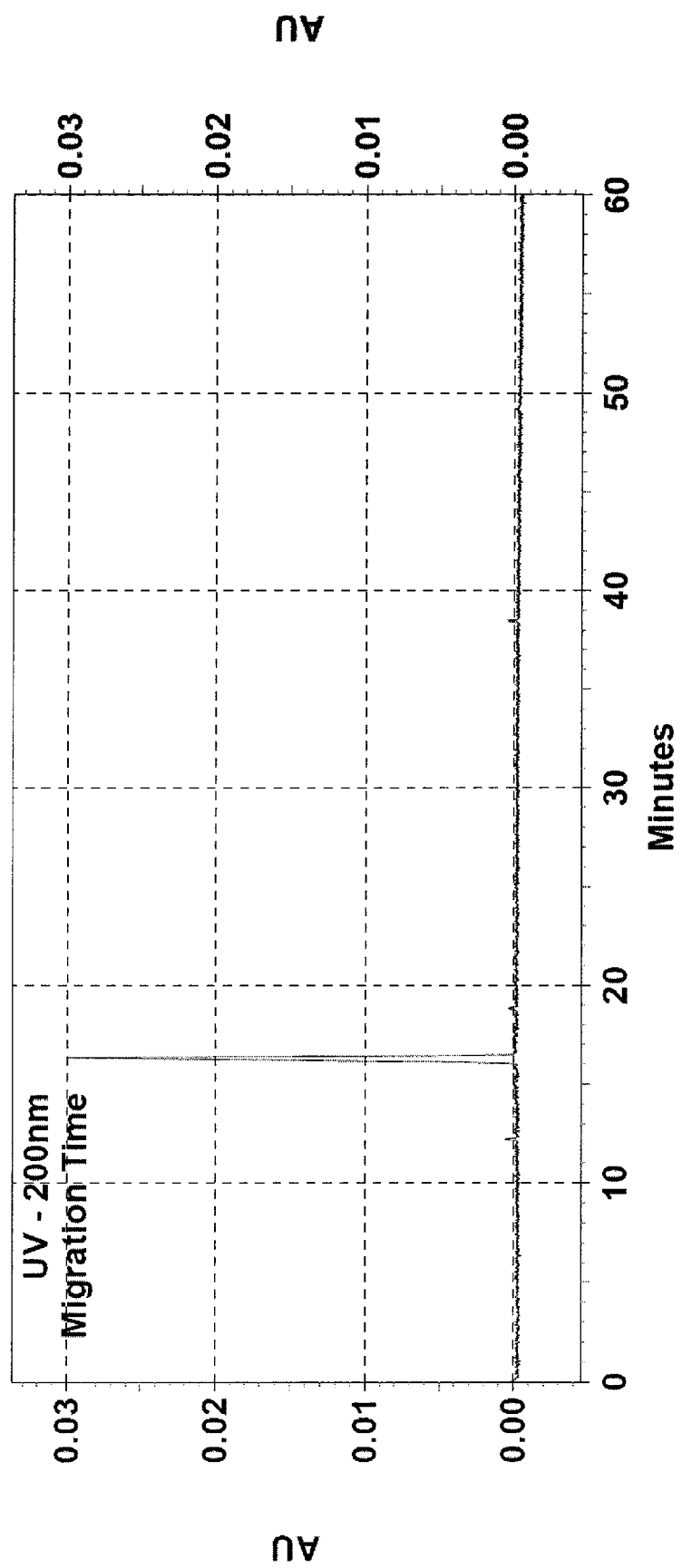
FIG. 23A is a capillary electrophoresis analysis of the purified oligonucleotide of SEQ ID No.1, fully deuterated RNA.
Figure 23C:
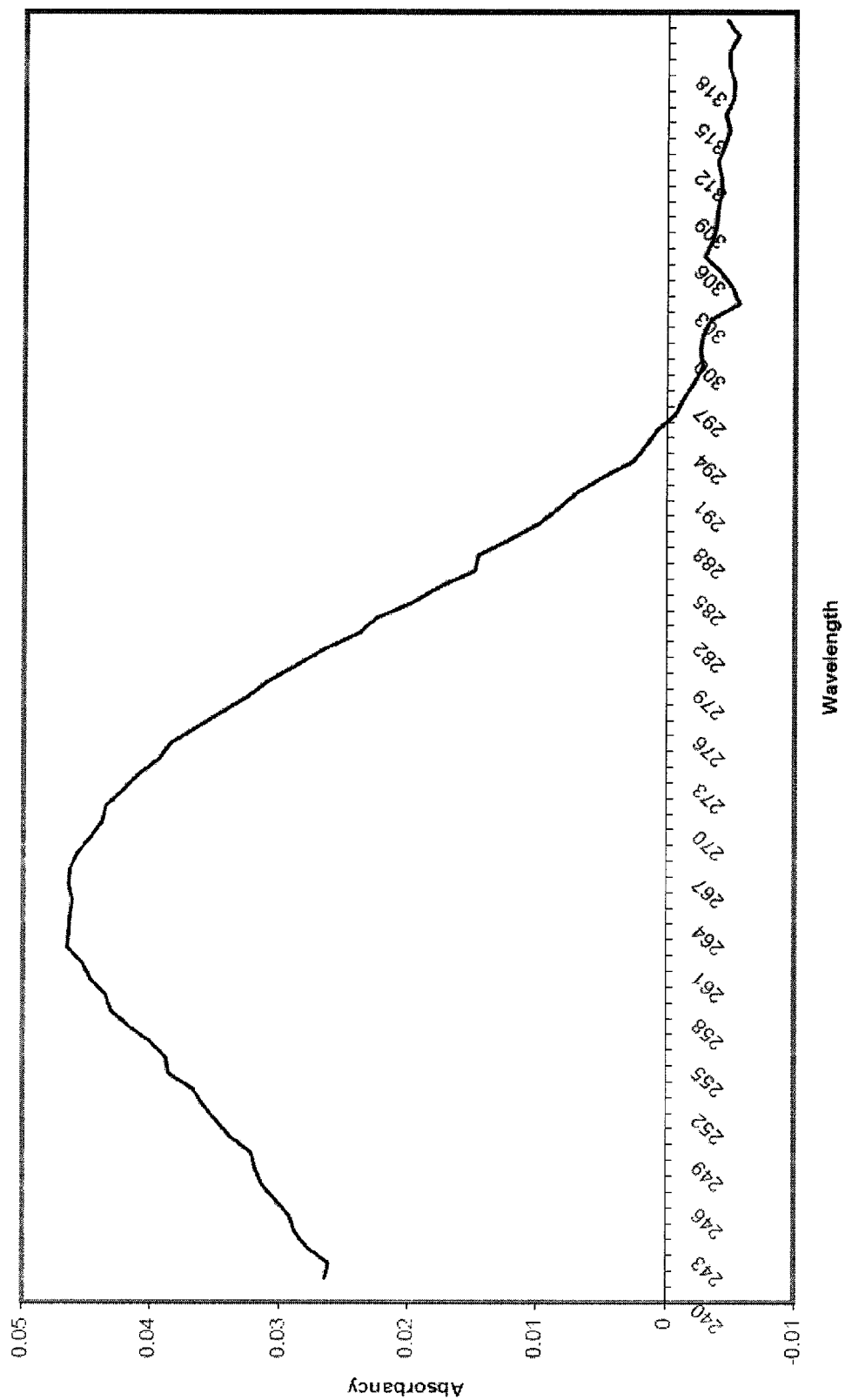
FIG. 23C is a UV analysis of the purified oligonucleotide SEQ ID No.1, fully deuterated RNA.

The Amidites used were: (A) 1-(5-O-dimethoxytrityl-2-O-tert-Butyldimethylsilyl-3-N,N-diisopropylcyanoethyl phosphoramidite-2,3,4,5penta deuterium β-D ribofuranosyl) Uracil, structure XIII; and (B) 1-(5-O-dimetoxytrityl-2-O-terbutyldimethyl Silyl-3-N,N-diisopropyl cyanoethyl phosphoramidite-2,3,4,5 penta deuterium β-D ribofuranosyl) N$^4$ benzoyl Cytosine (compound structure XXII). The solid support used was 1-(5-O-dimethoxytrityl-2-O-tert-Butyldimethylsilyl-3-succinyl Icaa-CPG-2,3,4,5-penta deuterium β-D ribofuranosyl) Uracil (compound structure XV). Results of capillary electrophoresis analysis are illustrated in FIGS. 23A-23C.

Oligonucleotide Synthesis Example 2

Oligonucleotide 1B

Oligonucleotide 1B was synthesized to have a sequence according to SEQ ID NO: 1, rCrUrCrUrCrU rCrUrCrUrCrU wherein r is a ribose sugar and ** represents a mixture of deuterated ribose and natural, unmodified ribose modified resulting from synthesis using deuterium labeled phosphoramidites and a mixture with natural unmodified nucleoside phosphoramidite in a ratio of 25:75. Oligonucleotide 1B has approximately 25% deuterium label was synthesized using 5'→3' directed RNA phosphoramidite chemistry in 1 µmol scale. The synthesis were performed on Expedite 8900 synthesizer using standard RNA 1 µmol cycle and coupling time of the monomers with solid support 10.0 minute.

The Amidites used were: (A) 1-(5-O-dimethoxytrityl-2-O-tert-Butyldimethylsilyl-3-N,N-diisopropylcyanoethyl phosphoramidite-2,3,4,5penta deuterium β-D ribofuranosyl) Uracil (structure XIII); (B) 1-(5-O-dimetoxytrityl-2'-O-ter- butyldimethyl Silyl-3'-N,N-diisopropyl cyanoethyl phosphoramidite-2,3,4,5,5'penta deuterium β-D ribofuranosyl) N$^4$ benzoyl Cytidine (XXII); (C) 1-(5-O-dimetoxytrityl-2'-O-terbutyldimethyl Silyl-3'-N,N-diisopropyl cyanoethyl phosphoramidite-2,3,4,5,5'penta deuterium β-D ribofuranosyl) N6 Adenosine. Natural RNA base for mixing natural RNA base in the sequence, ChemGenes Catalog product, ANP-5674; and (D) 5'-O-DMT-2'-O-tert-Butyldimethylsilyl-Cytidine N$^{bz}$-3'-N,N-diisopropyl cyanoethyl phosphoramidite, Natural RNA base, for mixing natural RNA base in the sequence, ChemGenes Catalog product, ANP-5672. The solid supports used were (A) 1-(5-O-dimethoxytrityl-2'-O-tert-Butyldimethylsilyl-3'-succinyl Icaa-CPG-2,3,4,5, 5'penta deuterium β-D ribofuranosyl) Uracil (structure XV) and (B) 5'-O-DMT-3'-O-tert-Butyldimethylsilyl-Uridine-2'-succinyl Icaa—A support produced by ChemGenes Corp., Cat # N-6104. Natural RNA base loaded support was mixed with the Support A listed above in 25:75 ratio to obtain 1.0 micromole column in order to obtain oligonucleotide 1B consisting of 3'-terminal U with a natural U and deuterium modified 3'-terminal U in a ratio of 75:25, for mixed modified RNA base in the sequence.

Oligonucleotide Synthesis Example 3

Oligonucleotide 1C

Oligonucleotide 1C was synthesized to have a sequence according to SEQ ID NO: 1, rCrUrCrUrCrUrCrUrCrUrCrU wherein r is a ribose unit consisting of unmodified natural bases Uridine and Cytidine. The oligonucleotide was synthesized using 3'→5' directed RNA phosphoramidite chemistry in 1 micro mole scale. The synthesis were performed on Expedite 8900 synthesizer using standard RNA 1 micro mole cycle and coupling time of the monomers with solid support 10.0 minute. The amidites used included (A) 5'-O-DMT-2'-O-tert-Butyldimethylsilyl-Uridine-3'-N,N-diisopropyl cyanoethyl phosphoramidite, Natural RNA base for natural RNA base sequence, ChemGenes Catalog product, ANP-5674 and (B) 5'-O-DMT-2'-O-tert-Butyldimethylsilyl-Cytidine N$^{bz}$-3'-N,N-diisopropyl cyanoethyl phosphoramidite, Natural RNA base for mixing natural RNA base sequence, ChemGenes Catalog product, ANP-5672. The sold supports used was 5'-O-DMT-3'-O-tert-Butyldimethylsilyl-Uridine-2'-succinyl Icaa—A support produced by ChemGenes Corp., Cat # N-6104. Natural RNA base loaded support.

Oligonucleotide Synthesis Example 4

Oligonucleotide 2

Figure 24A:
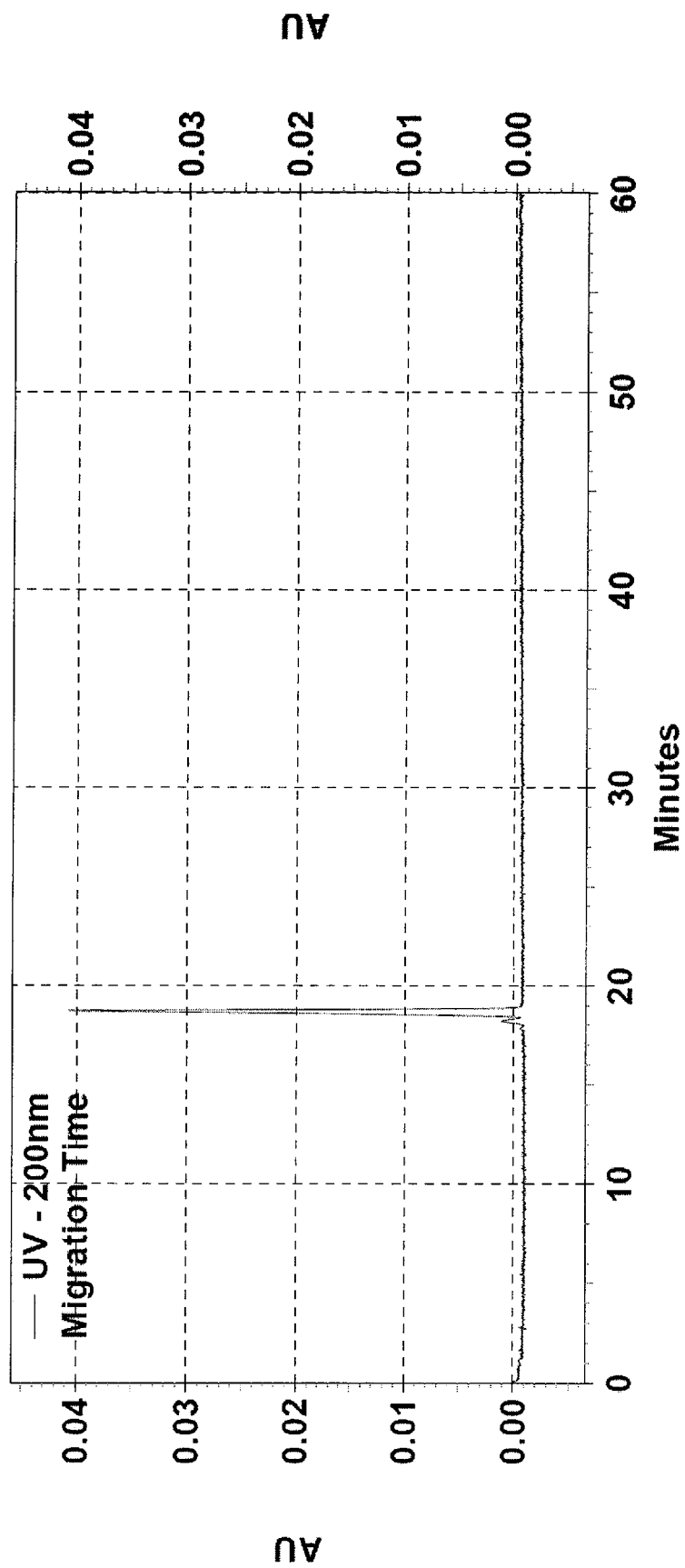
FIG. 24A is a capillary electrophoresis analysis of the purified oligonucleotide SEQ ID No.2, approx. 25% deuterated RNA.
Figure 24C:
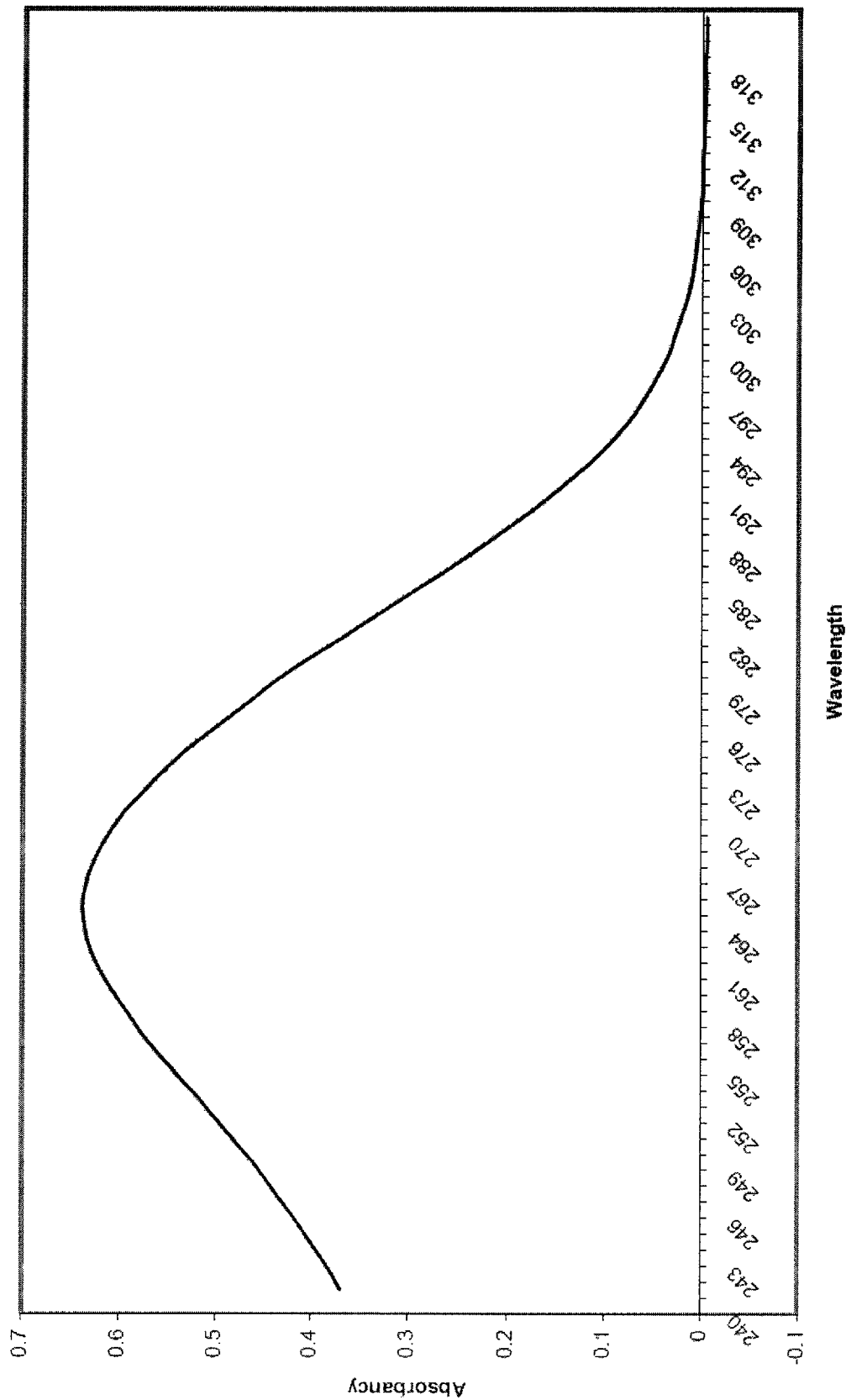
FIG. 24C is a UV analysis of the purified oligonucleotide SEQ ID No.2, approx. 25% deuterated RNA.

Oligonucleotide 2, was synthesized to have a sequence according to SEQ ID NO: 2, consisting of unmodified natural bases uridine, cytidine and adenosine. The oligonucleotide was synthesized using 5'→3' directed RNA phosphoramidite chemistry in 1 micro mole scale. The synthesis were performed on Expedite 8900 synthesizer using standard RNA 1 µmol cycle and coupling time of the monomers with solid support 10.0 minute. The amidites used included (A) 5'-O-DMT-2'-O-tert-Butyldimethylsilyl-Uridine-3'-N,N-diisopropyl cyanoethyl phosphoramidite, Natural RNA base for natural RNA base sequence, ChemGenes Catalog product, ANP-5674; (B) 5'-O-DMT-2'-O-tert-Butyldimethylsilyl-Cytidine N$^{bz}$-3'-N,N-diisopropyl cyanoethyl phosphoramidite, Natural RNA base for natural RNA base sequence, ChemGenes Catalog product, ANP-5672; (C) 5'-O-DMT-2'-O-tert-Butyldimethylsilyl-Adenosine N$^{bz}$-3'-N,N-diisopropyl cyanoethyl phosphoramidite, Natural RNA base for natural RNA base sequence, ChemGenes Catalog product, ANP-5671; (D) 5'-O-DMT-2'-O-tert-Butyldimethylsilyl-Guanosine $N^{ibu}$-3'-N,N-diisopropyl cyanoethyl phosphoramidite, Natural RNA base for natural RNA base sequence, ChemGenes Catalog product, ANP-5673. The solid support used included 5'-O-DMT-3'-O-tert-Butyldimethylsilyl-Uridine-2'-succinyl lcaa—A support produced by ChemGenes Corp., Cat # N-6104. Natural RNA base loaded support. Results of capillary electrophoresis analysis are illustrated in FIGS. 24A-24C.

Oligonucleotide Synthesis Example 5

Oligonucleotide 3

Figure 25A:
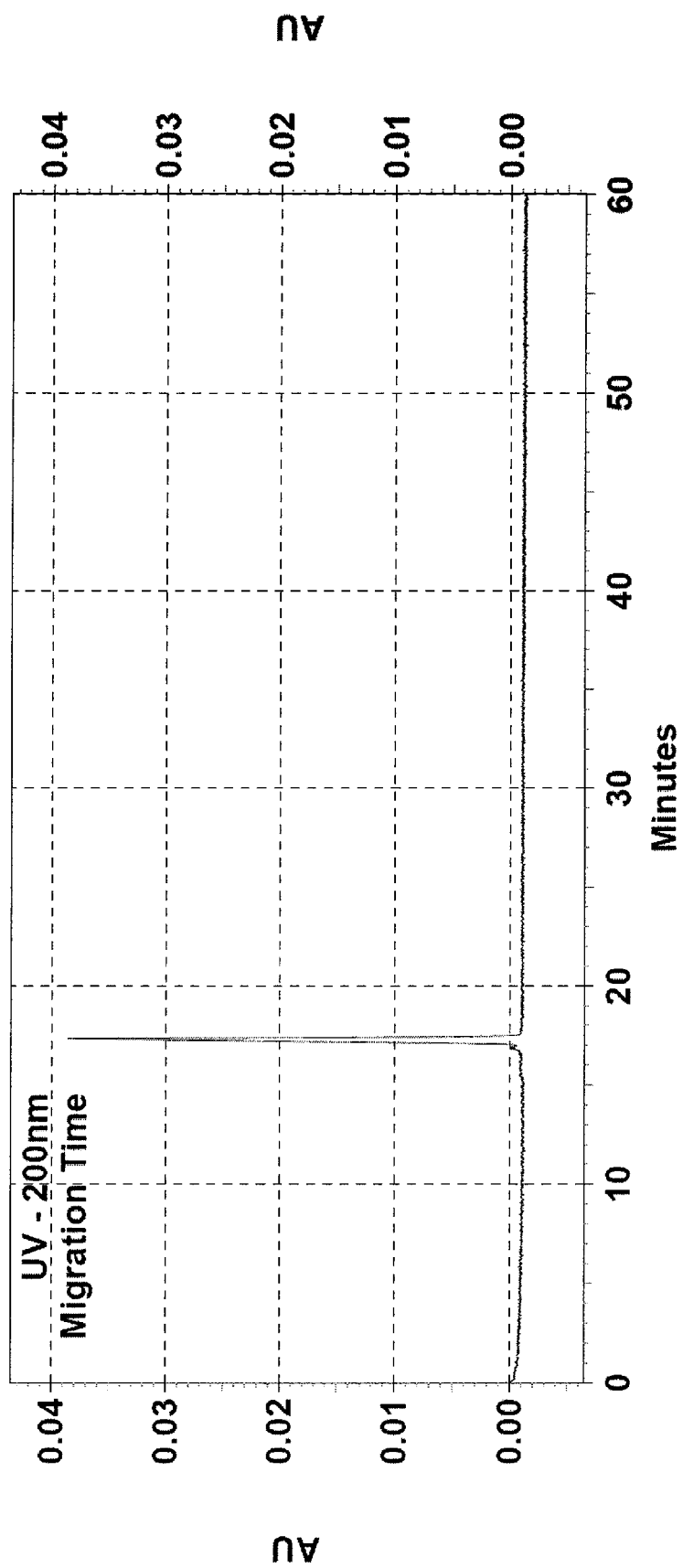
FIG. 25A is a capillary electrophoresis analysis of the purified oligonucleotide SEQ ID No.3 natural RNA.
Figure 25C:
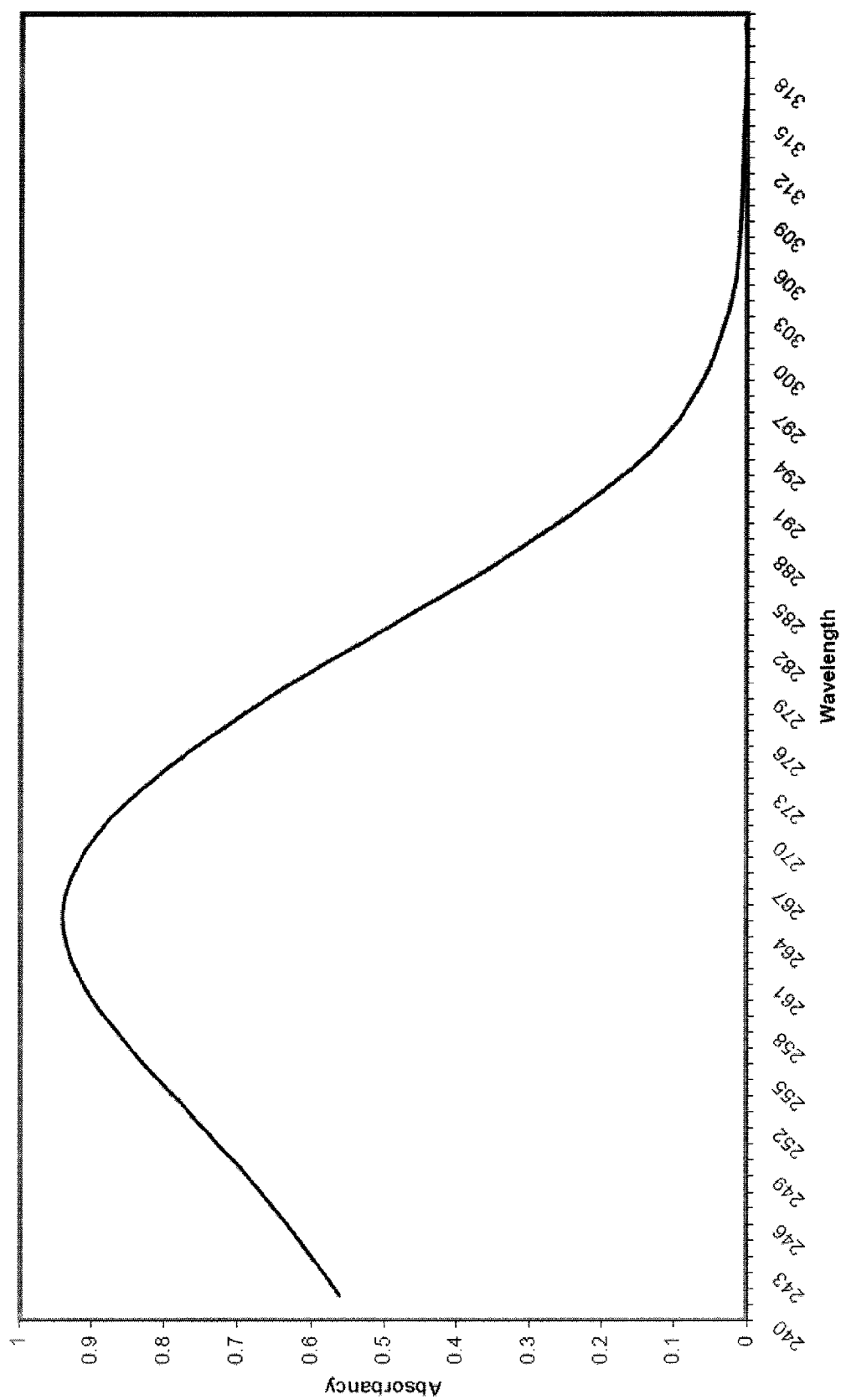
FIG. 25C is a UV analysis of the purified oligonucleotide SEQ ID No.3 natural RNA.

Oligonucleotide 3 was synthesized to have a sequence of SEQ ID NO: 3, consisting of unmodified natural bases Uridine and cytidine, guanidine and adenosine. The oligonucleotide was synthesized using 5'→3' directed RNA phosphoramidite chemistry in 1 micro mole scale. The synthesis were performed on Expedite 8900 synthesizer using standard RNA 1 micro mole cycle and coupling time of the monomers with solid support 10.0 minute. The Amidites used included (A) 5'-O-DMT-2'-O-tert-Butyldimethylsilyl-Uridine-3'-N,N-diisopropyl cyanoethyl phosphoramidite, Natural RNA base for natural RNA base sequence, ChemGenes Catalog product, ANP-5674; (B) 5'-O-DMT-2'-O-tert-Butyldimethylsilyl-Cytidine $N^{bz}$-3'-N,N-diisopropyl cyanoethyl phosphoramidite, Natural RNA base for natural RNA base sequence, ChemGenes Catalog product, ANP-5672; (C) 5'-O-DMT-2'-O-tert-Butyldimethylsilyl-Adenosine $N^{bz}$-3'-N,N-diisopropyl cyanoethyl phosphoramidite, Natural RNA base for natural RNA base sequence, ChemGenes Catalog product, ANP-5671; and (D) 5'-O-DMT-2'-O-tert-Butyldimethylsilyl-guanosine $N^{ibu}$-3'-N N-diisopropyl cyanoethyl phosphoramidite, Natural RNA base for natural RNA base sequence, ChemGenes Catalog product, ANP-5673. The solid support used was 5'-O-DMT-3'-O-tert-Butyldimethylsilyl-Uridine-2'-succinyl lcaa—A support produced by ChemGenes Corp., Cat # N-6104. Natural RNA base loaded support. Results of capillary electrophoresis analysis are illustrated in FIGS. 25A-25C.

Several preferred RNA sequences having sugar labeled with deuterium will be synthesized and used for biological assays and testing according to the methodology described above, see Table 2. The steps involved in the synthesis are not expected to cause loss of any deuterium and the deuterium/hydrogen ratio is expected to be maintained.

TABLE 2

Additional Deuterated/Natural Oligonucleotide sequences to be synthesized by conventional synthesis method.

| SEQ ID NUMBER | SEQUENCE | NAME |
| --- | --- | --- |
| SEQ ID NO. 4 | CAUUGGUUCAAACAU | ECX |
| SEQ ID NO. 5 | UUGAUGAAACAU | CLX |
| SEQ ID NO. 6 | CAGUUCAAACAU | PSX |
| SEQ ID NO. 7 | GACCAGUUCAAACAU | PSX-2 |
| SEQ ID NO. 8 | AGGUUCAAACAU | KLX |
| SEQ ID NO. 9 | AAACGCCUCCAU | STRX |

TABLE 2-continued

Additional Deuterated/Natural Oligonucleotide sequences to be synthesized by conventional synthesis method.

| SEQ ID NUMBER | SEQUENCE | NAME |
| --- | --- | --- |
| SEQ ID NO. 10 | AAAUGAAAAUGUCAU | STRX-2 |
| SEQ ID NO. 11 | AAAUUCUAACAU | STAX |
| SEQ ID NO. 12 | UUCAAAUUCUAACAU | STAX-2 |

Oligonucleotide Synthesis Example 6

Oligonucleotide 4

Figure 26A:
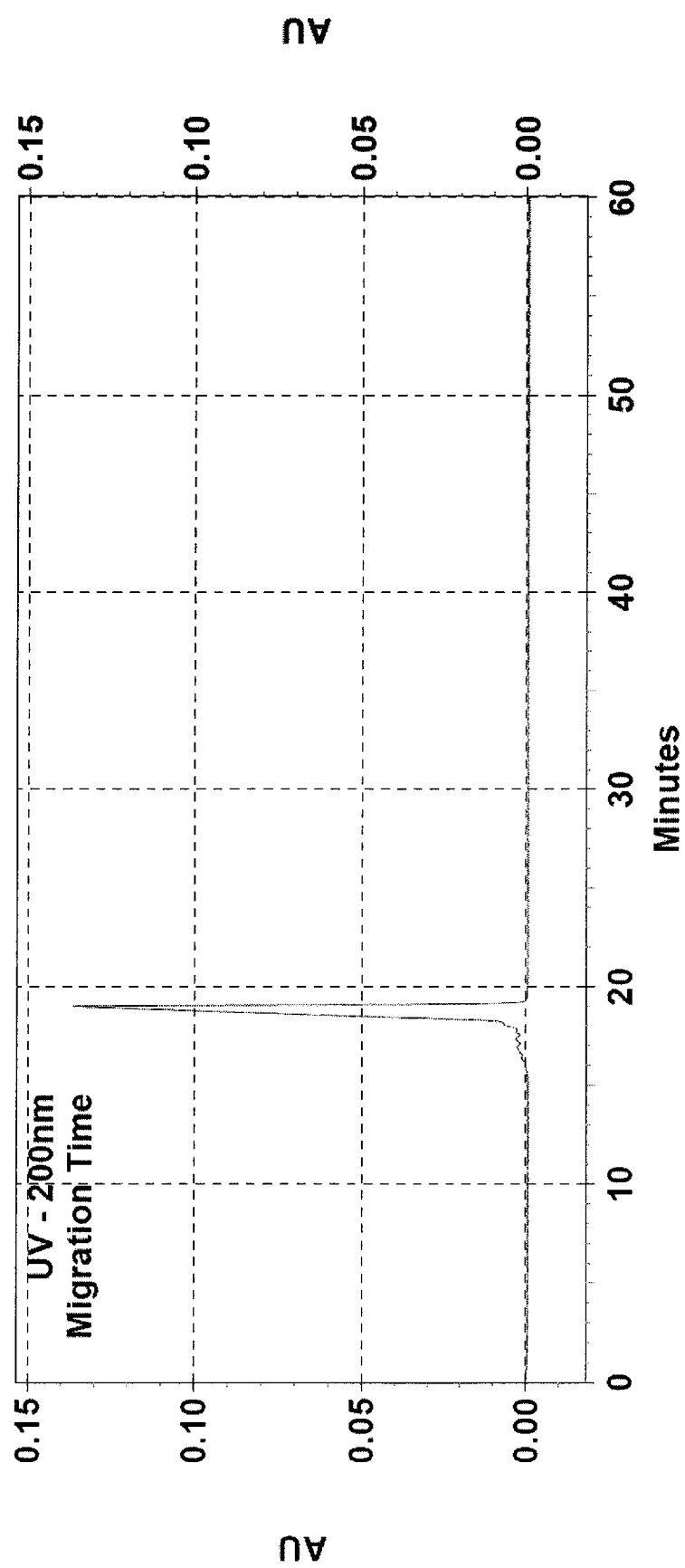
FIG. 26A is a capillary electrophoresis analysis of the purified oligonucleotide SEQ ID No.4 natural RNA.
Figure 26C:
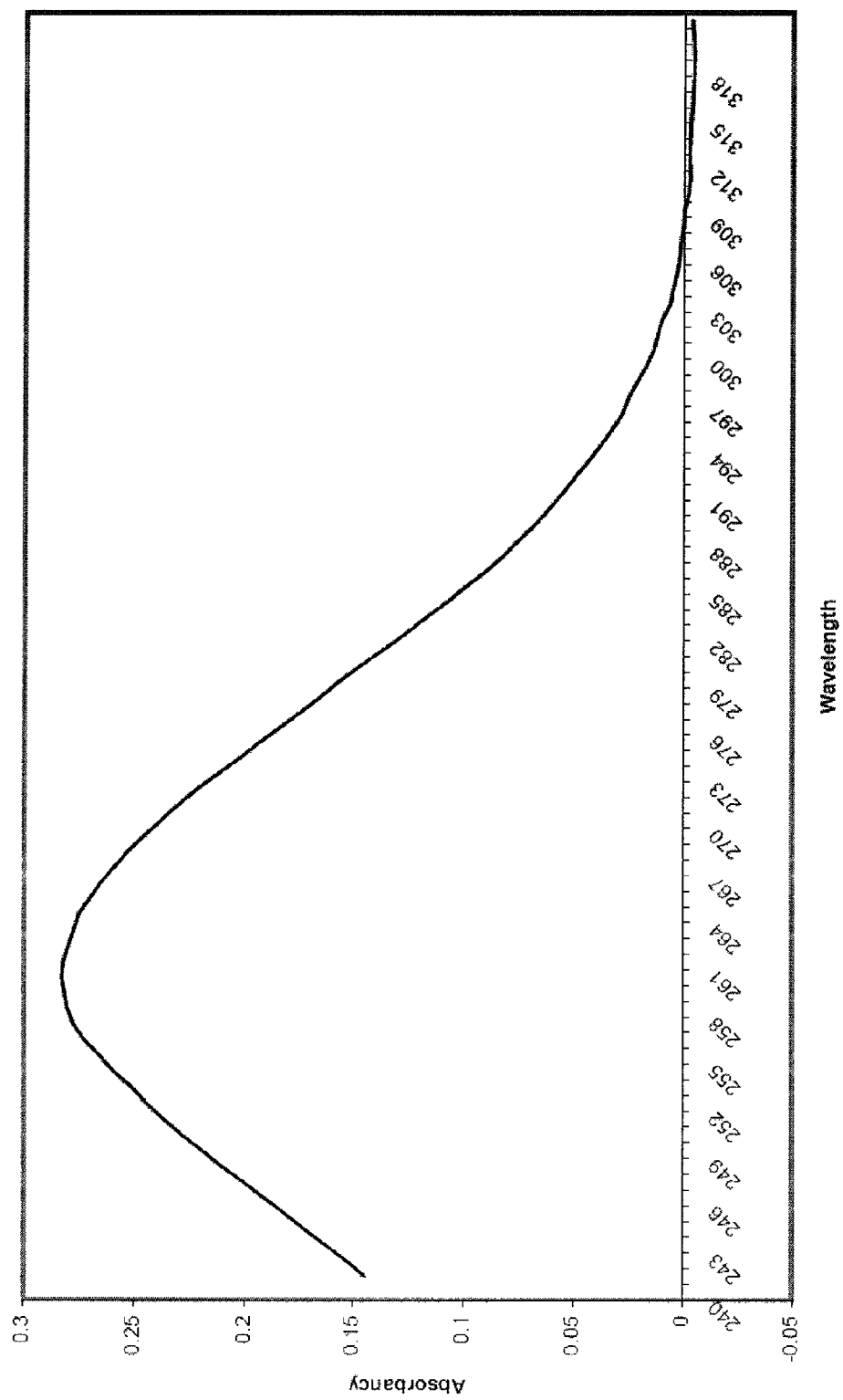
FIG. 26C is a UV analysis of the purified oligonucleotide SEQ ID No.4 natural RNA.
Figure 27A:
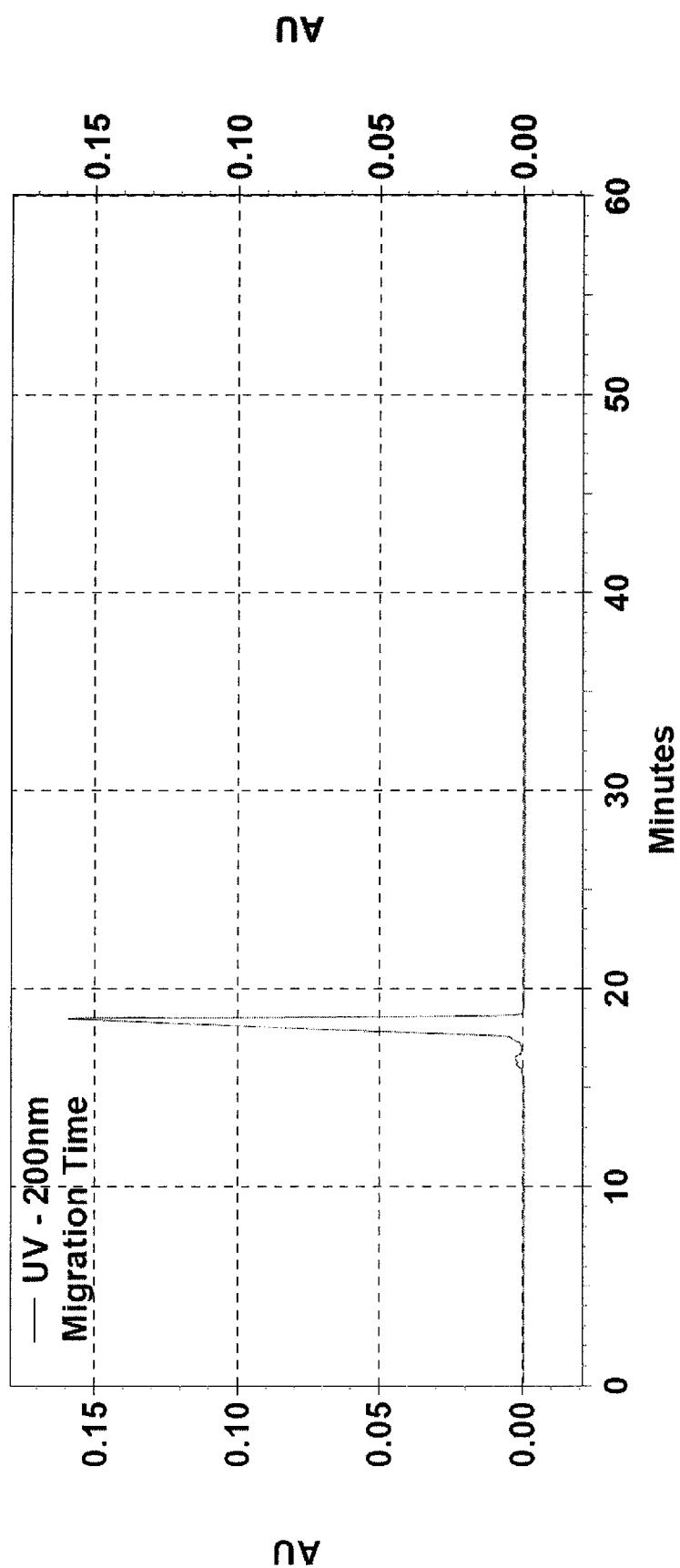
FIG. 27A is a capillary electrophoresis analysis of the purified oligonucleotide SEQ ID No.5 natural RNA.
Figure 27C:
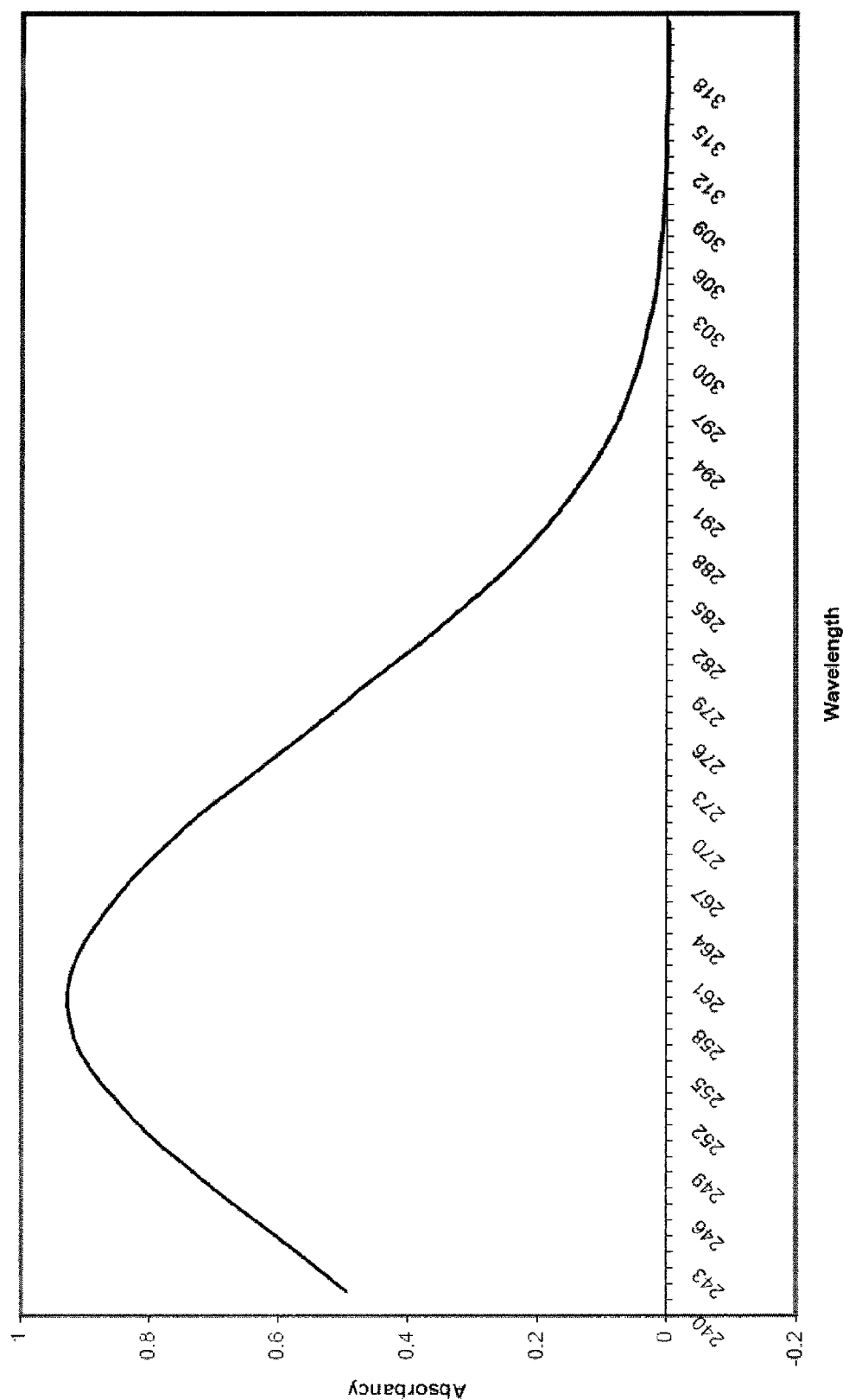
FIG. 27C is a UV analysis of the purified oligonucleotide SEQ ID No.5 natural RNA.

Using the procedures outlined above, Oligonucleotide 4 having SEQ ID NO: 4, having a sequence of r-C*A*U*U*G*G*U*U*C*A*A*A*C*A*U* where r is a ribo-oligonucleotide or an RNA sequence; * denotes a partially of fully deuterated ribose, such as 2,3,4,5,5'pentadeuterium-D ribofuranoside attached to each nucleoside unit of the RNA molecule with a natural phosphodiester backbone, as illustrated in FIG. 8, can be synthesized. Oligonucleotide 4 having SEQ ID NO: 4 can also be synthesized to have a sequence of r-C*p(s)A*p(s)U*p(s)U*p(s)G*p(s)G*p(s)U* p(s)U*p(s)C*p(s)A*p(s)A*p(s)A*p(s)C*p(s)A*p(s)U* where r is a ribo-oligonucleotide or an RNA sequence;  denotes a partially or fully deuterated ribose, such as 2,3,4,5, 5'pentadeuterium-D ribofuranoside attached to each nucleoside unit of the RNA molecule, p(s) denotes internucleotide phosphorothioate. Additionally, Oligonucleotide 4 having SEQ ID NO: 4 may be synthesized, using deuterated phosphoramidites and natural phosphoramidites, to consist of a mixture of partially or fully deuterated ribose and natural ribose attached to the nucleobases with a natural phosphodiester linkages, or variant nucleotide linkages such as a phosphorothioate linkage. As used herein, the term partially refers to one or more positions on the sugar and/or base portion that does not include a deuterium. Additionally, the term could refer to synthesized oligonucleotides that include a mix of ribose units that are deuterated and ribose units that are not deuterated as part of the backbone. Results of capillary electrophoresis analysis are illustrated in FIGS. 26A-26C**.

Oligonucleotide Synthesis Example 7

Oligonucleotide 5

Using the procedures outlined above, Oligonucleotide 7 having SEQ ID NO: 5, having a sequence of r-U*U*G*A*U*G*A*A*A*C*A*U* where r is a ribo-oligonucleotide or an RNA sequence; * denotes a partially or fully deuterated ribose, such as 2,3,4,5,5'-pentadeuterium-D ribofuranoside attached to each nucleoside unit of the RNA molecule with a natural phosphodiester backbone, as illustrated in FIG. 8, can be synthesized. Oligonucleotide 7 having SEQ ID NO:5 can also be synthesized to have a sequence of r-U*p(s)U*p(s)G*p(s)A*p(s)U*p(s)G*p(s)A*p(s)A*p(s) A*p(s)C*p(s)A*p(s)U* where r is a ribo-oligonucleotide or an RNA sequence;  denotes a partially or fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 7 having SEQ ID NO: 5 may be synthesized, using deuterated phosphoramidites and nature phosphoramidites, having a mixture of partially or fully deuterated ribose and natural ribose attached to each nucleobase and having a natural phosphodiester nucleotide linkage, or variant linkages such as phosphorothioate linkage. Results of capillary electrophoresis analysis are illustrated in FIGS. 25A-25C**.

Oligonucleotide Synthesis Example 8

Oligonucleotide 6

Using the procedures outlined above, Oligonucleotide 6 having SEQ ID NO: 6 having a sequence of r-C*A*G*U*U*C*A*A*A*C*A*U* where r is a ribo-oligonucleotide or an RNA sequence; * denotes a partially or fully deuterated ribose, such as 2,3,4,5,5'pentadeuterium-D ribofuranoside attached to each nucleoside unit of the RNA molecule with a natural phosphodiester backbone, as illustrated in FIG. 8, can be synthesized. Oligonucleotide 6 having SEQ ID NO: 6 can also be synthesized to have a sequence of r-C*p(s)A*p(s)G*p(s)U*p(s)U*p(s)C*p(s)A*p(s)A*p(s)A*p(s)C*p(s)A*p(s)U* where r is a ribo-oligonucleotide or an RNA sequence; wherein * denotes a partially or fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 6 having SEQ ID NO: 6 may be synthesized, using deuterated phosphoramidites and natural phosphoramidites, having a mixture of partially or fully deuterated ribose and natural ribose attached to the nucleobases with a natural phosphodiester nucleotide linkage, or a variant linkage such as phosphorothioate linkage.

Oligonucleotide Synthesis Example 9

Oligonucleotide 7

Using the procedures outlined above, Oligonucleotide 7, having SEQ ID NO: 7 having a sequence of r-G*A*C*C*A*G*U*U*C*A*A*A*C*A*U* where r is a ribo-oligonucleotide or an RNA sequence; * denotes a partially or fully deuterated ribose, such as 2,3,4,5,5'pentadeuterium-D ribofuranoside attached to each nucleoside unit of the RNA molecule with a natural phosphodiester backbone, as illustrated in FIG. 8, was synthesized. Oligonucleotide 7, having SEQ ID NO: 7 can also be synthesized to have a sequence of r-C*p(s)A*p(s)G*p(s)U*p(s)U*p(s)C*p(s)A*p(s)A*p(s)A*p(s)C*p(s)A*p(s)U*, wherein * where r is a ribo-oligonucleotide or an RNA sequence; ** denotes a partially of fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 7, having SEQ ID NO: 7 may be synthesized, using deuterated phosphoramidites and nature phosphoramidites, having a mixture of partially or fully deuterated ribose and natural ribose attached to the nucleobases, and a natural phosphodiester nucleotide linkage, or variant linkages such as phosphorothioate linkage.

Oligonucleotide Synthesis Example 10

Oligonucleotide 8

Using the procedures outlined above, Oligonucleotide 8 having SEQ ID NO:8 having a sequence of r-A*G*G*U*U*C*A*A*A*C*A*U* where r is a ribo-oligonucleotide or an RNA sequence; * denotes a partially or fully deuterated ribose, such as 2,3,4,5,5'pentadeuterium-D ribofuranoside attached to each nucleoside unit of the RNA molecule with a natural phosphodiester backbone, as illustrated in FIG. 8, can be synthesized. Oligonucleotide 8 having SEQ ID NO:8 can also be synthesized to have a sequence of r-A*p(s)G*p(s)G*p(s)U*p(s)U*p(s)C*p(s)A*p(s)A*p(s)A*p(s)C*p(s)A*p(s)U*, wherein * where r is a ribo-oligonucleotide or an RNA sequence; ** denotes a partially or fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 8 having SEQ ID NO:8 may be synthesized, using deuterated phosphoramidites and nature phosphoramidites, having a mixture of partially or fully deuterated ribose and natural ribose attached to the nucleobases, and a natural phosphodiester linkage, or variant nucleotide linkage, such as a phosphorothioate linkage.

Oligonucleotide Synthesis Example 11

Oligonucleotide 9

Using the procedures outlined above, Oligonucleotide 11 having SEQ ID NO: 11 having a sequence of r-A* A* A* C* G* C* C* U* C* C* A* U* where r is a ribo-oligonucleotide or an RNA sequence; * denotes a partially or fully deuterated ribose, such as 2,3,4,5,5'pentadeuterium-D ribofuranoside attached to each nucleoside unit of the RNA molecule with a natural phosphodiester backbone, as illustrated in FIG. 8, was synthesized. Oligonucleotide 11 having SEQ ID NO: 11 can also be synthesized to have a sequence of r-A*p(s) A*p(s) A*p(s) C*p(s) G*p(s) C*p(s) C*p(s)U*p(s)C*p(s)C*p(s)A*p(s)U*, wherein * where r is a ribo-oligonucleotide or an RNA sequence; ** denotes a partially or fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 11 having SEQ ID NO: 11 may be synthesized, using deuterated phosphoramidites and nature phosphoramidites, having a mixture of partially or fully deuterated ribose and natural ribose attached to nucleobases, and a natural phosphodiester linkage, or variant nucleotide linkage, such as a phosphorothioate linkage.

Oligonucleotide Synthesis Example 12

Oligonucleotide 10

Using the procedures outlined above, Oligonucleotide 10 having SEQ ID NO: 10, having a sequence of r-A*A*A*C*G*C*C*U*C*C*A*U* where r is a ribo-oligonucleotide or an RNA sequence; * denotes a partially or fully deuterated ribose, such as 2,3,4,5,5'pentadeuterium-D ribofuranoside attached to each nucleoside unit of the RNA molecule with a natural phosphodiester backbone, as illustrated in FIG. 8, can be synthesized. Oligonucleotide 10 having SEQ ID NO: 10 can also be synthesized to have a sequence of r-rA*p(s)A*p(s)A*p(s)U*p(s)G*p(s)A*p(s)A*p(s)A*p(s)U*p(s)*G*p(s)*U*p(s)*p(s)Ap(s)U**, wherein * where r is a ribo-oligonucleotide or an RNA sequence; ** denotes a partially or fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 10 having SEQ ID NO: 10 may be synthesized, using deuterated phosphoramidites and nature phosphoramidites, having a mixture of partially or fully deuterated ribose and natural ribose attached to a nucleobase, and a natural phosphodiester linkage, or variant nucleotide linkage, such as a phosphorothioate linkage.

Oligonucleotide Synthesis Example 13

Oligonucleotide 11

Using the procedures outlined above, Oligonucleotide 11 having SEQ ID NO: 11, having a sequence of r-A*A*A*U*U*C*U*A*A*C*A*U*, where r is a ribo-oligonucleotide or an RNA sequence; * denotes a partially or fully deuterated ribose, such as 2,3,4,5,5'pentadeuterium-D ribofuranoside attached to each nucleoside unit of the RNA molecule with a natural phosphodiester backbone, as illustrated in FIG. 8, was synthesized. Oligonucleotide 11 having SEQ ID NO: 11 can also be synthesized to have a sequence of r-A*p(s)A*p(s)A*p(s)U*p(s)U*p(s)C*p(s)U*p(s)A*p(s)A*p(s)C*p(s)A*p(s)U*, wherein * where r is a ribo-oligonucleotide or an RNA sequence; ** denotes a partially or fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 11 having SEQ ID NO: 11 may be synthesized, using deuterated phosphoramidites and nature phosphoramidites, having a mixture of partially or fully deuterated ribose and natural ribose attached to nucleobases, and a natural phosphodiester linkage, or variant nucleotide linkages such as a phosphorothioate linkage.

Oligonucleotide Synthesis Example 14

Oligonucleotide 12

Using the procedures outlined above, Oligonucleotide 12 having SEQ ID NO: 12, having a sequence of r-U*U*C*A*A*A*U*U*C*U*A*A*C*A*U*, wherein r is a ribo-oligonucleotide or an RNA sequence; * denotes a partially or fully deuterated ribose, such as 2,3,4,5,5'pentadeuterium-D ribofuranoside attached to each nucleoside unit of the RNA molecule with a natural phosphodiester backbone, as illustrated in FIG. 8, can be synthesized. Oligonucleotide 12 having SEQ ID NO: 12 can also be synthesized to have a sequence of r-U*p(s)U*p(s)C*p(s)A*p(s)A*p(s)A*p(s)U*p(s)U*p(s)C*p(s)U*p(s)A*p(s)A*p(s)C*p(s)A*p(s)U*, wherein * where r is a ribo-oligonucleotide or an RNA sequence; ** denotes a partially or fully deuterated ribose, such as 2,3,4,5,5'pentadeuterium-D ribofuranoside attached to each nucleoside unit of the RNA molecule, p(s) denotes internucleotide phosphorothioate. Additionally, Oligonucleotide 12 having SEQ ID NO: 12 may be synthesized, using deuterated phosphoramidites and nature phosphoramidites, having a mixture of partially or fully deuterated ribose and natural ribose attached to nucleobases, and a natural phosphodiester linkage, or variant nucleotide linkage such as a phosphorothioate linkage.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A modified ribo-oligonucleotide having the formula comprising:

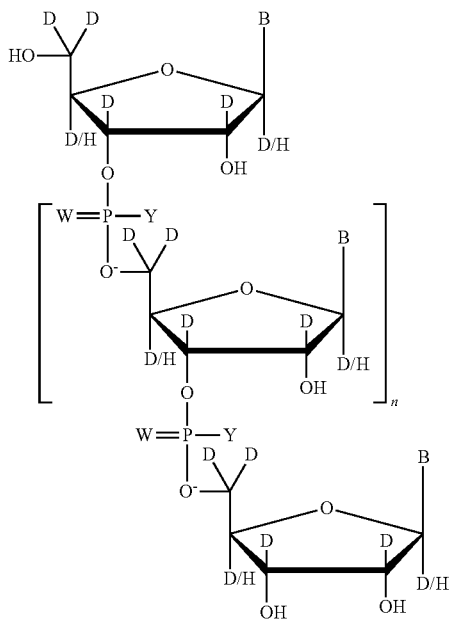

wherein D is deuterium; B is a nucleobase; n is a number greater than 1 and represents the number of nucleosides in the oligonucleotide; W is oxygen or sulfur; Y is oxygen, C1-C18 alkoxy, C1-18 alkyl; NHR3 with R3 being C1-C18 alkyl or C1-C4 alkoxy-C1-C6-alkyl; NR3R4 in which R3 is as defined above and R4 is C1-C18 alkyl, or in which R3 is as defined above and R4 is C1-C18 -alkyl, or in which R3 and R4 form together with the nitrogen atom carrying them, a 5-6 membered heterocyclic ring which can additionally contain another hetero atom from the series O, S and N.

2. The modified ribo-oligonucleotide according to claim 1 wherein W is oxygen and Y is oxygen.

3. The modified ribo-oligonucleotide according to claim 1 wherein W is sulfur and Y is oxygen.

4. The modified ribo-oligonucleotide according to claim 1 wherein at least one deuterium is replaced by a hydrogen.

5. The modified ribo-oligonucleotide according to claim 1 wherein said B is a naturally occurring nucleobase, a modified nucleobase, or combinations thereof.

6. The modified ribo-oligonucleotide according to claim 1 wherein B includes a purine, a pyrimidine, or combinations thereof.

7. The modified ribo-oligonucleotide according to claim 6 wherein B is partially or fully deuterated.

8. The modified oligonucleotide according to claim 7 wherein B is deuterioadenine, deuteriocytidine, deuterioguanine, deuteriouracil, or combinations thereof.

9. The modified ribo-oligonucleotide according to claim 1 wherein said nucleotide has a variant internucleotide linkage.

10. The modified ribo-oligonucleotide according to claim 9 wherein said ribose sugars are fully deuterated.

11. The modified ribo-oligonucleotide according to claim 9 wherein said ribose sugars are partially deuterated.

12. The modified ribo-oligonucleotide according to claim 9 having a mixture of fully deuterated ribose sugars and partially deuterated ribose sugars.

13. The modified ribo-oligonucleotide according to claim 9 wherein said B', B", and B'" is a naturally occurring nucleobase, a modified nucleobase, or combinations thereof.

14. The modified ribo-oligonucleotide according to claim 12 wherein B', B", and B'", includes a purine, a pyrimidine, or combinations thereof.

15. The modified ribo-oligonucleotide according to claim 13 wherein B', B", and B'" is partially or fully deuterated.

16. The modified ribo-oligonucleotide according to claim 1 wherein the nucleotide sequence is SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

17. The modified ribo-oligonucleotide according to claim 15 wherein said ribose are partially deuterated.

18. The modified ribo-oligonucleotide according to claim 15 wherein said ribose units include at least one natural ribose unit and at least one deuterated ribose unit.

19. The modified ribo-oligonucleotide according to claim 15 wherein the nucleotide linkage is a phosphorothioate linkage.

20. The modified ribo-oligonucleotide according to claim 15 wherein the Y is an oxygen, said oxygen further containing X—C—($Y_1Y_2Y_3Y_4$), wherein W can be oxygen ($O^-$) or sulfur ($S^-$); Y can be singly or multiply hydrogen, methyl, ethyl; X can be an electron attracting group, CN, $NO_2$, $SO_2$, or aromatic groups.

21. A method for synthesizing a modified ribo-oligonucleotide comprising the step of synthesizing a modified ribo-oligonucleotide having at least two ribo-nucleotides being deuterated.

22. The method for synthesizing a modified oligonucleotide according to claim 21 wherein said nucleobases are natural nucleobases, modified nucleobases, or combinations thereof.

23. The method for synthesizing a modified oligonucleotide according to claim 21 wherein said natural nucleobases are adenine, cytosine, guanine, uracil, or combinations thereof.

24. The method for synthesizing a modified oligonucleotide according to claim 21 wherein said RNA nucleotides has a mixture of naturally occurring nucleotides and deuterated nucleotides.

25. The method for synthesizing a modified oligonucleotide according to claim 21 wherein said RNA is diluted, said modified oligonucleotide having the desired sequence with non-modified oligonucleotides to form a modified oligonucleotide solution with less than 100% deuteration.

* * * * *

SEQUENCE LISTING

```
<160> NUMBER OF SEQ ID NOS: 12

<210> SEQ ID NO 1
<211> LENGTH: 12
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 1
cucucucucu cu                                                          12

<210> SEQ ID NO 2
<211> LENGTH: 15
<212> TYPE: RNA
<213> ORGANISM: Artificial Sequence
<220> FEATURE:
<223> OTHER INFORMATION: Description of Artificial Sequence: Synthesized
      nucleic acid molecule
```

```
<400> SEQUENCE: 2
cauugguuca aacau                                                    15

<210> SEQ ID NO 3
<211> LENGTH: 12
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 3
agguucaaac au                                                       12

<210> SEQ ID NO 4
<211> LENGTH: 15
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 4
cauugguuca aacau                                                    15

<210> SEQ ID NO 5
<211> LENGTH: 12
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 5
uugaugaaac au                                                       12

<210> SEQ ID NO 6
<211> LENGTH: 12
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 6
caguucaaac au                                                       12

<210> SEQ ID NO 7
<211> LENGTH: 15
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 7
gaccaguuca aacau                                                    15
```

```
<210> SEQ ID NO 8
<211> LENGTH: 12
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 8
agguucaaac au                                                          12

<210> SEQ ID NO 9
<211> LENGTH: 12
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 9
aaacgccucc au                                                          12

<210> SEQ ID NO 10
<211> LENGTH: 15
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 10
aaaugaaaau gucau                                                       15

<210> SEQ ID NO 11
<211> LENGTH: 12
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 11
aaauucuaac au                                                          12

<210> SEQ ID NO 12
<211> LENGTH: 15
<212> TYPE: RNA
<213> ORGANISM: Artificial Sequence
<220> FEATURE:
<223> OTHER INFORMATION: Description of Artificial Sequence: Synthesized
      nucleic acid molecule

<400> SEQUENCE: 12
uucaaauucu aacau                                                       15
```